US006326469B1

(12) United States Patent
Ullrich et al.

(10) Patent No.: US 6,326,469 B1
(45) Date of Patent: Dec. 4, 2001

(54) MEGAKARYOCYTIC PROTEIN TYROSINE KINASES

(75) Inventors: Axel Ullrich, Portola Valley; Mikhail Gishizky, Palo Alto, both of CA (US); Irmingard Sures, Munich (DE)

(73) Assignees: Sugen, Inc., Redwood City, CA (US); Max-Planck-Gessellschaft zur Forderung der Wissenschaften e.V., Munich (DE)

( * ) Notice: Subject to any disclaimer, the term of this patent is extended or adjusted under 35 U.S.C. 154(b) by 0 days.

(21) Appl. No.: 08/426,509

(22) Filed: Apr. 21, 1995

Related U.S. Application Data

(63) Continuation-in-part of application No. 08/232,545, filed on Apr. 22, 1994.

(51) Int. Cl.[7] .......................... C07K 17/00; C12P 21/06; C12P 21/04; C12N 9/12
(52) U.S. Cl. ...................... 530/350; 530/350; 435/69.1; 435/69.7; 435/194
(58) Field of Search ........................ 530/350; 435/69.1, 435/69.7, 194

(56) References Cited

U.S. PATENT DOCUMENTS 5,635,177 * 6/1997 Bennett .............................. 424/143.1

FOREIGN PATENT DOCUMENTS

Wo 93/15201    1/1993  (WO).

OTHER PUBLICATIONS

Sambrook et al., Molecular Cloning, A Laboratory Manual, 2nd Ed., vol. 3, pp. 16.2–16.30 and 17.2–17.28, Cold Spring Harbor Laboratory Press, CSH, 1989.*
Maniatis et al., Molecular Cloning, A Laboratory Manual, pp. 422–433, Cold Spring Harbor Laboratory Press, CSH, 1982.*
Devereux et al., "A comprehensive set of sequence analysis programs for the VAX," *Nucl. Acids Res.*, 12(1):387–395 (1984).
Heldin and Westermark, "Plateler–derived growth factor: mechanism of action and possible in vivo function." *Cell Regulation*, 1:555–566 (Jul., 1990).
Hiraj et al., "A Novel Putative Tyrosine Kinase Receptor Encoded by the eph Gene," *Science*, 238:1717–1720 (Dec. 18, 1987).
Huang et al., "The Hematopoietic Growth Factor KL is Encoded by the SI Locus and Is the Ligand of the c–kit Receptor, the Gene Product of the W Locus," *Cell*. 63:225–233 (Oct. 5, 1990).
Lichter et al., "Delineation of individual human chromosomes in metaphase and interphase cells by in situ suppression by bridization using recombinant DNA libraries," *Hum. Genet.*, 80:224–234 (1988).

Morgenstern and Land, "Advanced mammalian gene transfer: high titre retroviral vectors with multiple drug selection markers and a complementary helper–free packaging cell line," *Nucl. Acids Res.*, 18(12):3587–3596 (1990).
Mustelin and Burn, "Regulation of src family tyrosine kinases in lymphocytes," *TIBS*. 18:215–220 (1993).
Pear et al., "Production of high–titer helper–free retroviruses by transient transfection," *Proc. Natl. Acad. Sci. USA*. 90:8392–8396 (Sep., 1993).
Sherr et al., "The c–fms Proto–oncogene Product is Related to the Receptor for the Mononuclear Phagocyte Growth Factor, CSF–1," *Cell*. 41:665–676 (Jul., 1985).
Staunton et al., "The Arrangement of the Immunoglobulin–like Domains of ICAM–1 and the Binding Sites for LFA–1," *Cell*. 61:243–254 (Apr. 20, 1990).
Wang, "Nuclear protein tyrosine kinases," *TIBS*. 19:373–379 (Sep., 1994).
Wilks, "Two putative protein–tyrosine kinases identified by application of the polymerase chain reaction," *Proc. Natl. Acad. Sci. USA*. 86:1603–1607 (Mar. 1989).
Tsukada et al., *Cell*. 72:279–290, 1991.
Yamada et al., *Biochem. Bioplys. Res. Comm*. 172:231–240, 1993.
Hamaguchi et al., "Characterization of mouse non–receptor tyrosine kinase gene, HYL," *Oncogene*, (1994), 9, 3371–3374, Macmillan Press Ltd., 1994.
Tamagnone et al., "BMX, a novel nonreceptor tyrosine kinase gene of the BTK/ITK/TEC/TXK family located in chromosome Xp22.2," *Oncogene* (1994), 9, 3683–3688, Macmillan Press Ltd., 1994.
Morgenstern and Land, "Advanced mammalian gene transfer: high titre retroviral vectors with multiple drug selection markers and a complementary helper–free packaging cell line," *Nucl. Acids Res.*, 18(12):3587–3596 (1990).
Mustelin and Burn, "Regulation of src family tyrosine kinases in lymphocytes," *TIBS*. 18:215–220 (1993).
Pear et al., "Production of high–titer helper–free retroviruses by transfection," *Proc. Natl. Acad. Sci. USA*. 90:8392–8396 (Sep., 1993).
Sherr et al., "The c–fms Proto–oncogene Product is Related to the Receptor for the Mononuclear Phagocyte Growth Factor, CSF–1," *Cell*. 41:665–676 (Jul., 1985).
Staunton et al., "The Arrangement of the Immunoglobulin–like Domains of ICAM–1 and the Binding Sites for LFA–1," *Cell*. 61:243–254 (Apr. 20, 1990).

(List continued on next page.)

*Primary Examiner*—Jeffrey Stucker
*Assistant Examiner*—Jegatheesan Seharaseyon
(74) *Attorney, Agent, or Firm*—Foley & Lardner

(57) ABSTRACT

The present invention relates to novel cytoplasmic tyrosine kinases isolated from megakaryocytes (megakaryocyte kinases or MKKs) which are involved in cellular signal transduction pathways and to the use of these novel proteins in the diagnosis and treatment of disease. The present invention further relates to specific megakaryocyte kinases, designated MKK1, MKK2 and MKK3, and their use as diagnostic and therapeutic agents.

11 Claims, 26 Drawing Sheets

OTHER PUBLICATIONS

Figure 5:
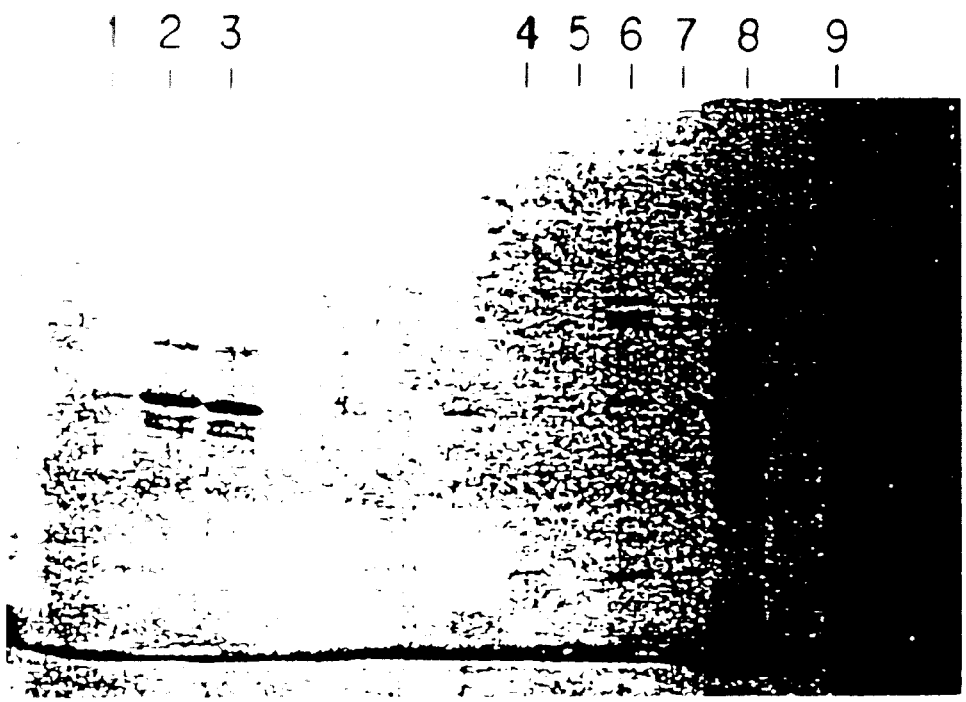

Wang, "Nuclear protein tyrosine kinases," *TIBS.* 19:373–379 (Sep., 1994).

Wilks, "Two putative protein–tyrosine kinases identified by application of the polymerase chain reaction," *Proc. Natl. Acad. Sci. USA.* 86:1603–1607 (Mar. 1989).

Tsukada et al., *Cell.* 72:279–290, 1991.

Yamada et al., *Biochem. Bioplys. Res. Comm.* 172:231–240, 1993.

Hamaguchi et al., "Characterization of mouse non–receptor tyrosine kinase gene, HYL," *Oncogene,* (1994), 9, 3371–3374, Macmillan Press, Ltd., 1994.

Tamagnone et al., "BMX, a novel nonreceptor tyrosine kinase gene of the BTK/ITK/TEC/TXK family located in chromosome Xp22.2," *Oncogene* (1994), 9, 3683–3688, Macmillan Press Ltd., 1994.

Cance et al., *Cell Oncogene & Diff.*, vol. 5, pp. 1347–1355, 1994.

Aaronson, Stuart A., Nov. 22, 1991, "Growth Factors and Cancer," *Science* 254:1146–1153.

Arpala et al., Mar. 11, 1994, "Defective T Cell Receptor Signaling and CD8+ Thymic Selection in Humans Lacking Zap–70 Kinase," *Cell* 76:947–958.

Bearman et al., Jan., 1979, "Acute ("Malignant") Myelosclerosis," *Cancer* 43(1):279–293.

Bennett et al., Jan. 14, 1994, "Identification and Characterization of a Novel Tyrosine Kinase from Megakaryocytes," *J. of Biol. Chem.*, 269(2):1068–1074.

Bolen, Joseph B., 1993, "Nonreceptor tyrosine protein kinases," *Oncogene* 8:2025–2031.

Brauninger et al., Dec. 22, 1993, "Characterization of the human CSK locus," *Ontogene* 8:1365–1369.

Brauninger et al., 1992, "Isolation and characterization of a human gene that encodes a new subclass of protein tyrosine kinases," *Gene* 110:205–211.

Butler et al., Jun. 15, 1982, "Idiopathic Acquired Sideroblastic Anemia Terminating in Acute Myelosclerosis," *Cancer* 49(12):2497–2499.

Eiseman et al., Oct., 1990, "src–Related Tyrosine Protein Kinases as Signaling Components in Hematopoietic Cells," *Cancer Cells* 2(10):303–310.

Fohlmeister et al., 1986, "Acute Megakaryocytic Myelosis Preceded by Myelodysplasia. Report of a Case and Review of the Literature," *VNU Science Press, Utrecht Akademiai Kiado* 2:151–160.

Hardie, D. Grahame, 1990, "Roles of Protein Kinases and Phosphatases in Signal Transduction," *Society for Experimental Biology*, pp. 241–255.

Heyeck et al., Jan., 1993, "Developmental regulation of a murine T–cell–specific tyrosine kinase gene, Tsk," *PNAS USA* 90:669–673.

Hoffman, Ronald, Sep., 1989, "Regulation of Megakaryocytopoiesis," *Blood* 74(4):1196–1212.

Ishida et al., 1993, "Biological and Biochemical Characteristics of Murine Megakaryoblastic Cell Line L8057," *Exp. Hematol.* 21:289–298.

Kawakami et al., Dec., 1986, "Isolation and Oncogenic Potential of a Novel Human src–Like Gene," *Molecular and Cellular Biology* 6(12):4195–4201.

Kipreos et al., Apr. 13, 1990, "Differential Phosphorylation of c–Abl in Cell Cycle Determined by cdc2 Kinase and Phosphatase Activity," *Science* 248:217–220.

Koch et al., May 3, 1991, "SH2 and SH3 Domains: Elements that Control Interactions of Cytoplasmic Signaling Proteins," *Science* 252:668–674.

Lee et al., 1994, "Cloning of FRK, a novel human intracellular SRC–like tyrosine kinase–encoding gene," *Gene* 138:247–251.

Long, Michael W., 1993, "Population Heterogeneity Among Cells of the Megakaryocyte Lineage," *Stem Cells* 11:33–40.

Lu et al., 1993, "Review of the Cytogenetic Changes in Acute Megakaryoblastic Leukemia: One Disease or Several?," *Cancer Genet Cytogenet* 67:81–89.

Maness, Patricia F., 1992, "Nonreceptor Protein Tyrosine Kinases Associated with Neuronal Development," *Dev. Neurosci* 14:257–270.

Mano et al., 1993, "Expression of a novel form of Tec kinase in hematopoietic cells and mapping of the gene to chromosome 5 near Kit," *Oncogene* 8:417–424.

Marino, Gregory G., Oct., 1989, "Acute myelofibrosis: Report of a cse and review of current literature," *JAOA* 89(10):1323–1329.

Mayer et al., Mar., 1988, "A novel viral oncogene with structural similarity to phospholipase C," *Nature* 332:272–275.

Moody et al., 1989, "Florid radiological appearance of megakaryoblastic leukaemia—an aid to earlier diagnosis," *Pediatric Radiology* 19:486–488.

Morgan et al., Jun. 2, 1989, "Mitosis–Specific Phosphorylation of $p60^{c-src}$ by $p34^{cdc2}$–Associated Protein Kinase," *Cell* 57:775–786.

Muller et al., 1992, "BCR First Exon Sequences Specifically Activate the BCR/ABL Tyrosine Kinase Oncogene of Philadelphia Chromosome–Positive Human Leukemias," *Mol. Cell. Bio.* 11:1785–1792.

Musacchio et al., Sep., 1993, "The PH domain: a common piece in the structural patchwork of signalling proteins," *TIBS 18*:343–348.

Pawson et al., Oct. 30, 1992, "SH2 and SH3 Domains: From Structure to Function," *Cell* 71:359–362.

Posada et al., Jun., 1992, "Molecular Signal Integration. Interplay Between Serine, Threonine, and Tyrosine Phosphorylation," *Mol. Biol. of the Cell* 3:583–592.

Rawlings et al., Jul. 16, 1993, "Mutation of Unique Region of Bruton's Tyrosine Kinase in Immunodeficient XID Mice," *Science* 261:358–361.

Sadowski et al., Dec., 1986, "A Noncatalytic Domain Conserved among Cytoplasmic Protein–Tyrosine Kinases Modifies the Kinase Function and Transforming Activity of Fujinami Sarcoma Virus $P130^{gag-fps}$," *Molecular and Cellular Biology* 6(12):4396–4408.

Sakano et al., 1994, "Molecular cloning of a novel non–receptor tyrosine kinase, HYL (hematopoietic consensus tyrosine–lacking kinase," *Oncogene* 9:1155–1161.

Schlessinger, Joseph, Nov., 1988, "Signal transduction by allosteric receptor oligomerization," *TIBS* 13:443–447.

Smith et al., 1990, "Myelofibrosis: A Review of Clinical and Pathologic Features and Treatment," *Oncology/Hematology* 10(4):305–314.

Soriano et al., Feb. 22, 1991, "Targeted Disruption of the c–src Proto–Oncogene Leads to Osteopetrosis in Mice," *Cell* 64:693–702.

Ullrich et al., Apr. 20, 1990, "Signal Transduction by Receptors with Tyrosine Kinase Activity," *Cell* 61:203–212.

Veillette et al., Feb., 1992, "Src–related protein tyrosine kinases and T–cell receptor signalling," *TIG* 8(2):61–66.

Vetrie et al., Jan. 21, 1993, "The gene involved in X–linked agammaglobulinaemia is a member of the src family of protein–tyrosine kinases," *Nature 361*:226–233.

Weaver et al., Sep., 1991, "CD8+ T–Cell Clones Deficient In the Expression of the CD45 Protein Tyrosine Phosphatase Have Impaired Responses to T–Cell Receptor Stimuli," *Mol. and Cell. Biol. 11(9)*:4415–4422.

White et al., 1987, "A Cascade of Tyrosine Autophosphorylation in the β–Subunit Activates the Phosphotransferase of the Insulin Receptor," *J. Biol. Chem. 263*:2969–2980.

Zsebo et al., Oct. 5, 1990, "Stem Cell Factor Is Encoded at the Sl Locus of the Mouse and Is the Ligand for the c–kit Tyrosine Kinase Receptor," *Cell 63*:213–224.

Cance et al., 1993, "Novel Protein Kinases Expressed in Human Breast Cancer," *International Journal of Cancer 54(4)*:571–577.

* cited by examiner

CTCCCTCCAAGTTGTGCAGCCGGGACCGCCTCGGGGTGTGCAGCCGGCTCGCGGAGGCCCTCCTGGGGGCGGCGCGGGGCGGCTCGGGG 90

GCGCCCCCTGAGCAGAAAACAGGAAGAACCAGGCTCGGTCCAGTGGCACCCAGCTCCCTACCTCCTGTGCCAGCCGCCTGGCCTGTGGCA 180

GGCCATTCCCAGCGTCCCCGACTGTGACCACTTGCTCAGTGTGCCTCTCACCTGCCTCAGTTTCCCTCTGGGGGGCCATGGCGGGGCCAC 270
                                                                                                                                        M  A  G  R

Smal

GCTCTCTGGTTTCCTGGCGGGCATTTCACGGCTGTGATTCTGCTGAGGAACTTCCCCGGGTGAGCCCCCGCTTCCTCCGAGCCTGGCACC 360
G  S  L  V  S  W  R  A  F  H  G  C  D  S  A  E  E  L  P  R  V  S  P  R  F  L  R  A  W  H

Smal

CCCCTCCCGTCTCAGCCAGGATGCCAACGAGGCGCTGGGCCCCGGCACCCAGTGTATCACCAAATGCGAGCACACCCGCCCCAAGCCAG 450
P  P  P  V  S  A  R  M  P  T  R  R  W  A  P  G  T  Q  C  I  T  K  C  E  H  T  R  P  K  P

Stul                  Kpnl

GGGAGCTGGCCTTCCGCAAGGGCGACGTGGTCACCATCCTGGAGGCCTGCGAGAACAAGAGCTGGTACCGGGTCAAGCACCACACCAGTG 540 SH 3
G  E  L  A  F  R  K  G  D  V  V  T  I  L  E  A  C  E  N  K  S  W  Y  R  V  K  H  H  T  S

Pvull

GACAGGAGGGGCTGCTGGCAGCTGGGGCGCTGCGGGAGCGGGAGGCCCTCTCCCAGACCCCAAGCTCAGCCTCATGCCGTGGTTCCACG 630
G  Q  E  G  L  L  A  A  G  A  L  R  E  R  E  A  L  S  A  D  P  K  L  S  L  M  P  W  F  H

PvullPstl

GGAAGATCTCGGGCCAGGAGGCTGTCCAGCAGCTGCAGCCTCCCGAGGATGGGCTGTTCCTGGTGCGGGAGTCGGCGCGCCACCCCGGCC 720
G  K  I  S  G  Q  E  A  V  Q  Q  L  Q  P  P  E  D  G  L  F  L  V  R  E  S  A  R  H  P  G        SH 2

Clal

ACTACGTCCTGTGCGTGAGCTTTGGCCGCGACGTCATCCACTACCGCGTGCTGCACCGCGACGGCCACCTCACAATCGATGAGGCCGTGT 810
D  Y  V  L  C  V  S  F  G  R  D  V  I  H  Y  R  V  L  H  R  D  G  H  L  T  I  D  E  A  V

TCTTCTGCAACCTCATGGACATGGTGGAGCATTACAGCAAGGACAAGGGCGCTATCTGCACCAAGCTGGTGAGACCAAAGCGGAAACACG 900
F  F  C  N  L  M  D  M  V  E  H  Y  S  K  D  K  G  A  I  C  T  K  L  V  R  P  K  R  K  H

FIG.1A

```
                                                     PstI
                                                      ⋮
GGACCAAGTCGGCCGAGGAGGAGCTGGCCACGGCCGGCTGGTTACTGAACCTGCAGCATTTGACATTGGGAGCACAGATCGGAGAGGGAG  990
 G  T  K  S  A  E  E  E  L  A  R  A  G  W  L  L  N  L |Q  H  L  T  L  G  A  Q  I  G  E  G
                                                       ─────────────────────────────────→

PSTI                                                          StuI
           ⋮                                                             ⋮
AGTTTGGAGCTGTCCTGCAGGGTGAGTACCTGGGGCAAAAGGTGGCCGTGAAGAATATCAAGTGTGATGTGACAGCCCAGGCCTTCCTGG  1080
 E  F  G  A  V  L  Q  G  E  Y  L  G  Q  K  V  A  V  K  N  I  K  C  D  V  T  A  Q  A  F  L           TK

ACGAGACGGCCGTCATGACGAAGATGCAACACGAGAACCTGGTGCGTCTCCTGGGCGTGATCCTGCACCAGGGGCTGTACATTGTCATGG  1170
 D  E  T  A  V  M  T  K  M  Q  H  E  N  L  V  R  L  L  G  V  I  L  H  Q  G  L  Y  I  V  M

SmaI                                  PstI
                                  ⋮                                     ⋮
AGCACGTGAGCAAGGGCAACCTGGTCAACTTTCTGCGGGACCCCGGGTCGAGCCCTCGTGAACACCGCTCAGCTCCTGCAGTTTTCTCTGC  1260
 E  H  V  S  K  G  N  L  V  N  F  L  R  T  R  G  R  A  L  V  N  T  A  Q  L  L  Q  F  S  L
                             HinDIII
                                ⋮
ACGTGGCCGAGGGCATGGAGTACCTGGAGAGCAAGAAGCTTGTGCACCGCGACCTGGCCGCCCCCAACATCCTGGTCTCAGAGGACCTGG  1350
 H  V  A  E  G  M  E  Y  L  E  S  K  K  L  V  H  R  D  L  A  A  R  N  I  L  V  S  E  D  L

TGGCCAAGGTCAGCGACTTTGGCCTGGCCAAAGCCGAGCGGAAGGGCCTAGACTCAAGCCGGCTGCCCGTCAAGTGGACGGCCCCCGAGG  1440
 V  A  K  Y  S  D  F  G  L  A  K  A  E  R  K  G  L  D  S  S  R  L  P  V  K  W  T  A  P  E

NdeI
                                                           ⋮
CTCTCAAACACGGGAAGTTCACCAGCAAGTCGGATGTCTGGAGTTTTGGGGTGCTGCTCTGGGAGGTCTTCTCATATGGACGGGCTCCGT  1530
 A  L  K  H  G  K  F  T  S  K  S  D  V  W  S  F  G  V  L  L  W  E  V  F  S  Y  G  R  A  P

KpnI
                              ⋮
ACCCTAAAATGTCACTGAAAGAGGTGTCGGAGGCCGTGGAGAAGGGGTACCGCATGGAACCCCCCGAGGGCTGTCCAGGCCCCGTGCACG  1620
 Y  P  K  M  S  L  K  E  V  S  E  A  V  E  K  G  Y  R  M  E  P  P  E  G  C  P  G  V  H

PvuII                                                          SmaI
         ⋮              |                                               ⋮
TCCTCATGAGCAGCTCCTGGGAGGCACAGAGCCCGCCCCCCCGGCCACCCTTCCGCAAACTGGCCCGAGAAGCTGGCCCCGGGAGCTACGCAGTG  1710
 Y  L  M  S  S  C  W  E  A  E  P |A  R  R  P  P  F  R  K  L  A  E  K  L |A  R  E  L  R  S
                                └─△─MATK─────────────────────────────────┘
```

FIG.1B

```
CAGGTGCCCCAGCCTCCGTCTCAGGGCAGGACGCCGACGGCTCCACCTCCCCCCGAAGCCAGGAGCCCTGACCCCACCCCGTGGGGCCCT  1800
 A  G  A  P  A  S  V  S  G  Q  D  A  D  G  S  T  S  P  R  S  Q  E  P

TGGCCCCAGAGGACCGAGAGAGTGGAGAGTGCGGCGTGGGGGCACTGACCAGGCCCAAGGAGGGTCCAGGCGGGCAAGTCATCCTCCTGG  1890

TGCCCACAGCAGGGCTGGCCCACGTAGGGGGCTCTGGGCGGCCCGTGGACACCCCAGACCTGCGAAGGATGATCGCCCGATAAAGACGG  1980

ATTCTAAGGACTCTAAAAAA  2000
```

FIG.1C

```
CCGCTTTTTGCTTAGAGCTTGAGAGTCAAAG   AGGACCCACATGTATACTTCGGCTCTAGCGAGT   AGGATGATAATATGGATACA  90
                                                                         M  D  T

AAATCTATTCTAGAAGAACTTCTTCTCAAAAGATCACAGCAAAAGAAGAAAATGTCACCAAATAATTACAAAGAACGGCTTTTTGTTTTG  180
 K  S  I  L  E  E  L  L  L  K  R  S  Q  Q  K  K  M  S  P  N  N  Y  K  E  R  L  F  V  L

ACCAAAACAAACCTTTCCTACTATGAATATGACAAAATGAAAAGGGGCAGCAGAAAAGGATCCATTGAAATTAAGAAAATCAGATGTGTG  270
 T  K  T  N  L  S  Y  Y  E  Y  D  K  M  K  R  G  S  R  K  G  S  I  E  I  K  K  I  R  C  V

GAGAAAGTAAATCTCGAGGAGCAGACGCCTGTAGAGAGACAGTACCCATTTCAGATTGTCTATAAAGATGGGCTTCTCTATGTCTATGCA  360
 E  K  V  N  L  E  E  Q  T  P  V  E  R  Q  Y  P  F  Q  I  V  Y  K  D  G  L  L  Y  V  Y  A     PH

TCAAATGAAGAGAGCCGAAGTCAGTGGTTGAAAGCATTACAAAAAGAGATAAGGGGTAACCCCCACCTGCTGGTCAAGTACCATAGTGGG  450
 S  N  E  E  S  R  S  Q  W  L  K  A  L  Q  K  E  I  R  G  N  P  H  L  L  V  K  Y  H  S  G

TTCTTCGTGGACGGGAAGTTCCTGTGTTGCCAGCAGAGCTGTAAAGCAGCCCCAGGATGTACCCTCTGGGAAGCATATGCTAATCTGCAT  540
 F  F  V  D  G  K  F  L  C  C  Q  Q  S  C  K  A  A  P  G  C  T  L  W  E  A  Y  A  N  L  H

ACTGCAGTCAATGAAGAGAAACACAGAGTTCCCACCTTCCCAGACAGAGTGCTGAAGATACCTCGGGCAGTTCCTGTTCTCAAAATGGAT  630
 T  A  V  N  E  E  K  H  R  V  P  T  F  P  D  R  V  L  K  I  P  R  A  V  P  V  L  K  M  D

GCACCATCTTCAAGTACCACTCTAGCCCAATATGACAACGAATCAAAGAAAAACTATGGCTCCCAGCCACCATCTTCAAGTACCAGTCTA  720
 A  P  S  S  S  T  T  L  A  Q  Y  D  N  E  S  K  K  N  Y  G  S  Q  P  P  S  S  S  T  S  L     SH3

GCCCAATATGACAGCAACTCAAAGAAAAATCTATGGCTCCCAGCCAAACTTCAACATGCAGTATATTCCAAGGGAAGACTTCCCTGACTGG  810
 A  Q  Y  D  S  N  S  K  K  I  Y  G  S  Q  P  N  F  N  M  Q  Y  I  P  R  E  D  F  P  D  W

TGGCAAGTAAGAAAACTGAAAAGTAGCAGCAGCAGTGAAGATGTTGCAAGCAGTAACCAAAAAGAAAGAAATGTGAATCACACCACCTCA  900
 W  Q  V  R  K  L  K  S  S  S  S  E  D  V  A  S  S  N  Q  K  E  R  N  V  N  H  T  T  S

AAGATTTCATGGGAATTCCCTGAGTCAAGTTCATCTGAAGAAGAGGAAAACCTGGATGATTATGACTGGTTTGCTGGTAACATCTCCAGA  990
 K  I  S  W  E  F  P  E  S  S  S  S  E  E  E  N  L  D  D  Y  D  W  F  A  G  N  I  S  R

TCACAATCTGAACAGTTACTCAGACAAAAGGGAAAAGAAGGAGCATTTATGGTTAGAAATTCGAGCCAAGTGGGAATGTACACAGTGTCC  1080
 S  Q  S  E  Q  L  L  R  Q  K  G  K  E  G  A  F  M  V  R  N  S  S  Q  V  G  M  Y  T  V  S     SH4

TTATTTAGTAAGGCTGTGAATGATAAAAAAGGAACTGTCAAACATTACCACGTGCATACAAATGCTGAGAACAAATTATACCTGGCAGAA  1170
 L  F  S  K  A  V  N  D  K  K  G  T  V  K  H  Y  H  V  H  T  N  A  E  N  K  L  Y  L  A  E
```

FIG.2A

```
AACTACTGTTTTGATTCCATTCCAAAGCTTATTCATTATCATCAACACAATTCAGCAGGCATGATCACACGGCTCCGCCACCCTGTGTCA  1260
  N  Y  C  F  D  S  I  P  K  L  I  H  Y  H  Q  H  N  S  A  G  M  I  T  R  L  R  H  P  V  S

ACAAAGGCCAACAAGGTCCCCGACTCTGTGTCCCTGGGAAATGGAATCTGGGAACTGAAAAGAGAAGAGATTACCTTGTTGAAGGAGCTG  1350
 T  K  A  N  K  V  P  D  S  V  S  L  G  N  G  I  W  E  L  K  R  E  E  I  T  L  L  K  E  L

GGAAGTGGCCAGTTTGGAGTGGTCCAGCTGGGCAAGTGGAAGGGGCAGTATGATGTTGCTGTTAAGATGATCAAGGAGGGCTCCATGTCA  1440
 G  S  G  Q  F  G  V  V  Q  L  G  K  W  K  G  Q  Y  D  V  A  V  K  M  I  K  E  G  S  M  S

GAAGATGAATTCTTTCAGGAGGCCCAGACTATGATGAAACTCAGCCATCCCAAGCTGGTTAAATTCTATGGAGTGTGTTCAAAGGAATAC  1530
 E  D  E  F  F  Q  E  A  Q  T  M  M  K  L  S  H  P  K  L  V  K  F  Y  G  V  C  S  K  E  Y

CCCATATACATAGTGACTGAATATATAAGCAATGGCTGCTTGCTGAATTACCTGAGGAGTCACGGAAAAGGACTTGAACCTTCCCAGCTC  1620  TK
 P  I  Y  I  V  T  E  Y  I  S  N  G  C  L  L  N  Y  L  R  S  H  G  K  G  L  E  P  S  Q  L

TTAGAAATGTGCTACGATGTCTGTGAAGGCATGGCCTTCTTGGAGAGTCACCAATTCATACACCGGGACTTGGCTGCTCGTAACTGCTTG  1710
 L  E  M  C  Y  D  V  C  E  G  M  A  F  L  E  S  H  Q  F  I  H  R  D  L  A  A  R  N  C  L

GTGGACAGAGATCTCTGTGTGAAAGTATCTGACTTTGGAATGACAAGGTATGTTCTTGATGACCAGTATGTCAGTTCAGTCGGAACAAAG  1800
 V  D  R  D  L  C  V  K  V  S  D  F  G  M  T  R  Y  V  L  D  D  Q  Y  V  S  S  V  G  T  K

TTTCCAGTCAAGTGGTCAGCTCCAGAGGTGTTTCATTACTTCAAATACAGCAGCAAGTCAGACGTATGGGCATTTGGGATCCTGATGTGG  1890
 F  P  V  K  W  S  A  P  E  V  F  H  Y  F  K  Y  S  S  K  S  D  V  W  A  F  G  I  L  M  W

GAGGTGTTCAGCCTGGGGAAGCAGCCCTATGACTTGTATGACAACTCCCAGGTGGTTCTGAAGGTCTCCCAGGGCCACAGGCTTTACCGG  1980
 E  V  F  S  L  G  K  Q  P  Y  D  L  Y  D  N  S  Q  V  V  L  K  V  S  Q  G  H  R  L  Y  R

CCCCACCTGGCATCGGACACCATCTACCAGATCATGTACAGCTGCTGGCACGAGCTTCCAGAAAAGCGTCCCACATTTCAGCAACTCCTG  2070
 P  H  L  A  S  D  T  I  Y  Q  I  M  Y  S  C  W  H  E  L  P  E  K  R  P  T  F  Q  Q  L  L

TCTTCCATTGAACCACTTCGGGAAAAAGACAAGCATTGAAGAAGAAATTAGGAGTGCTGATAAGAATGAATATAGATGCTGGCCAGCATT  2160
 S  S  I  E  P  L  R  E  K  D  K  H  .

TTCATTCATTTTAAGGAAAGTAGCAAGGCATAATGTAATTTAGCTAGTTTTTAATAGTGTTCTCTGTATTGTCTATTATTTAGAAATGAA  2250

CAAGGCAGGAAACAAAAGATTCCCTTGAAATTTAGGTCAAATTAGTAATTTTGTTTATGCTGCCCCTGATATAACACTTTCCAGCCTATA  2340

GCAGAAGCACATTTTCAGACTGCAATATAGAGACTGTGTTCATGTGTAAAGACTGAGCAGAACTGAAAAATTACTTATTGGATATTCATT  2430

CTTTTCTTTATATTGTCATTGTCACAACAATTAAATATACTACCAAGTACAAAAAAAAAAAAAAAAAAAAA  2500
```

FIG.2B

CCGGACTGGTCGAAAGACACGAACAGACTTGAAACAGGGGGAGAGCTCCTGGCGAAACGAAGACGTGGAGGTTTTACCAGGGATAAGAAG 90

AAAAGACACCTTCCTAGTGAGCAGCTGCCCAGCTCCTGCTCAGTTTTGCCTCGGGGTAGCACCTCCAGCCACAGAAAGCAAGCCGGTAAG 180

TCTCTCCAGGTAGGACTTGCTGCAACCCAGCTGCTGGACTGATCTGAAACGGGACTTTGCATACTCTCCGAAGTATGGTGAGTTGGTGCT 270
                                                                                                 M  V  S  W  C

GACTTCAAAGTTGCCTGGTGAAGGAAGATAAGGTGGATCGCAGAGACTAAGGGGAGAGGGAGAAGCCCTGCTCCTCTTCTCCCCACCAAG 360

GCACAATGAGCAACATCTGTCAGAGGCTCTGGGAGTACCTAGAACCCTATCTCCCCTGTTTGTCCACGGAGGCAGACAAGTCAACCGTGA 450
    M  S  N  I  C  Q  R  L  W  E  Y  L  E  P  Y  L  P  C  L  S  T  E  A  D  K  S  T  V

TTGAAAATCCAGGGGCGCTTTGCTCTCCCCAGTCACAGAGGCATGGCCACTACTTTGTGGCTTTGTTTGATTACCAGGCTCGGACTGCTG 540
 I  E  N  P  G  A  L  C  S  P  Q  S  Q  R  H  G  H  Y  F  V  A  L  F  D  Y  Q  A  R  T  A

AGGACTTGAGCTTCCGAGCAGGTGACAAACTTCAAGTTCTGGACACTTTGCATGAGGGCTGGTGGTTTGCCAGACACTTGGAGAAAAGAC 630  SH 3
 E  D  L  S  F  R  A  G  D  K  L  Q  V  L  D  T  L  H  E  G  W  W  F  A  R  H  L  E  K  R

GAGATGGCTCCAGTCAGCAACTACAAGGCTATATTCCTTCTAACTACGTGGCTGAGGACAGAAGCCTACAGGCAGAGCCGTGGTTCTTTG 720
 R  D  G  S  S  Q  Q  L  Q  G  Y  I  P  S  N  Y  V  A  E  D  R  S  L  Q  A  E  P  W  F  F

GAGCAATCGGAAGATCAGATGCAGAGAAACAACTATTATATTCAGAAAACAAGACCGGTTCCTTTCTAATCAGAGAAAGTGAAAGCCAAA 810
 G  A  I  G  R  S  D  A  E  K  Q  L  L  Y  S  E  N  K  T  G  S  F  L  I  R  E  S  E  S  Q        SH 2

AAGGAGAATTCTCTCTTTCAGTTTTAGATGGAGCAGTTGTAAAACACTACAGAATTAAAAGACTGGATGAAGGGGGATTTTTTCTCACGC 900
 K  G  E  F  S  L  S  V  L  D  G  A  V  V  K  H  Y  R  I  K  R  L  D  E  G  G  F  F  L  T

GAAGAAGAATCTTTTCAACACTGAACGAATTTGTGAGCCACTACACCAAGACAAGTGACGGCCTGTGTGTCAAGCTGGGGAAACCATGCT 990
 R  R  R  I  F  S  T  L  N  E  F  V  S  H  Y  T  K  T  S  D  G  L  C  V  K  L  G  K  P  C

TAAAGATCCAGGTCCCAGCTCCATTTGATTTGTCGTATAAAACCGTGGACCAATGGGAGATAGACCGCAACTCCATACAGCTTCTGAAGC 1080
 L  K  I  Q  V  P  A  P  F  D  L  S  Y  K  T  V  D  Q  W  E  I  D  R  N  S  I  Q  L  L  K

GATTGGGATCTGGTCAGTTTGCCAAGTATGGGAAGGTCTGTGGAACAATACCACTCCAGTAGCAGTGAAAACATTAAAACCAGGTTCAA 1170
 R  L  G  S  G  Q  F  G  E  V  W  E  G  L  W  N  N  T  T  P  V  A  V  K  T  L  K  P  G  S

TGGATCCAAATGACTTCCTGAGGGAGGCACAGATAATGAAGAACCTAAGACATCCAAAGCTTATCCAGCTTTATGCTGTTTGCACTTTAG 1260
 M  D  P  N  D  F  L  R  E  A  Q  I  M  K  N  L  R  H  P  K  L  I  Q  L  Y  A  V  C  T  L

FIG. 3A

|  |  | MKK1 | MKK2 |
|---|---|---|---|
| HUMAN | | | |
| MEG/ERYTH | MEG-01 | +++ | +++ |
|  | K562 | ++ | + |
|  | MO7E | ++ | + |
|  | HEL | +++ | ++ |
| MYELO/MAC | KG-1 | + | ++ |
|  | HL-60 | + | + |
|  | TF-1 | + | + |
| B-CELL | ALL-1 | − | + |
|  | RAJI | − | − |
|  | DAUDI | − | − |
| T-CELL | MOLT-3 | − | − |
|  | JURKAT | − | − |
| EPITHELIAL | HELA | − | − |
| RODENT | | | |
|  | BM | + | +++ |
|  | SPLEEN | +++ | + |
|  | THYMUS | − | − |
|  | LIVER | − | − |
|  | BRAIN | + | − |
| RAT NEURAL | P19 | + | − |

FIG.4

```
  1   MAGRGSLVSWRAFHGCDSAEELPRVSPRFL    MKK1 aa
  1   MSAIQAA-----------------------    hCSK (JH0559)

31   RAWHPPPVSARMPTRRWAPGTQCITKCEHT    MKK1 aa
  8   ---------------WPSGTECIAKYNFH    hCSK (JH0559)

61   RPKPGELAFRKGDVVTILEACENKSWYRVK    MKK1 aa
 22   GTAEQDLPFCKGDVLTIVAVTKDPNWYKAK    hCSK (JH0559)

91   HHTSGQEGLLAAGALREREALSADPKLSLM    MKK1 aa
 52   NKV-GREGIIPANYVQKREGVKAGTKLSLM    hCSK (JH0559)

121   PWFHGKISGQEAVQQLQPPEDGLFLVRESA    MKK1 aa
 81   PWFHGKITREQAERLLYPPETGLFLVREST    hCSK (JH0559)

151   RHPGDYVLCVSFGRDVIHYRVLHRDGHLTI    MKK1 aa
111   NYPGDYTLCVSCDGKVEHYRIMYHASKLSI    hCSK (JH0559)

181   DEAVFFCNLMDMVEHYSKDKGAICTKLVRP    MKK1 aa
141   DEEVYFENLMQLVEHYTSDADGLCTRLIKP    hCSK (JH0559)

211   KRKHGTKSAEEELARAGWLLNLQHLTLGAQ    MKK1 aa
171   KVMEGTVAAQDEFYRSGWALNMKELKLLQT    hCSK (JH0559)

241   IGEGEFGAVLQGEYLGQKVAVKNIKCDVTA    MKK1 aa
201   IGKGEFGDVMLGDYRGNKVAVKCIKNDATA    hCSK (JH0559)

271   QAFLDETAVMTKMQHENLVRLLGVILHQ--    MKK1 aa
231   QAFLAEASVMTQLRHSNLVQLLGVIVEEKG    hCSK (JH0559)

299   GLYIVMEHVSKGNLVNFLRTRGRALVNTAQ    MKK1 aa
261   GLYIVTEYMAKGSLVDYLRSRGRSVLGGDC    hCSK (JH0559)

329   LLQFSLHVAEGMEYLESKKLVHRDLAARNI    MKK1 aa
291   LLKFSLDVCEAMEYLEGNNFVHRDLAARNV    hCSK (JH0559)

359   LVSEDLVAKVSDFGLAKAERKGLDSSRLPV    MKK1 aa
321   LVSEDNVAKVSDFGLTKEASSTQDTGKLPV    hCSK (JH0559)
```

FIG.9A

```
389  K W T A P E A L K H G K F T S K S D V W S F G V L L W E V F        MKK1 aa
351  K W T A P E A L R E K K F S T K S D V W S F G I L L W E I Y        hCSK (JH0559)

419  S Y G R A P Y P K M S L K E V S E A V E K G Y R M E P P E G        MKK1 aa
381  S F G R V P Y P R I P L K D V V P R V E K G Y K M D A P D G        hCSK (JH0559)

449  C P G P V H V L M S S C W E A P A R R P P F R K L A E K L          MKK1 aa
411  C P P A V Y E V M K N C W H L D A M R P S F L Q L R E Q L          hCSK (JH0559)

479  A R E L R S A G A P A S V S G Q D A D G S T S P R S Q E P          MKK1 aa
441  E H - - - - - - - - - - I K T H E L H - - - - - - - - - L          hCSK (JH0559)
```

FIG. 9B

```
  1  M D T K S I L E E L L L K R S Q Q K K K M S P N N Y K E R L    MKK2 aa
  1  M A A - V I L E S I F L K R S Q Q K K K T S P L N F K K R L    hAtk (X58957)
  1  M N N F I L L E E Q L I K K S Q Q K R R T S P S N F K V R F    hTKT (L10717)
  1  M M V - - - - - - - - - - - - - - - - - - - - - - - - - -    mTec (X5663)

31  F V L T K T N L S Y Y E - - Y D K M K R G S R K G S I E I K    MKK2 aa
 30  F L L T V H K L S Y Y E Y D F E R G R R G S K K G S I D V E    hAtk (X58957)
 31  F V L T K A S L A Y F E D R - - H G K R T L K G S I E L S     hTKT (L10717)
  4  - - - - - - - - - - - - - - - - - - - - - - - - - - - -    mTec (X5663)

59  K I R C V E K V N L E E Q T P V E R Q - - - - - - - - - -    MKK2 aa
 60  K I T C V E T V V P E K N P P P E R Q I P R R G E E S S E M    hAtk (X58957)
 59  R I K C V E I V K S D - - - - - - - - - - - - - - - - -     hTKT (L10717)
  4  - - - - - - - - - - - - - - - - - - - - - - - - - - - -    mTec (X5663)

78  - - - - - - - - - Y P F Q I V Y K D G L L Y V Y A S N E E    MKK2 aa
 90  E Q I S I I E R F P Y P F Q V V Y D E G P L Y V F S P T E E    hAtk (X58957)
 70  - - I S I P C H Y K Y P F Q V V H D N Y L L Y V F A P D R E    hTKT (L10717)
  4  - - - - - - - - - S F P V K I N F H S S P - - - - - - - Q    mTec (X5663)

98  S R S Q W L K A L Q K E I R G N P H L L V K Y H S G F F V D    MKK2 aa
120  L R K R W I H Q L K N V I R Y N S D L V Q K Y H P C F W I D    hAtk (X58957)
 98  S R Q R W V L A L K E E T R N N S L V P K Y H P N F W M D    hTKT (L10717)
 17  S R D R W V K L K E E I K N N N I M I K Y H P K F W A D    mTec (X5663)

128  G K F L C C Q Q S C K A A P G C T L W E A Y A N L H T A V N    MKK2 aa
150  G Q Y L C C S Q T A K N A M G C Q I L E N R N G S L K P G S    hAtk (X58957)
128  G K W R C C S Q L E K L A T G C A Q Y D - - - - - - - - P    hTKT (L10717)
 47  G S Y Q C C R Q T E K L A P G C E K Y N L F E S S I - - - -    mTec (X5663)

158  E E K H R V P T F P D R V L K I P R A V P V L K M D A P S S    MKK2 aa
180  S H R K T K K P L P P - - - - T P E E D Q I L K K P L P P E    hAtk (X58957)
149  T K N A S K K P L P P - - - - T P E D N R - - - - - - - -    hTKT (L10717)
 73  - - - - - R K T L P P - - - - A P E - - - - I K K R R P P -    mTec (X5663)

188  S T T L A Q Y D N E S K K N Y G S Q P P S S S T S L A Q Y D    MKK2 aa
206  P A A A P V S T S E L K K - - - - - - - - - - - V V A L Y D    hAtk (X58957)
166  - - - R P L W E P E E T V - - - - - - - - - - - V I A L Y D    hTKT (L10717)
 89  P P I P P E E E N T E E I - - - - - - - - - - - V V A M Y D    mTEC (X5663)
```

FIG.10A

```
218  S N S K K I Y G S Q P N F N M Q Y I P R E D F P - D W W Q V    MKK2    aa
225  Y M P M N A N D L Q L R K G D E Y F I L E E S N L P W W R A    hAtk    (X58957)
182  Y Q T N D P Q E L A L R R N E E Y C L L D S S E I H W W R V    hTKT    (L10717)
108  F Q A T E A H D L R L E R G Q E Y I I L E K N D L H W W R A    mTec    (X5663)

247  R K L K S S S S S E D V A S S N Q K E R N V N H T T S K I S    MKK2    aa
255  R D - - K N G Q E G Y I P S N Y V T E - A - - - - - - - - -    hAtk    (X58957)
212  Q D - - R N G H E G Y V P S S Y L V E K S - - - - - - - - -    hTKT    (L10717)
138  R D - - K - - - - - - - - - - - - - - - - - - - - - - - - -   mTec    (X5663)

277  W E F P E S S S S E E E N L D D Y D W F A G N I S R S Q S      MKK2    aa
273  - - - - - - - - - - E D S I E M Y E W Y S K H M T R S Q A      hAtk    (X58957)
231  - - - - - - - - - - P N N L E T Y E W Y N K S I S R D K A      hTKT    (L10717)
141  - - - - - - - - - - - - - - Y G W Y C R N T N R S K A          mTec    (X5663)

307  E Q L L R Q K G K E G A F M V R N S S Q V G M Y T V S L F S    MKK2    aa
292  E Q L L K Q E G K E G G F I V R D S S K A G K Y T V S V F A    hAtk    (X58957)
250  E K L L L D T G K E G A F M V R D S R T A G T Y T V S V F T    hTKT    (L10717)
154  E Q L L R T E D K E G G F M V R D S S Q P G L Y T V S L Y T    mTec    (X5663)

337  K - A V N D K K G T V K H Y H V H - - T N A E N K L Y L A E    MKK2    aa
322  K S T - G D P Q G V T R H Y V V - - C S T P Q S Q Y Y L A E    hAtk    (X58957)
280  K A V V S E N N P C I K H Y H I K E T N D N P K R Y Y V A E    hTKT    (L10717)
184  K F G - G E G S S G F R H Y H I K E T A T S P K K Y Y L A E    mTec    (X5663)

364  N Y C F D S I P K L I H Y H Q H N S A G M I T R L R H P V S    MKK3    aa
349  K H L F S T I P E L I N Y H Q H N S A G L I S R L K Y P V S    hAtk    (X58957)
310  K Y V F D S I P L L I N Y H Q H N G G G L V T R L R Y P V C    hTKT    (L10717)
213  K H A F G S I P E T L E Y H K H N A A G L V T R L R Y P V S    mTec    (X5663)

394  T K A N K V P D S V S L G N G I W E L K R E E I T L L K E L    MKK2    aa
379  Q Q N K N A P S T A G L G Y G S W E I D P K D L T F L K E L    hAtk    (X58957)
340  F G R Q K A P V T A G L R Y G K W V I D P S E L T F V Q E I    hTKT    (L10717)
243  T K G K N A P T T A G F S Y D K W E I N P S E L T F M R E L    mTec    (X5663)

424  G S G Q F G V V Q L G K W K G Q Y D V A V K M I K E G S M S    MKK2    aa
409  G T G Q F G V V K Y G K W R G Q Y D V A I K M I K E G S M S    hAtk    (X58957)
370  G S G Q F G L V H L G Y W L N K D K V A I K T I R E G A M S    hTKT    (L10717)
273  G S G L F G V V R L G K W R A Q Y K V A I K A I R E G A M C    mTec    (X5663)
```

FIG.10B

```
454  E D E F Q E A Q T M M K L S H P K L V K F Y G V C S K E Y    MKK2    aa
439  E D E F I E E A K V M M N L S H E K L V Q L Y G V C T K Q R  hAtk    (X58957)
400  E E D F I E E A E V M M K L S H P K L V Q L Y G V C L E Q A  hTKT    (L10717)
303  E E D F I E E A K V M M K L T H P K L V Q L Y G V C T Q Q K  mTec    (X5663)

484  P I Y I V T E Y I S N G C L L N Y L R S H G K G L E P S Q L  MKK2    aa
469  P I F I I T E Y M A N G C L L N Y L R E M R H R F Q T Q Q L  hAtk    (X58957)
430  P I C L V F E F M E H G C L S D Y L R T Q R G L F A A E T L  hTKT    (L10717)
333  P I Y I V T E F M E R G C L L N F L R Q R Q G H F S R D M L  mTec    (X5663)

514  L E M C Y D V C E G M A F L E S H Q F I H R D L A A R N C L  MKK2    aa
499  L E M C K D V C E A M E Y L E S K Q F L H R D L A A R N C L  hAtk    (X58957)
460  L G M C L D V C E G M A Y L E E A C V I H R D L A A R N C L  hTKT    (L10717)
363  L S M C Q D V C E G M E Y L E R N S F I H R D L A A R N C L  mTec    (X5663)

544  V D R D L C V K V S D F G M T R Y V L D D Q Y V S S V G T K  MKK2    aa
529  V N D Q G V V K V S D F G L S R Y V L D D E Y T S S V G S K  hAtk    (X58957)
490  V G E N Q V I K V S D F G M T R F V L D D Q Y T S S T G T K  hTKT    (L10717)
393  V N E A G V V K V S D F G M A R Y V L D D Q Y T S S S G A K  mTec    (X5663)

574  F P V K W S A P E V F H Y F K Y S S K S D V W A F G I L M W  MKK2    aa
559  F P V R W S P P E V L M Y S K F S S K S D I W A F G V L M W  hAtk    (X58957)
520  F P V K W A S P E V F S F S R Y S S K S D V W S F G V L M W  hTKT    (L10717)
423  F P V K W C P P E V F N Y S R F S S K S D V W S F G V L M W  mTec    (X5663)

604  E V F S L G K Q P Y D L Y D N S Q V V L K V S Q G H R L Y R  MKK2    aa
589  E I Y S L G K M P Y E R F T N S E T A E H I A Q G L R L Y R  hAtk    (X58957)
550  E V F S E G K I P Y E N R S N S E V V E D I S T G F R L Y K  hTKT    (L10717)
453  E T F T E G R M P F E K N T N Y E V V T M V T R G H R L H R  mTec    (X5663)

634  P H L A S D T I Y Q I M Y S C W H E L P E K R P T F Q Q L L  MKK2    aa
619  P H L A S E K V Y T I M Y S C W H E K A D E R P T F K I L L  hAtk    (X58957)
580  P R L A S T H V Y Q I M N H C W K E R P E D R P A F S R L L  hTKT    (L10717)
483  P K L A T K Y L Y E V M L R C W Q E R P E G R P S F E D L L  mTec    (X5663)

664  S S I E P L R E K D K H                                     MKK2    aa
649  S N I L D V M D E E S                                       hAtk    (X58957)
610  R Q L A E I A E S - - - - G L                               hTKT    (L10717)
513  R T I D E L V E C E E T F G R                               mTec    (X5663)
```

FIG.10C

```
1   M S N I C Q R L W E - - - - - - - - - - - - - - - -   MKK3 MPI aa
1   M G C V Q C K D K E A - T - - - K L T E E R D G S L N Q - S   hFyn
1   M G C V H C K E K I S - G - - - K G Q G G S G T G T P A - H   cYrk
1   M G S N K S K P K D A - S Q R - R R S L E P A E N V H G - A   hSrc
1   M G C I K S K E N K S - P A I - K Y R P E N T P E P V S - T   hYes
1   M G C V F C K K L E P - V A T A K E D A G L E G D F R S Y G   hFgr
1   M G C I K S K G K D S L S D D G V D L - K T Q P V R N T E R   hLyn
1   M G S M K S K - - - F L Q V G G N T F S K T E T S A S P H C   hHck
1   M G C G C S S - - - - - H P E D D W M E N I D V C E N C H Y   hLck
1   M G L L S K R Q V S E K G K G W S P V K I R T Q D K A P P   mBlk

11  - - - - - - - - - - - - - - - - - - - - - - - - Y L E P   MKK3 MPI aa
26  S G Y R Y G T D P T P Q H Y P S F G V T S I P N - - Y N N F   hFyn
26  P P S Q Y D P D P T - Q L S G A F - - T H I P D - - F N N F   cYrk
28  G G A F P A S Q T P S K P A S A D G H R G P S A A F A P A   hSrc
28  S V S H Y G A E P T T V S P C P S S A K G T A V N F S S L   hYes
30  A A D H Y G P D P T K A R P A S - S F A H I P N - - Y S N F   hFgr
30  T I Y V R D P T S N K Q Q R P V P E S Q L L P G Q R F Q T K   hLyn
28  P V Y V P D P T S T I K P G P N S H N S N T P G I R - - - -   hHck
26  P I V P L D G K G T L L I R N G S E V R D - P L V T Y E G S   hLck
31  P L P P L V V F N H L A P P S P N Q - - - - - - - - - - -   mBlk

15  Y L P C L S T E A D K S T V I E N P G A L C S P Q S Q R H G   MKK3 MPI aa
54  H A A - - - G G Q G L T V F G G V N - - S S S H T G T L R T   hFyn
51  H A A - - - A V S P P V P F S G P G F Y P C N T L Q A H S S   cYrk
58  A A E P - - - - - - - - K L F G G F N S S D T V T S P Q R A G   hSrc
58  S M T P F G G S S G V T P F G G A S S S F S V V P S S Y P A   hYes
57  S S Q A I N P G - - - - - F - - - - - - - - - L D S G T I R G   hFgr
60  D P E E - - - - - - - - - - - Q G - - - - - - - - - - - - -   hLyn
54  E A G S - - - - - - - - - - E D - - - - - - - - - - - - -   hHck
55  N P P A - - - - - - - S P L Q D - - - - - - - - - - - - -   hLck
49  D P D E - - - - - - - - - - E E - - - - - - - - - - - - -   mBlk

45  H - - - - - - - Y F V A L F D Y Q A R T A E D L S F R A G D K   MKK3 MPI aa
79  R G G T G V T L F V A L Y D Y E A R T E D D L S F H K G E K   hFyn
78  I T G G V T L F I A L Y D Y E A R T E D D L S F Q K G E K   cYrk
81  P L A G V T T F V A L Y D Y E S R T E T D L S F K K G E R   hSrc
88  G L T G V T I F V A L Y D Y E A R T T E D L S F K K G E R   hYes
74  V S G I G V T L F I A L Y D Y E A R T E D D L T F T K G E K   hFgr
66  - - - - - - D I V V A L Y P Y D G I H P D D L S F K K G E K   hLyn
60  - - - - - - I I V A L Y D Y E A I H H E D L S F Q K G D Q   hHck
64  - - - - - - N L V I A L H S Y E P S H D G D L G F E K G E Q   hLck
55  - - - - - - R F V V A L F D Y A A V N D R D L Q V L K G E K   mBlk
```

FIG.11A

```
 69  L Q V L D T L H E G W W F A R H L E K R R D G S S Q Q L Q G   MKK3 MPI  aa
109  F Q T L N S S E G D W W E A R S L T T G E T G - - - - - -   hFyn
108  F H I I N N T E G D W W E A R S L S S G A T G - - - - - -   cYrk
111  L Q I V N N T E G D W W L A H S L S T G Q T G - - - - - -   hSrc
118  F Q I I N N T E G D W W E A R S I A I G K N G - - - - - -   hYes
104  F H I L N N T E G D W W E A R S L S S G K T G - - - - - -   hFgr
 90  M K V L E E H - G E W W K A K S L L T K K E G - - - - - -   hLyn
 84  M V V L E E S - G E W W K A R S L A T R K E G - - - - - -   hHck
 88  L R I L E Q S - G E W W K A Q S L T T G Q E G - - - - - -   hLck
 79  L Q V L R S T - G D W W L A R S L V T G R E G - - - - - -   mBlk

99  Y I P S N Y V A E D R S L Q A E P W F F G A I G R S D A E K   MKK3 MPI  aa
132  Y I P S N Y V A P V D S I Q A E E W Y F G K L G R K D A E R   hFyn
131  Y I P S N Y V A P V D S I Q A E E W Y F G K I G R K D A E R   cYrk
134  Y I P S N Y V A P S D S I Q A E E W Y F G K I T R R E S E R   hSrc
141  Y I P S N Y V A P A D S I Q A E E W Y F G K M G R K D A E R   hYes
127  C I P S N Y V A P V D S I Q A E E W Y F G K I G R K D A E R   hFgr
112  F I P S N Y V A K L N T L E T E E W F F K D I T R K D A E R   hLyn
106  Y I P S N Y V A R V D S L E T E E W F F K G I S R K D A E R   hHck
110  F I P F N F V A K A N S L E P E P W F F K N L S R K D A E R   hLck
101  Y V P S N F V A P V E T L E V E K W F F R T I S R K D A E R   mBlk

129  Q L L Y S E N K T G S F L I R E S E S Q K G E F S L S V L D   MKK3 MPI  aa
162  Q L L S F G N P R G T F L I R E S E T T K G A Y S L S I R D   hFyn
161  Q L L C H G N C R G T F L I R E S E T T K G A Y S L S I R D   cYrk
164  L L L N A E N P R G T F L V R E S E T T K G A Y C L S V S D   hSrc
171  L L L N P G N Q R G I F L V R E S E T T K G A Y S L S I R D   hYes
157  Q L L S P G N P Q G A F L I R E S E T T K G A Y S L S I R D   hLyn
142  Q L L A P G N S A G A F L I R E S E T L K G S F S L S V R D   hHck
136  Q L L A P G N M L G S F M I R D S E T T K G S Y S L S V R D   hHck
140  Q L L A P G N T H G S F L I R E S E S T A G S F S L S V R D   hLck
131  Q L L A P M N K A G S F L I R E S E S N K G A F S L S V K D   mBlk

159  - - - - - G A V V K H Y R I K R L D E G G F F L T R R R I F   MKK3 MPI  aa
192  W D D M K G D H V K H Y K I R K L D N G G Y Y I T T R A Q F   hFyn
191  W D E A K G D H V K H Y K I R K L D S G G Y Y I T T R A Q F   cYrk
194  F D N A K G L N V K H Y K I R K L D S G G F Y I T S R T Q F   hSrc
201  W D E I R G D N V K H Y K I R K L D N G G Y Y I T T R A Q F   hYes
187  W D Q T R G D H V K H Y K I R K L D M G G Y Y I T T R V Q F   hFgr
172  F D P V H G D V I K H Y K I R S L D N G G Y Y I S P R I T F   hLyn
166  Y D P R Q G D T V K H Y K I R T L D N G G F Y I S P R S T F   hHck
170  F D Q N Q G E V V K H Y K I R N L D N G G F Y I S P R I T F   hLck
161  I T T - Q G E V V K H Y K I R S L D N G G Y Y I S P R I T F   mBlk
```

FIG.11B

```
184  S T L N E F V S H Y T K T S D G L C V K L G K P C L K I Q V   MKK3 MPI  aa
222  E T L Q Q L V Q H Y S E R A A G L C R L V P C H K G M -       hFyn
221  D T I Q Q L V Q H Y I E R A A G L C R L A V P C P K G T -     cYrk
224  N S L Q Q L V A Y Y S K H A D G L C H R L T T V C P T S K -   hSrc
231  D T L Q K L V K H Y T E H A D G L C H K L T T V C P T V K -   hYes
217  N S V Q E L V Q H Y M E V N D G L C N L L I A P C T I M K -   hFgr
202  P C I S D M I K H Y Q K Q A D G L C R R L E K A C I S P K -   hLyn
196  S T L Q E L V D H Y K K G N D G L C Q K L S V P C M S S K -   hHck
200  P G L H E L V R H Y T N A S D G L C T R L S R P C Q T Q K -   hLck
190  P T L Q A L V Q H Y S K K G D G L C Q K L T L P C V N L A -   mBlk

214  P A P F D L S Y K T V D Q W E I D R N S I Q L L K R L G S G   MKK3 MPI  aa
251  P R L T D L S V K T K D V W E I P R E S L Q L I K R L G N G   hFyn
250  P K L A D L S V K T K D V W E I P R E S L Q L L Q K L G N G   cYrk
253  P Q T Q G L A - - - K D A W E I P R E S L R L E V K L G Q G   hSrc
260  P Q T Q G L A - - - K D A W E I P R E S L R L E V K L G Q G   hYes
246  P Q T L G L A - - - K D A W E I S R S S I T L E R R L G T G   hFgr
231  P Q - - - - K P W D K D A W E I P R E S I K L V K R L G A G   hLyn
225  P Q - - - - K P W E K D A W E I P R E S L K L E K K L G A G   hHck
229  P Q - - - - K P W W E D E W E V P R E T L K L V E R L G A G   hLck
219  P K - - - - N L W A Q D E W E I P R Q S L K L V R K L G S G   mBlk

244  Q F G E V W E G L W N N T T P V A V K T L K P G S M D P N D   MKK3 MPI  aa
281  Q F G E V W M G T W N G N T K V A I K T L K P G T M S P E S   hFyn
280  Q F G E V W M G T W N G T T K V A V K T L K P G T M S P E A   cYrk
280  C F G E V W M G T W N G T T R V A I K T L K P G T M S P E A   hSrc
287  C F G E V W M G T W N G T T K V A I K T L K P G T M M P E A   hYES
273  C F G D V W L G T W N G S T K V A V K T L K P G T M S P K A   hFgr
257  Q F G E V W M G Y Y N S T K V A V K T L K P G T M S V Q A   hLyn
251  Q F G E V W M A T Y N K H T K V A V K T M K P G S M S V E A   hHck
255  Q F G E V W M G Y Y N G H T K V A V K S L K Q G S M S P D A   hLck
245  Q F G E V W M G Y Y K N N M K V A I K T L K E G T M S P E A   mBlk

274  F L R E A Q I M K N L R H P K L I Q L Y A V C T L E D P I Y   MKK3 MPI  aa
311  F L E E A Q I M K K L K H D K L V Q L Y A V V S - E E P I Y   hFyn
310  F L E E A Q I M K R L R H D K L V Q L Y A V V S - E E P I Y   cYrk
310  F L Q E A Q V M K K L R H E K L V Q L Y A V V S - E E P I Y   hSrc
317  F L Q E A Q I M K K L R H D K L V P L Y A V V S - E E P I Y   hYes
303  F L E E A Q V M K L L R H D K L V Q L Y A V V S - E E P I Y   hFgr
287  F L E E A N L M K T L Q H D K L V R L Y A V V T R E E P I Y   hLyn
281  F L A E A N V M K T L Q H D K L V K L H A V V T K E - P I Y   hHck
285  F L A E A N L M K Q L Q H Q R L V R L Y A V V T - Q E P I Y   hLck
275  F L G E A N V M K T L Q H E R L V R L Y A V V T R E - P I Y   mBlk
```

FIG.11C

```
304  I I T E L M R H G S L Q E Y L Q N D T G S K I H L T Q Q V D    MKK3 MPI  aa
340  I V T E Y M N K G S L L D F L K D G E G R A L K L P N L V D    hFyn
339  I V T E F M S Q G S L L D F L K D G D G R Y L K L P Q L V D    cYrk
339  I V T E Y M S K G S L L D F L K G E T G K Y L R L P Q L V D    hSrc
346  I V T E F M S K G S L L D F L K E G D G K Y L K L P Q L V D    hYes
332  I V T E F M C H G S L L D F L K N P E G Q D L R L P Q L V D    hFgr
317  I I T E Y M A K G S L L D F L K S D E G G K V L L P K L I D    hLyn
310  I I T E F M A K G S L L D F L K S D E G S K Q P L P K L I D    hHck
314  I I T E Y M E N G S L V D F L K T P S G I K L T I N K L L D    hLck
304  I V T E Y M A R G C L L D F L K T D E G S R L S L P R L I D    mBlk

334  M A A Q V A S G M A Y L E S R N Y I H R D L A A R N V L V G    MKK3 MPI  aa
370  M A A Q V A A G M A Y I E R M N U I H R D L R S A N I L V G    hFyn
369  M A A Q I A A G M A Y I E R M N Y I H R D L R A A N I L V G    cYrk
369  M A A Q I A S G M A Y V E R M N Y V H R D L R A A N I L V G    hSrc
376  M A A Q I A D G M A Y I E R M N Y I H R D L R A A N I L V G    hYes
362  M A A Q V A E G M A Y M E R M N Y I H R D L R A A N I L V G    hFgr
347  F S A Q I A E G M A Y I E R K N Y I H R D L R A A N V L V S    hLyn
340  F S A Q I A E G M A F I E Q R N Y I H R D L R A A N I L V S    hHck
344  M A A Q I A E G M A F I E E R N Y I H R D L R A A N I L V S    hLck
334  M S A Q V A E G M A Y I E R M N S I H R D L R A A N I L V S    mBlk

364  E H N I Y K V A D F G L A R V F K V D N E D I Y E S R H E I    MKK3 MPI  aa
400  N G L I C K I A D F G L A R L I - - - E D N E Y T A R Q G A    hFyn
399  D N L V C K I A D F G L A R L I - - - E D N E Y T A R Q G A    cYrk
399  E N L V C K V A D F G L A R L I - - - E D N E Y T A R Q G A    hSrc
406  E N L V C K I A D F G L A R L I - - - E D N E Y T A R Q G A    hYes
392  E R L A C K I A D F G L A R L I - - - K D D E Y N P C Q G S    hFgr
377  E S L M C K I A D F G L A R V I - - - E D N E Y T A R E G A    hLyn
370  A S L V C K I A D F G L A R V I - - - E D N E Y T A R E G A    hHck
374  D T L S C K I A D F G L A R L I - - - E D N E Y T A R E G A    hLck
364  E T L C C K I A D F G L A R I I - - - D S E Y T A Q E G A    mBlk

394  K L P V K W T A P E A I R S N K F S I K S D V W S F G I L L    MKK3 MPI  aa
427  K F P I K W T A P E A A L Y G R F T I K S D V W S F G I L L    hFyn
426  K F P I K W T A P E A A L F G K F T I K S D V W S F G I L L    cYrk
426  K F P I K W T A P E A A L Y G R F T I K S D V W S F G I L L    hSrc
433  K F P I K W T A P E A A L Y G R F T I K S D V W S F G I L Q    hYes
419  K F P I K W T A P E A A L F G R F T I K S D V W S F G I L L    hFgr
404  K F P I K W T A P E A I N F G C F T I K S D V W S F G I L L    hLyn
397  K F P I K W T A P E A I N F G S F T I K S D V W S F G I L L    hHck
401  K F P I K W T A P E A I N Y G T F T I K S D V W S F G I L L    hLck
390  K F P I K W T A P E A I H F G V F T I K A D V W S F G V L L    mBlk
```

FIG.11D

```
424  Y E I I T Y G K M P Y S G M T G A Q V I Q M L A Q N Y R L P    MKK3 MPI  aa
457  T E L V T K G R V P Y P G M N N R E V L E Q V E R G Y R M P    hFyn
456  T E L V T K G R V P Y P G M N N R E V L E Q V E R G Y R M Q    cYrk
456  T E L T T K G R V P Y P G M V N R E V L D Q V E R G Y R M P    hSrc
463  T E L V T K G R V P Y P G M V N R E V L E Q V E R G Y R M P    hYes
449  T E L I T K G R I P Y P G M N K R E V L E Q V E Q G Y H M P    hFgr
434  Y E I V T Y G K I P Y P G R T N A D V M T A L S Q G Y R M P    hLyn
427  M E I V T Y G R I P Y P G M S N P E V I R A L E R G Y R M P    hHck
431  T E I V T H G R I P Y P G M T N P E V I Q N L E R G Y R M V    hLck
420  M V I V T Y G R V P Y P G M S N P E V I R S L E H G Y R M P    mBlk

454  Q P S N C P Q Q F Y N - I M L E C W N A E P K E R P T F E T    MKK3 MPI  aa
487  C P Q D C P I S L H - E L M I H C W K K D P E E R P T F E Y    hFyn
486  C P G G C P P S L H - D V M V Q C W K R E P E E R P T F E Y    cYrk
486  C P E C P E S L H - D L M C Q C W R K E P E E R P T F E Y     hSrc
493  C P Q G C P E S L H - E L M N L C W K K D P D E R P T F E Y    hYes
479  C P P G C P A S L Y - E A M E Q T W R L D P E E R P T F E Y    hFgr
464  R V E N C P D E L Y - D I M K M C W K E K A E E R P T F D Y    hLyn
457  R P E N C P E E L Y - N I M M R C W K N R P E E R P T F E Y    hHck
461  R P D N C P E E L Y - Q L M R L C W K E R P E D R P T F D Y    hLck
450  C P E T C P P E L Y N D I I T E C W R G R P E E R P T F E F    mBlk

483  L R W K L E D Y F E - T D S S Y S D A N N F I R                MKK3 MPI  aa
516  L Q S F L E D Y F T A T E P Q Y Q P G E N - - - L              hFyn
515  L Q S F L E D Y F T A T E P Q Y Q P G D N - - - Q              cYrk
515  L Q A F L E D Y F T S T E P Q Y Q P G E N - - - L              hSrc
522  I Q S F L E D Y F T A T E P Q Y Q P G E N - - - L              hYes
508  L Q S F L E D Y F T S A E P Q Y Q P G D Q - - - T              hFgr
493  L Q S V L D D F Y T A T E G Q Y Q Q - - Q - - - P              hLyn
486  I Q S V L D D F Y T A T E S Q Y Q Q - - Q - - - P              hHck
490  L R S V L E D F F T A T E G Q Y Q P - - Q - - - P              hLck
480  L Q S V L E D F Y T A T E G Q Y E L - - Q - - - P              mBlk
```

FIG.11E

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 2000 base pairs
      (B) TYPE: nucleic acid
      (C) STRANDEDNESS: unknown
      (D) TOPOLOGY: unknown (xi) SEQUENCE DESCRIPTION: SEQ ID NO:1:

```
CTCGCTCCAA GTTGTGCAGC CGGGACCGCC TCGGGGTGTG CAGCCGGCTC GCGGAGGCCC        60
TCCTGGGGGC GGGCGCGGGG CGGCTCGGGG GCGCCCCCTG AGCAGAAAAC AGGAAGAACC       120
AGGCTCGGTC CAGTGGCACC CAGCTCCCTA CCTCCTGTGC CAGCCGCCTG GCCTGTGGCA       180
GGCCATTCCC AGCGTCCCCG ACTGTGACCA CTTGCTCAGT GTGCCTCTCA CCTGCCTCAG       240
TTTCCCTCTG GGGGGCGATG GCGGGGCGAG GCTCTCTGGT TTCCTGGCGG GCATTTCACG       300
GCTGTGATTC TGCTGAGGAA CTTCCCCGGG TGAGCCCCCG CTTCCTCCGA GCCTGGCACC       360
CCCCTCCCGT CTCAGCCAGG ATGCCAACGA GGCGCTGGGC CCCGGGCACC CAGTGTATCA       420
CCAAATGCGA GCACACCCGC CCCAAGCCAG GGAGCTGGCC CTTCCGCAAG GGCGACGTGG       480
TCACCATCCT GGAGGCCTGC GAGAACAAGA GCTGGTACCG CGTCAAGCAC CACACCAGTG       540
GACAGGAGGG GCTGCTGGCA GCTGGGGCGC TGCGGGAGCG GGAGGCCCTC TCCGCAGACC       600
CCAAGCTCAG CCTCATGCCG TGGTTCCACG GGAAGATCTC GGGCCAGGAG GCTGTCCAGC       660
AGCTGCAGCC TCCCGAGGAT GGGCTGTTCC TGGTGCGGGA GTCCGCGCGC CACCCCGGCG       720
ACTACGTCCT GTGCGTGAGC TTTGGCCGCG ACGTCATCCA CTACCGCGTG CTGCACCGCG       780
ACGGCCACCT CACAATCGAT GAGGCCGTGT TCTTCTGCAA CCTCATGGAC ATGGTGGAGC       840
ATTACAGCAA GGACAAGGGC GCTATCTGCA CCAAGCTGGT GAGACCAAAG CGGAAACACG       900
GGACCAAGTC GGCCGAGGAG GAGCTGGCCA GGGCGGGCTG GTTACTGAAC CTGCAGCATT       960
TGACATTGGG AGCACAGATC GGAGAGGGAG AGTTTGGAGC TGTCCTGCAG GGTGAGTACC      1020
TGGGGCAAAA GGTGGCCGTG AAGAATATCA AGTGTGATGT GACAGCCCAG GCCTTCCTGG      1080
ACGAGACGGC CGTCATGACG AAGATGCAAC ACGAGAACCT GGTGCGTCTC CTGGGCGTGA      1140
TCCTGCACCA GGGGCTGTAC ATTGTCATGG AGCACGTGAG CAAGGGCAAC CTGGTGAACT      1200
TTCTGCGGAC CCGGGGTCGA GCCCTCGTGA ACACCGCTCA GCTCCTGCAG TTTTCTCTGC      1260
ACGTGGCCGA GGGCATGGAG TACCTGGAGA GCAAGAAGCT TGTGCACCGC GACCTGGCCG      1320
CCCGCAACAT CCTGGTCTCA GAGGACCTGG TGGCCAAGGT CAGCGACTTT GGCCTGGCCA      1380
AAGCCGAGCG GAAGGGGCTA GACTCAAGCC GGCTGCCCGT CAAGTGGACG CGCCCCGAGG      1440
CTCTCAAACA CGGGAAGTTC ACCAGCAAGT CGGATGTCTG GAGTTTTGGG GTGCTGCTCT      1500
GGGAGGTCTT CTCATATGGA CGGGCTCCGT ACCCTAAAAT GTCACTGAAA GAGGTGTCGG      1560
AGGCCGTGGA GAAGGGGTAC CGCATGGAAC CCCCCGAGGG CTGTCCAGGC CCCGTGCACG      1620
TCCTCATGAG CAGCTGCTGG GAGGCAGAGC CCGCCCGCCG GCCACCCTTC CGCAAACTGG      1680
CCGAGAAGCT GGCCCGGGAG CTACGCAGTG CAGGTGCCCC AGCCTCCGTC TCAGGGCAGG      1740
ACGCCGACGG CTCCACCTCG CCCCGAAGCC AGGAGCCCTG ACCCCACCCG GTGGGGCCCT      1800
TGGCCCCAGA GGACCGAGAG AGTGGAGAGT GCGGCGTGGG GGCACTGACC AGGCCCAAGG      1860
AGGGTCCAGG CGGGCAAGTC ATCCTCCTGG TGCCCACAGC AGGGGCTGGC CCACGTAGGG      1920
GGCTCTGGGC GGCCCGTGGA CACCCCAGAC CTGCGAAGGA TGATCGCCCG ATAAAGACGG      1980
ATTCTAAGGA CTCTAAAAAA                                                 2000
```

(2) INFORMATION FOR SEQ ID NO:2:

(i) SEQUENCE CHARACTERISTICS:
        (A) LENGTH: 507 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:2:

```
Met Ala Gly Arg Gly Ser Leu Val Ser Trp Arg Ala Phe His Gly Cys
 1               5                  10                  15

Asp Ser Ala Glu Glu Leu Pro Arg Val Ser Pro Arg Phe Leu Arg Ala
            20                  25                  30

Trp His Pro Pro Val Ser Ala Arg Met Pro Thr Arg Arg Trp Ala
        35                  40                  45

Pro Gly Thr Gln Cys Ile Thr Lys Cys Glu His Thr Arg Pro Lys Pro
    50                  55                  60

Gly Glu Leu Ala Phe Arg Lys Gly Asp Val Val Thr Ile Leu Glu Ala
65                  70                  75                  80

Cys Glu Asn Lys Ser Trp Tyr Arg Val Lys His His Thr Ser Gly Gln
                85                  90                  95

Glu Gly Leu Leu Ala Ala Gly Ala Leu Arg Glu Arg Glu Ala Leu Ser
            100                 105                 110

Ala Asp Pro Lys Leu Ser Leu Met Pro Trp Phe His Gly Lys Ile Ser
            115                 120                 125

Gly Gln Glu Ala Val Gln Gln Leu Gln Pro Pro Glu Asp Gly Leu Phe
130                 135                 140

Leu Val Arg Glu Ser Ala Arg His Pro Gly Asp Tyr Val Leu Cys Val
145                 150                 155                 160

Ser Phe Gly Arg Asp Val Ile His Tyr Arg Val Leu His Arg Asp Gly
                165                 170                 175

His Leu Thr Ile Asp Glu Ala Val Phe Phe Cys Asn Leu Met Asp Met
            180                 185                 190

Val Glu His Tyr Ser Lys Asp Lys Gly Ala Ile Cys Thr Lys Leu Val
            195                 200                 205

Arg Pro Lys Arg Lys His Gly Thr Lys Ser Ala Glu Glu Leu Ala
        210                 215                 220

Arg Ala Gly Trp Leu Leu Asn Leu Gln His Leu Thr Leu Gly Ala Gln
225                 230                 235                 240

Ile Gly Glu Gly Glu Phe Gly Ala Val Leu Gln Gly Glu Tyr Leu Gly
                245                 250                 255

Gln Lys Val Ala Val Lys Asn Ile Lys Cys Asp Val Thr Ala Gln Ala
            260                 265                 270

Phe Leu Asp Glu Thr Ala Val Met Thr Lys Met Gln His Glu Asn Leu
        275                 280                 285

Val Arg Leu Leu Gly Val Ile Leu His Gln Gly Leu Tyr Ile Val Met
        290                 295                 300

Glu His Val Ser Lys Gly Asn Leu Val Asn Phe Leu Arg Thr Arg Gly
305                 310                 315                 320

Arg Ala Leu Val Asn Thr Ala Gln Leu Leu Gln Phe Ser Leu His Val
                325                 330                 335

Ala Glu Gly Met Glu Tyr Leu Glu Ser Lys Lys Leu Val His Arg Asp
            340                 345                 350

Leu Ala Ala Arg Asn Ile Leu Val Ser Glu Asp Leu Val Ala Lys Val
            355                 360                 365

Ser Asp Phe Gly Leu Ala Lys Ala Glu Arg Lys Gly Leu Asp Ser Ser
        370                 375                 380

Arg Leu Pro Val Lys Trp Thr Ala Pro Glu Ala Leu Lys His Gly Lys
385                 390                 395                 400
```

```
Phe Thr Ser Lys Ser Asp Val Trp Ser Phe Gly Val Leu Leu Trp Glu
                405                 410                 415
Val Phe Ser Tyr Gly Arg Ala Pro Tyr Pro Lys Met Ser Leu Lys Glu
            420                 425                 430
Val Ser Glu Ala Val Glu Lys Gly Tyr Arg Met Glu Pro Pro Glu Gly
        435                 440                 445
Cys Pro Gly Pro Val His Val Leu Met Ser Ser Cys Trp Glu Ala Glu
        450                 455                 460
Pro Ala Arg Arg Pro Pro Phe Arg Lys Leu Ala Glu Lys Leu Ala Arg
465                 470                 475                 480
Glu Leu Arg Ser Ala Gly Ala Pro Ala Ser Val Ser Gly Gln Asp Ala
                485                 490                 495
Asp Gly Ser Thr Ser Pro Arg Ser Gln Glu Pro
                500                 505
```

(2) INFORMATION FOR SEQ ID NO:3:

(i) SEQUENCE CHARACTERISTICS:
        (A) LENGTH: 2500 base pairs
        (B) TYPE: nucleic acid
        (C) STRANDEDNESS: unknown
        (D) TOPOLOGY: unknown (xi) SEQUENCE DESCRIPTION: SEQ ID NO:3:

```
CCGCTTTTTG CTTAGAGCTT GAGAGTCAAA GTTAAGGACC CACATGTATA CTTCGGCTCT      60
AGCGAGTCTA AGGATGATAA TATGGATACA AAATCTATTC TAGAAGAACT TCTTCTCAAA     120
AGATCACAGC AAAAGAAGAA AATGTCACCA AATAATTACA AGAACGGCT TTTTGTTTTG      180
ACCAAAACAA ACCTTTCCTA CTATGAATAT GACAAAATGA AAGGGGCAG CAGAAAAGGA      240
TCCATTGAAA TTAAGAAAAT CAGATGTGTG GAGAAAGTAA ATCTCGAGGA GCAGACGCCT     300
GTAGAGAGAC AGTACCCATT TCAGATTGTC TATAAAGATG GCTTCTCTA TGTCTATGCA      360
TCAAATGAAG AGAGCCGAAG TCAGTGGTTG AAAGCATTAC AAAAAGAGAT AAGGGGTAAC     420
CCCCACCTGC TGGTCAAGTA CCATAGTGGG TTCTTCGTGG ACGGGAAGTT CCTGTGTTGC     480
CAGCAGAGCT GTAAAGCAGC CCAGGATGT ACCCTCTGGG AAGCATATGC TAATCTGCAT      540
ACTGCAGTCA ATGAAGAGAA ACACAGAGTT CCCACCTTCC CAGACAGAGT GCTGAAGATA     600
CCTCGGGCAG TTCCTGTTCT CAAAATGGAT GCACCATCTT CAAGTACCAC TCTAGCCCAA     660
TATGACAACG AATCAAAGAA AAACTATGGC TCCCAGCCAC CATCTTCAAG TACCAGTCTA     720
GCGCAATATG ACAGCAACTC AAAGAAAATC TATGGCTCCC AGCCAAACTT CAACATGCAG     780
TATATTCCAA GGGAAGACTT CCCTGACTGG TGGCAAGTAA GAAAACTGAA AGTAGCAGC      840
AGCAGTGAAG ATGTTGCAAG CAGTAACCAA AAAGAAAGAA ATGTGAATCA CACCACCTCA     900
AAGATTTCAT GGGAATTCCC TGAGTCAAGT TCATCTGAAG AAGAGGAAAA CCTGGATGAT     960
TATGACTGGT TGCTGGTAA CATCTCCAGA TCACAATCTG AACAGTTACT CAGACAAAAG    1020
GGAAAAGAAG GAGCATTTAT GGTTAGAAAT TCGAGCCAAG TGGGAATGTA CACAGTGTCC    1080
TTATTTAGTA AGGCTGTGAA TGATAAAAAA GGAACTGTCA ACATTACCA CGTGCATACA     1140
AATGCTGAGA ACAAATTATA CCTGGCAGAA AACTACTGTT TTGATTCCAT TCCAAAGCTT    1200
ATTCATTATC ATCAACACAA TTCAGCAGGC ATGATCACAC GGCTCCGCCA CCCTGTGTCA    1260
ACAAAGGCCA CAAGGTCCC CGACTCTGTG TCCCTGGGAA ATGGAATCTG GAACTGAAA      1320
AGAGAAGAGA TTACCTTGTT GAAGGAGCTG GGAAGTGGCC AGTTTGGAGT GGTCCAGCTG    1380
```

```
GGCAAGTGGA AGGGGCAGTA TGATGTTGCT GTTAAGATGA TCAAGGAGGG CTCCATGTCA    1440

GAAGATGAAT TCTTTCAGGA GGCCCAGACT ATGATGAAAC TCAGCCATCC CAAGCTGGTT    1500

AAATTCTATG GAGTGTGTTC AAAGGAATAC CCCATATACA TAGTGACTGA ATATATAAGC    1560

AATGGCTGCT TGCTGAATTA CCTGAGGAGT CACGGAAAAG GACTTGAACC TTCCCAGCTC    1620

TTAGAAATGT GCTACGATGT CTGTGAAGGC ATGGCCTTCT TGGAGAGTCA CCAATTCATA    1680

CACCGGGACT TGGCTGCTCG TAACTGCTTG GTGGACAGAG ATCTCTGTGT GAAAGTATCT    1740

GACTTTGGAA TGACAAGGTA TGTTCTTGAT GACCAGTATG TCAGTTCAGT CGGAACAAAG    1800

TTTCCAGTCA AGTGGTCAGC TCCAGAGGTG TTTCATTACT TCAAATACAG CAGCAAGTCA    1860

GACGTATGGG CATTTGGGAT CCTGATGTGG GAGGTGTTCA GCCTGGGGAA GCAGCCCTAT    1920

GACTTGTATG ACAACTCCCA GGTGGTTCTG AAGGTCTCCC AGGGCCACAG GCTTTACCGG    1980

CCCCACCTGG CATCGGACAC CATCTACCAG ATCATGTACA GCTGCTGGCA CGAGCTTCCA    2040

GAAAAGCGTC CCACATTTCA GCAACTCCTG TCTTCCATTG AACCACTTCG GGAAAAAGAC    2100

AAGCATTGAA GAAGAAATTA GGAGTGCTGA TAAGAATGAA TATAGATGCT GGCCAGCATT    2160

TTCATTCATT TTAAGGAAAG TAGCAAGGCA TAATGTAATT TAGCTAGTTT TTAATAGTGT    2220

TCTCTGTATT GTCTATTATT TAGAAATGAA CAAGGCAGGA AACAAAAGAT TCCCTTGAAA    2280

TTTAGGTCAA ATTAGTAATT TTGTTTATGC TGCCCCTGAT ATAACACTTT CCAGCCTATA    2340

GCAGAAGCAC ATTTTCAGAC TGCAATATAG AGACTGTGTT CATGTGTAAA GACTGAGCAG    2400

AACTGAAAAA TTACTTATTG GATATTCATT CTTTTCTTTA TATTGTCATT GTCACAACAA    2460

TTAAATATAC TACCAAGTAC AAAAAAAAAA AAAAAAAAA                           2500
```

(2) INFORMATION FOR SEQ ID NO:4:

(i) SEQUENCE CHARACTERISTICS:
        (A) LENGTH: 675 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:4:

```
Met Asp Thr Lys Ser Ile Leu Glu Glu Leu Leu Lys Arg Ser Gln
 1               5                  10                  15

Gln Lys Lys Lys Met Ser Pro Asn Asn Tyr Lys Glu Arg Leu Phe Val
                20                  25                  30

Leu Thr Lys Thr Asn Leu Ser Tyr Tyr Glu Tyr Asp Lys Met Lys Arg
            35                  40                  45

Gly Ser Arg Lys Gly Ser Ile Glu Ile Lys Lys Ile Arg Cys Val Glu
        50                  55                  60

Lys Val Asn Leu Glu Glu Gln Thr Pro Val Glu Arg Gln Tyr Pro Phe
65                  70                  75                  80

Gln Ile Val Tyr Lys Asp Gly Leu Leu Tyr Val Tyr Ala Ser Asn Glu
                85                  90                  95

Glu Ser Arg Ser Gln Trp Leu Lys Ala Leu Gln Lys Glu Ile Arg Gly
            100                 105                 110

Asn Pro His Leu Leu Val Lys Tyr His Ser Gly Phe Phe Val Asp Gly
        115                 120                 125

Lys Phe Leu Cys Cys Gln Gln Ser Cys Lys Ala Ala Pro Gly Cys Thr
    130                 135                 140

Leu Trp Glu Ala Tyr Ala Asn Leu His Thr Ala Val Asn Glu Glu Lys
```

-continued

```
145                 150                 155                 160
His Arg Val Pro Thr Phe Pro Asp Arg Val Leu Lys Ile Pro Arg Ala
                165                 170                 175
Val Pro Val Leu Lys Met Asp Ala Pro Ser Ser Thr Thr Leu Ala
            180                 185                 190
Gln Tyr Asp Asn Glu Ser Lys Lys Asn Tyr Gly Ser Gln Pro Pro Ser
            195                 200                 205
Ser Ser Thr Ser Leu Ala Gln Tyr Asp Ser Asn Ser Lys Lys Ile Tyr
            210                 215                 220
Gly Ser Gln Pro Asn Phe Asn Met Gln Tyr Ile Pro Arg Glu Asp Phe
225                 230                 235                 240
Pro Asp Trp Trp Gln Val Arg Lys Leu Lys Ser Ser Ser Ser Ser Glu
                245                 250                 255
Asp Val Ala Ser Ser Asn Gln Lys Glu Arg Asn Val Asn His Thr Thr
                260                 265                 270
Ser Lys Ile Ser Trp Glu Phe Pro Glu Ser Ser Ser Ser Glu Glu Glu
            275                 280                 285
Glu Asn Leu Asp Asp Tyr Asp Trp Phe Ala Gly Asn Ile Ser Arg Ser
    290                 295                 300
Gln Ser Glu Gln Leu Leu Arg Gln Lys Gly Lys Glu Gly Ala Phe Met
305                 310                 315                 320
Val Arg Asn Ser Ser Gln Val Gly Met Tyr Thr Val Ser Leu Phe Ser
                325                 330                 335
Lys Ala Val Asn Asp Lys Lys Gly Thr Val Lys His Tyr His Val His
                340                 345                 350
Thr Asn Ala Glu Asn Lys Leu Tyr Leu Ala Glu Asn Tyr Cys Phe Asp
            355                 360                 365
Ser Ile Pro Lys Leu Ile His Tyr His Gln His Asn Ser Ala Gly Met
    370                 375                 380
Ile Thr Arg Leu Arg His Pro Val Ser Thr Lys Ala Asn Lys Val Pro
385                 390                 395                 400
Asp Ser Val Ser Leu Gly Asn Gly Ile Trp Glu Leu Lys Arg Glu Glu
                405                 410                 415
Ile Thr Leu Leu Lys Glu Leu Gly Ser Gly Gln Phe Gly Val Val Gln
            420                 425                 430
Leu Gly Lys Trp Lys Gly Gln Tyr Asp Val Ala Val Lys Met Ile Lys
            435                 440                 445
Glu Gly Ser Met Ser Glu Asp Glu Phe Phe Gln Glu Ala Gln Thr Met
    450                 455                 460
Met Lys Leu Ser His Pro Lys Leu Val Lys Phe Tyr Gly Val Cys Ser
465                 470                 475                 480
Lys Glu Tyr Pro Ile Tyr Ile Val Thr Glu Tyr Ile Ser Asn Gly Cys
                485                 490                 495
Leu Leu Asn Tyr Leu Arg Ser His Gly Lys Gly Leu Glu Pro Ser Gln
            500                 505                 510
Leu Leu Glu Met Cys Tyr Asp Val Cys Glu Gly Met Ala Phe Leu Glu
            515                 520                 525
Ser His Gln Phe Ile His Arg Asp Leu Ala Ala Arg Asn Cys Leu Val
    530                 535                 540
Asp Arg Asp Leu Cys Val Lys Val Ser Asp Phe Gly Met Thr Arg Tyr
545                 550                 555                 560
Val Leu Asp Asp Gln Tyr Val Ser Ser Val Gly Thr Lys Phe Pro Val
                565                 570                 575
```

```
Lys Trp Ser Ala Pro Glu Val Phe His Tyr Phe Lys Tyr Ser Ser Lys
            580                 585                 590

Ser Asp Val Trp Ala Phe Gly Ile Leu Met Trp Glu Val Phe Ser Leu
            595                 600                 605

Gly Lys Gln Pro Tyr Asp Leu Tyr Asp Asn Ser Gln Val Val Leu Lys
            610                 615                 620

Val Ser Gln Gly His Arg Leu Tyr Arg Pro His Leu Ala Ser Asp Thr
625                 630                 635                 640

Ile Tyr Gln Ile Met Tyr Ser Cys Trp His Glu Leu Pro Glu Lys Arg
                645                 650                 655

Pro Thr Phe Gln Gln Leu Leu Ser Ser Ile Glu Pro Leu Arg Glu Lys
            660                 665                 670

Asp Lys His
        675

(2) INFORMATION FOR SEQ ID NO:5:

(i) SEQUENCE CHARACTERISTICS:
        (A) LENGTH: 2770 base pairs
        (B) TYPE: nucleic acid
        (C) STRANDEDNESS: unknown
        (D) TOPOLOGY: unknown (xi) SEQUENCE DESCRIPTION: SEQ ID NO:5:

CCGGACTGGT CGAAAGACAG GAACAGACTT GAAACAGGGG GAGAGCTCCT GGCGAAACGA      60

AGACGTGGAG GTTTTACCAG GGATAAGAAG AAAAGACACC TTCCTAGTGA GCAGCTGCCC     120

AGCTCCTGCT CAGTTTTGCC TCGGGGTAGC ACCTCCAGCC ACAGAAAGCA AGCCGGTAAG     180

TCTCTCCAGG TAGGACTTGC TGCAACCCAG CTGCTGGACT GATCTGAAAC GGGACTTTGC     240

ATACTCTCCG AAGTATGGTG AGTTGGTGCT GACTTCAAAG TTGCCTGGTG AAGGAAGATA     300

AGGTGGATCG CAGAGACTAA GGGGAGAGGG AGAAGCCCTG CTCCTCTTCT CCCCACCAAG     360

GCACAATGAG CAACATCTGT CAGAGGCTCT GGGAGTACCT AGAACCCTAT CTCCCCTGTT     420

TGTCCACGGA GGCAGACAAG TCAACCGTGA TTGAAAATCC AGGGGCCCTT TGCTCTCCCC     480

AGTCACAGAG GCATGGCCAC TACTTTGTGG CTTTGTTTGA TTACCAGGCT CGGACTGCTG     540

AGGACTTGAG CTTCCGAGCA GGTGACAAAC TTCAAGTTCT GGACACTTTG CATGAGGGCT     600

GGTGGTTTGC CAGACACTTG GAGAAAAGAC GAGATGGCTC CAGTCAGCAA CTACAAGGCT     660

ATATTCCTTC TAACTACGTG GCTGAGGACA GAAGCCTACA GGCAGAGCCG TGGTTCTTTG     720

GAGCAATCGG AAGATCAGAT GCAGAGAAAC AACTATTATA TTCAGAAAAC AAGACCGGTT     780

CCTTTCTAAT CAGAGAAAGT GAAAGCCAAA AAGGAGAATT CTCTCTTTCA GTTTTAGATG     840

GAGCAGTTGT AAAACACTAC AGAATTAAAA GACTGGATGA AGGGGATTT TTTCTCACGC      900

GAAGAAGAAT CTTTTCAACA CTGAACGAAT TTGTGAGCCA CTACACCAAG ACAAGTGACG     960

GCCTGTGTGT CAAGCTGGGG AAACCATGCT TAAAGATCCA GGTCCCAGCT CCATTTGATT    1020

TGTCGTATAA AACCGTGGAC CAATGGGAGA TAGACCGCAA CTCCATACAG CTTCTGAAGC    1080

GATTGGGATC TGGTCAGTTT GGCGAAGTAT GGGAAGGTCT GTGGAACAAT ACCACTCCAG    1140

TAGCAGTGAA AACATTAAAA CCAGGTTCAA TGGATCAAAA TGACTTCCTG AGGGAGGCAC    1200

AGATAATGAA GAACCTAAGA CATCCAAAGC TTATCCAGCT TTATGCTGTT TGCACTTTAG    1260

AAGATCCAAT TTATATTATT ACAGAGTTGA TGAGACATGG AAGTCTGCAA GAATATCTCC    1320

AAAATGACAC TGGATCAAAA ATCCATCTGA CTCAACAGGT AGACATGGCG GCACAGGTTG    1380
```

-continued

```
CCTCTGGAAT GGCCTATCTG GAGTCTCGGA ACTACATTCA CAGAGATCTG GCTGCCAGAA       1440

ATGTCCTCGT TGGTGAACAT AATATCTACA AAGTAGCAGA TTTTGGACTT GCCAGAGTTT       1500

TTAAGGTAGA TAATGAAGAC ATCTATGAAT CTAGACACGA AATAAAGCTG CCGGTGAAGT       1560

GGACTGCGCC CGAAGCCATT CGTAGTAATA AATTCAGCAT TAAGTCCGAT GTATGGTCAT       1620

TTGGAATCCT TCTTTATGAA ATCATTACTT ATGGCAAAAT GCCTTACAGT GGTATGACAG       1680

GTGCCCAGGT AATCCAGATG TTGGCTCAAA ACTATAGACT TCCGCAACCA TCCAACTGTC       1740

CACAGCAATT TTACAACATC ATGTTGGAGT GCTGGAATGC AGAGCCTAAG GAACGACCTA       1800

CATTTGAGAC ACTGCGTTGG AAACTTGAAG ACTATTTTGA AACAGACTCT TCATATTCAG       1860

ATGCAAATAA CTTCATAAGA TGAACACTGG AGAAGAATAA CAAATAATAA AGTAGCAAAA       1920

CAAATTCAAA TAATCCATTC CAAAATACAA TGTTATCAAC CAACTGCACA ATCAGTTTAT       1980

CCTGACATAT TCAAGTGATA GGATAAAGTT GGCCATGTAT TATGAAAAAG ATTATTTGTG       2040

CATTTTATTG ACTGGGCAAC ACTGCAGGAC AGTCAAGGTC ATATATAATT GCTCACTGCC       2100

TGGAAAATTA AGCACACTAA ACCAAGTTAT TTTTCTTTTT AAGAGATACT TACATTTCCA       2160

TTTATTGTTT GAAATGTCGC GATCAAGAGA ATCAACAGAT GATAGTCCAA TTTTTACTCA       2220

GTGATGACTG TGTAGCATTT TCCTGTTTAC TGATTAGAGT GGTTATTCAT TATTCCTCAG       2280

ATTGCTGAAT CCCATCAGGC TGTTATTATG AAGGAATTTG ATTGCTTTGC TGCACAGCAG       2340

GACCTGTGCT TTGAGATTTT TTTTTCTCTT TTAAAATATC CTGTAACTAC AATGATGGTA       2400

AAGCCATGTT AAATGACTTG ATTGTACTTG GAGTAATTGC ACATTTTTTT CTATGCATAA       2460

AAAAATGATG CAGCTGTTGA GAAAACGAAG TCTTTTTCAT TTTGCAGAAG GAAATGATGG       2520

AATTTTTCTG TACTTCAGTA TGTGTCAACT GAGAGTCATA TACATTAGTT TTAATCTCTT       2580

AATATTGAGA ATCAGGTTGC AAAACGGATG AGTTATTATC TATGGAAATG TGAGAAATGT       2640

CTAATAGCCC ATAAGTCTG AGAAATAGGT ATCAAAATAG TTTAGGAAAA TGAGAGGAGA       2700

ACAGTAGGAT TGCTGTGGCC TAGACTTCTG AGTAATTAAT AAAGAAAAAG AAGTACCAAA       2760

AAAAAAAAAA                                                              2770
```

(2) INFORMATION FOR SEQ ID NO:6:

(i) SEQUENCE CHARACTERISTICS:
        (A) LENGTH: 506 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:6:

```
Met Ser Asn Ile Cys Gln Arg Leu Trp Glu Tyr Leu Glu Pro Tyr Leu
 1               5                  10                  15

Pro Cys Leu Ser Thr Glu Ala Asp Lys Ser Thr Val Ile Glu Asn Pro
                20                  25                  30

Gly Ala Leu Cys Ser Pro Gln Ser Gln Arg His Gly His Tyr Phe Val
            35                  40                  45

Ala Leu Phe Asp Tyr Gln Ala Arg Thr Ala Glu Asp Leu Ser Phe Arg
        50                  55                  60

Ala Gly Asp Lys Lys Leu Gln Val Leu Asp Thr Leu His Glu Gly Trp
65                  70                  75                  80

Trp Phe Ala Arg His Leu Glu Lys Arg Asp Gly Ser Ser Gln Gln
                85                  90                  95
```

-continued

```
Leu Gln Gly Tyr Ile Pro Ser Asn Tyr Val Ala Glu Asp Arg Ser Leu
            100                 105                 110

Gln Ala Glu Pro Trp Phe Phe Gly Ala Ile Gly Arg Ser Asp Ala Glu
            115                 120                 125

Lys Gln Leu Leu Tyr Ser Glu Asn Lys Thr Gly Ser Phe Leu Ile Arg
            130                 135                 140

Glu Ser Glu Ser Gln Lys Gly Glu Phe Ser Leu Ser Val Leu Asp Gly
145                 150                 155                 160

Ala Val Val Lys His Tyr Arg Ile Lys Arg Leu Asp Glu Gly Gly Phe
                165                 170                 175

Phe Leu Thr Arg Arg Arg Ile Phe Ser Thr Leu Asn Glu Phe Val Ser
            180                 185                 190

His Tyr Thr Lys Thr Ser Asp Gly Leu Cys Val Lys Leu Gly Lys Pro
            195                 200                 205

Cys Leu Lys Ile Gln Val Pro Ala Pro Phe Asp Leu Ser Tyr Lys Thr
            210                 215                 220

Val Asp Gln Trp Glu Ile Asp Arg Asn Ser Ile Gln Leu Leu Lys Arg
225                 230                 235                 240

Leu Gly Ser Gly Gln Phe Gly Glu Val Trp Glu Gly Leu Trp Asn Asn
                245                 250                 255

Thr Thr Pro Val Ala Val Lys Thr Leu Lys Pro Gly Ser Met Asp Pro
            260                 265                 270

Asn Asp Phe Leu Arg Glu Ala Gln Ile Met Lys Asn Leu Arg His Pro
            275                 280                 285

Lys Leu Ile Gln Leu Tyr Ala Val Cys Thr Leu Glu Asp Pro Ile Tyr
            290                 295                 300

Ile Ile Thr Glu Leu Met Arg His Gly Ser Leu Gln Glu Tyr Leu Gln
305                 310                 315                 320

Asn Asp Thr Gly Ser Lys Ile His Leu Thr Gln Gln Tyr Asp Met Ala
                325                 330                 335

Ala Gln Val Ala Ser Gly Met Ala Tyr Leu Glu Ser Arg Asn Tyr Ile
            340                 345                 350

His Arg Asp Leu Ala Ala Arg Asn Val Leu Val Gly Glu His Asn Ile
            355                 360                 365

Tyr Lys Val Ala Asp Phe Gly Leu Ala Arg Val Phe Lys Val Asp Asn
            370                 375                 380

Glu Asp Ile Tyr Glu Ser Arg His Glu Ile Lys Leu Pro Val Lys Trp
385                 390                 395                 400

Thr Ala Pro Glu Ala Ile Arg Ser Asn Lys Phe Ser Ile Lys Ser Asp
                405                 410                 415

Val Trp Ser Phe Gly Ile Leu Leu Tyr Glu Ile Ile Thr Tyr Gly Lys
            420                 425                 430

Met Pro Tyr Ser Gly Met Thr Gly Ala Gln Val Ile Gln Met Leu Ala
            435                 440                 445

Gln Asn Tyr Arg Leu Pro Gln Pro Ser Asn Cys Pro Gln Gln Phe Tyr
            450                 455                 460

Asn Ile Met Leu Glu Cys Trp Asn Ala Glu Pro Lys Glu Arg Pro Thr
465                 470                 475                 480

Phe Glu Thr Leu Arg Trp Lys Leu Glu Asp Tyr Phe Glu Thr Asp Ser
                485                 490                 495

Ser Tyr Ser Asp Ala Asn Asn Phe Ile Arg
            500                 505
```

-continued (2) INFORMATION FOR SEQ ID NO:7:

(i) SEQUENCE CHARACTERISTICS:
        (A) LENGTH: 450 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:7:

```
Met Ser Ala Ile Gln Ala Ala Trp Pro Ser Gly Thr Glu Cys Ile Ala
  1               5                  10                  15

Lys Tyr Asn Phe His Gly Thr Ala Glu Gln Asp Leu Pro Phe Cys Lys
             20                  25                  30

Gly Asp Val Leu Thr Ile Val Ala Val Thr Lys Asp Pro Asn Trp Tyr
         35                  40                  45

Lys Ala Lys Asn Lys Val Gly Arg Glu Gly Ile Ile Pro Ala Asn Tyr
 50                  55                  60

Val Gln Lys Arg Glu Gly Val Lys Ala Gly Thr Lys Leu Ser Leu Met
 65                  70                  75                  80

Pro Trp Phe His Gly Lys Ile Thr Arg Glu Gln Ala Glu Arg Leu Leu
                 85                  90                  95

Tyr Pro Pro Glu Thr Gly Leu Phe Leu Val Arg Glu Ser Thr Asn Tyr
            100                 105                 110

Pro Gly Asp Tyr Thr Leu Cys Val Ser Cys Asp Gly Lys Val Glu His
        115                 120                 125

Tyr Arg Ile Met Tyr His Ala Ser Lys Leu Ser Ile Asp Glu Glu Val
130                 135                 140

Tyr Phe Glu Asn Leu Met Gln Leu Val Glu His Tyr Thr Ser Asp Ala
145                 150                 155                 160

Asp Gly Leu Cys Thr Arg Leu Ile Lys Pro Lys Val Met Glu Gly Thr
                165                 170                 175

Val Ala Ala Gln Asp Glu Phe Tyr Arg Ser Gly Trp Ala Leu Asn Met
            180                 185                 190

Lys Glu Leu Lys Leu Leu Gln Thr Ile Gly Lys Gly Glu Phe Gly Asp
        195                 200                 205

Val Met Leu Gly Asp Tyr Arg Gly Asn Lys Val Ala Val Lys Cys Ile
210                 215                 220

Lys Asn Asp Ala Thr Ala Gln Ala Phe Leu Ala Glu Ala Ser Val Met
225                 230                 235                 240

Thr Gln Leu Arg His Ser Asn Leu Val Gln Leu Leu Gly Val Ile Val
                245                 250                 255

Glu Glu Lys Gly Gly Leu Tyr Ile Val Thr Glu Tyr Met Ala Lys Gly
            260                 265                 270

Ser Leu Val Asp Tyr Leu Arg Ser Arg Gly Arg Ser Val Leu Gly Gly
        275                 280                 285

Asp Cys Leu Leu Lys Phe Ser Leu Asp Val Cys Glu Ala Met Glu Tyr
    290                 295                 300

Leu Glu Gly Asn Asn Phe Val His Arg Asp Leu Ala Ala Arg Asn Val
305                 310                 315                 320

Leu Val Ser Glu Asp Asn Val Ala Lys Val Ser Asp Phe Gly Leu Thr
                325                 330                 335

Lys Glu Ala Ser Ser Thr Gln Asp Thr Gly Lys Leu Pro Val Lys Trp
            340                 345                 350

Thr Ala Pro Glu Ala Leu Arg Glu Lys Lys Phe Ser Thr Lys Ser Asp
```

```
                355                 360                 365
Val Trp Ser Phe Gly Ile Leu Leu Trp Glu Ile Tyr Ser Phe Gly Arg
    370                 375                 380

Val Pro Tyr Pro Arg Ile Pro Leu Lys Asp Val Val Pro Arg Val Glu
385                 390                 395                 400

Lys Gly Tyr Lys Met Asp Ala Pro Asp Gly Cys Pro Pro Ala Val Tyr
                405                 410                 415

Glu Val Met Lys Asn Cys Trp His Leu Asp Ala Ala Met Arg Pro Ser
                420                 425                 430

Phe Leu Gln Leu Arg Glu Gln Leu Glu His Ile Lys Thr His Glu Leu
                435                 440                 445

His Leu
    450

(2) INFORMATION FOR SEQ ID NO:8:

(i) SEQUENCE CHARACTERISTICS:
        (A) LENGTH: 659 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:8:

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
                20                  25                  30

Thr Val His Lys Leu Ser Tyr Tyr Glu Tyr Asp Phe Glu Arg Gly Arg
            35                  40                  45

Arg Gly Ser Lys Lys Gly Ser Ile Asp Val Glu Lys Ile Thr Cys Val
        50                  55                  60

Glu Thr Val Val Pro Glu Lys Asn Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
                100                 105                 110

Val Phe Ser Pro Thr Glu Glu Leu Arg Lys Arg Trp Ile His Gln Leu
                115                 120                 125

Lys Asn Val Ile Arg Tyr Asn Ser Asp Leu Val Gln Lys Tyr His Pro
            130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
                180                 185                 190

Glu Glu Asp Gln Ile Leu Lys Lys Pro Leu Pro Pro Glu Pro Ala Ala
                195                 200                 205

Ala Pro Val Ser Thr Ser Glu Leu Lys Lys Val Val Ala Leu Tyr Asp
                210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
```

-continued

```
                245                 250                 255
Lys Asn Gly Gln Glu Gly Tyr Ile Pro Ser Asn Tyr Val Thr Glu Ala
            260                 265                 270
Glu Asp Ser Ile Glu Met Tyr Glu Trp Tyr Ser Lys His Met Thr Arg
        275                 280                 285
Ser Gln Ala Glu Gln Leu Leu Lys Gln Glu Gly Lys Glu Gly Gly Phe
    290                 295                 300
Ile Val Arg Asp Ser Ser Lys Ala Gly Lys Tyr Thr Val Ser Val Phe
305                 310                 315                 320
Ala Lys Ser Thr Gly Asp Pro Gln Gly Val Ile Arg His Tyr Val Val
                325                 330                 335
Cys Ser Thr Pro Gln Ser Gln Tyr Tyr Leu Ala Glu Lys His Leu Phe
            340                 345                 350
Ser Thr Ile Pro Glu Leu Ile Asn Tyr His Gln His Asn Ser Ala Gly
        355                 360                 365
Leu Ile Ser Arg Leu Lys Tyr Pro Val Ser Gln Gln Asn Lys Asn Ala
    370                 375                 380
Pro Ser Thr Ala Gly Leu Gly Tyr Gly Ser Trp Glu Ile Asp Pro Lys
385                 390                 395                 400
Asp Leu Thr Phe Leu Lys Glu Leu Gly Thr Gly Gln Phe Gly Val Val
                405                 410                 415
Lys Tyr Gly Lys Trp Arg Gly Gln Tyr Asp Val Ala Ile Lys Met Ile
            420                 425                 430
Lys Glu Gly Ser Met Ser Glu Asp Glu Phe Ile Glu Ala Lys Val
        435                 440                 445
Met Met Asn Leu Ser His Glu Lys Leu Val Gln Leu Tyr Gly Val Cys
    450                 455                 460
Thr Lys Gln Arg Pro Ile Phe Ile Ile Thr Glu Tyr Met Ala Asn Gly
465                 470                 475                 480
Cys Leu Leu Asn Tyr Leu Arg Glu Met Arg His Arg Phe Gln Thr Gln
                485                 490                 495
Gln Leu Leu Glu Met Cys Lys Asp Val Cys Glu Ala Met Glu Tyr Leu
            500                 505                 510
Glu Ser Lys Gln Phe Leu His Arg Asp Leu Ala Ala Arg Asn Cys Leu
        515                 520                 525
Val Asn Asp Gln Gly Val Val Lys Val Ser Asp Phe Gly Leu Ser Arg
    530                 535                 540
Tyr Val Leu Asp Asp Glu Tyr Thr Ser Ser Val Gly Ser Lys Phe Pro
545                 550                 555                 560
Val Arg Trp Ser Pro Pro Glu Val Leu Met Tyr Ser Lys Phe Ser Ser
                565                 570                 575
Lys Ser Asp Ile Trp Ala Phe Gly Val Leu Met Trp Glu Ile Tyr Ser
            580                 585                 590
Leu Gly Lys Met Pro Tyr Glu Arg Phe Thr Asn Ser Glu Thr Ala Glu
        595                 600                 605
His Ile Ala Gln Gly Leu Arg Leu Tyr Arg Pro His Leu Ala Ser Glu
    610                 615                 620
Lys Val Tyr Thr Ile Met Tyr Ser Cys Trp His Glu Lys Ala Asp Glu
625                 630                 635                 640
Arg Pro Thr Phe Lys Ile Leu Leu Ser Asn Ile Leu Asp Val Met Asp
                645                 650                 655
Glu Glu Ser
```

(2) INFORMATION FOR SEQ ID NO:9:

(i) SEQUENCE CHARACTERISTICS:
        (A) LENGTH: 620 amino acids
        (B) TYPE: amino acid
        (C) STRANDEDNESS: unknown
        (D) TOPOLOGY: unknown (xi) SEQUENCE DESCRIPTION: SEQ ID NO:9:

```
Met Asn Asn Phe Ile Leu Leu Glu Glu Gln Leu Ile Lys Lys Ser Gln
 1               5                  10                  15

Gln Lys Arg Arg Thr Ser Pro Ser Asn Phe Lys Val Arg Phe Phe Val
             20                  25                  30

Leu Thr Lys Ala Ser Leu Ala Tyr Phe Glu Asp Arg His Gly Lys Lys
         35                  40                  45

Arg Thr Leu Lys Gly Ser Ile Glu Leu Ser Arg Ile Lys Cys Val Glu
     50                  55                  60

Ile Val Lys Ser Asp Ile Ser Ile Pro Cys His Tyr Lys Tyr Pro Phe
65                  70                  75                  80

Gln Val Val His Asp Asn Tyr Leu Leu Tyr Val Phe Ala Pro Asp Arg
                 85                  90                  95

Glu Ser Arg Gln Arg Trp Val Leu Ala Leu Lys Glu Glu Thr Arg Asn
            100                 105                 110

Asn Asn Ser Leu Val Pro Lys Tyr His Pro Asn Phe Trp Met Asp Gly
        115                 120                 125

Lys Trp Arg Cys Cys Ser Gln Leu Glu Lys Leu Ala Thr Gly Cys Ala
130                 135                 140

Gln Tyr Asp Pro Thr Lys Asn Ala Ser Lys Lys Pro Leu Pro Pro Thr
145                 150                 155                 160

Pro Glu Asp Asn Arg Arg Pro Leu Trp Glu Pro Glu Thr Val Val
                165                 170                 175

Ile Ala Leu Tyr Asp Tyr Gln Thr Asn Asp Pro Gln Glu Leu Ala Leu
            180                 185                 190

Arg Arg Asn Glu Glu Tyr Cys Leu Leu Asp Ser Ser Glu Ile His Trp
        195                 200                 205

Trp Arg Val Gln Asp Arg Asn Gly His Glu Gly Tyr Val Pro Ser Ser
210                 215                 220

Tyr Leu Val Glu Lys Ser Pro Asn Asn Leu Glu Thr Tyr Glu Trp Tyr
225                 230                 235                 240

Asn Lys Ser Ile Ser Arg Asp Lys Ala Glu Lys Leu Leu Leu Asp Thr
                245                 250                 255

Gly Lys Glu Gly Ala Phe Met Val Arg Asp Ser Arg Thr Ala Gly Thr
            260                 265                 270

Tyr Thr Val Ser Val Phe Thr Lys Ala Val Ser Glu Asn Asn Pro
        275                 280                 285

Cys Ile Lys His Tyr His Ile Lys Glu Thr Asn Asp Asn Pro Lys Arg
290                 295                 300

Tyr Tyr Val Ala Glu Lys Tyr Val Phe Asp Ser Ile Pro Leu Leu Ile
305                 310                 315                 320

Asn Tyr His Gln His Asn Gly Gly Leu Val Thr Arg Leu Arg Tyr
                325                 330                 335

Pro Val Cys Phe Gly Arg Gln Lys Ala Pro Val Thr Ala Gly Leu Arg
            340                 345                 350

Tyr Gly Lys Trp Val Ile Asp Pro Ser Glu Leu Thr Phe Val Gln Glu
        355                 360                 365
```

-continued

```
Ile Gly Ser Gly Gln Phe Gly Leu Val His Leu Gly Tyr Trp Leu Asn
        370                 375                 380
Lys Asp Lys Val Ala Ile Lys Thr Ile Arg Glu Gly Ala Met Ser Glu
385                 390                 395                 400
Glu Asp Phe Ile Glu Glu Ala Glu Val Met Met Lys Leu Ser His Pro
                405                 410                 415
Lys Leu Val Gln Leu Tyr Gly Val Cys Leu Glu Gln Ala Pro Ile Cys
                420                 425                 430
Leu Val Phe Glu Phe Met Glu His Gly Cys Leu Ser Asp Tyr Leu Arg
                435                 440                 445
Thr Gln Arg Gly Leu Phe Ala Ala Glu Thr Leu Leu Gly Met Cys Leu
        450                 455                 460
Asp Val Cys Glu Gly Met Ala Tyr Leu Glu Glu Ala Cys Val Ile His
465                 470                 475                 480
Arg Asp Leu Ala Ala Arg Asn Cys Leu Val Gly Glu Asn Gln Val Ile
                485                 490                 495
Lys Val Ser Asp Phe Gly Met Thr Arg Phe Val Leu Asp Asp Gln Tyr
                500                 505                 510
Thr Ser Ser Thr Gly Thr Lys Phe Pro Val Lys Trp Ala Ser Pro Glu
        515                 520                 525
Val Phe Ser Phe Ser Arg Tyr Ser Ser Lys Ser Asp Val Trp Ser Phe
530                 535                 540
Gly Val Leu Met Trp Glu Val Phe Ser Glu Gly Lys Ile Pro Tyr Glu
545                 550                 555                 560
Asn Arg Ser Asn Ser Glu Val Val Glu Asp Ile Ser Thr Gly Phe Arg
                565                 570                 575
Leu Tyr Lys Pro Arg Leu Ala Ser Thr His Val Tyr Gln Ile Met Asn
                580                 585                 590
His Cys Trp Lys Glu Arg Pro Glu Asp Arg Pro Ala Phe Ser Arg Leu
        595                 600                 605
Leu Arg Gln Leu Ala Glu Ile Ala Glu Ser Gly Leu
        610                 615                 620

(2) INFORMATION FOR SEQ ID NO:10:

(i) SEQUENCE CHARACTERISTICS:
        (A) LENGTH: 527 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:10:

Met Met Val Ser Phe Pro Val Lys Ile Asn Phe His Ser Ser Pro Gln
1               5                   10                  15
Ser Arg Asp Arg Trp Val Lys Lys Leu Lys Glu Glu Ile Lys Asn Asn
                20                  25                  30
Asn Asn Ile Met Ile Lys Tyr His Pro Lys Phe Trp Ala Asp Gly Ser
        35                  40                  45
Tyr Gln Cys Cys Arg Gln Thr Glu Lys Leu Ala Pro Gly Cys Glu Lys
50                  55                  60
Tyr Asn Leu Phe Glu Ser Ser Ile Arg Lys Thr Leu Pro Pro Ala Pro
65                  70                  75                  80
Glu Ile Lys Lys Arg Arg Pro Pro Pro Ile Pro Pro Glu Glu Glu
                85                  90                  95
```

```
Asn Thr Glu Glu Ile Val Val Ala Met Tyr Asp Phe Gln Ala Thr Glu
                100                 105                 110
Ala His Asp Leu Arg Leu Glu Arg Gly Gln Glu Tyr Ile Ile Leu Glu
            115                 120                 125
Lys Asn Asp Leu His Trp Trp Arg Ala Arg Asp Lys Tyr Gly Trp Tyr
        130                 135                 140
Cys Arg Asn Thr Asn Arg Ser Lys Ala Glu Gln Leu Leu Arg Thr Glu
145                 150                 155                 160
Asp Lys Glu Gly Gly Phe Met Val Arg Asp Ser Ser Gln Pro Gly Leu
                165                 170                 175
Tyr Thr Val Ser Leu Tyr Thr Lys Phe Gly Glu Gly Ser Ser Gly
            180                 185                 190
Phe Arg His Tyr His Ile Lys Glu Thr Ala Thr Ser Pro Lys Lys Tyr
        195                 200                 205
Tyr Leu Ala Glu Lys His Ala Phe Gly Ser Ile Pro Glu Ile Ile Glu
        210                 215                 220
Tyr His Lys His Asn Ala Ala Gly Leu Val Thr Arg Leu Arg Tyr Pro
225                 230                 235                 240
Val Ser Thr Lys Gly Lys Asn Ala Pro Thr Thr Ala Gly Phe Ser Tyr
                245                 250                 255
Asp Lys Trp Glu Ile Asn Pro Ser Glu Leu Thr Phe Met Arg Glu Leu
                260                 265                 270
Gly Ser Gly Leu Phe Gly Val Val Arg Leu Gly Lys Trp Arg Ala Gln
            275                 280                 285
Tyr Lys Val Ala Ile Lys Ala Ile Arg Glu Gly Ala Met Cys Glu Glu
        290                 295                 300
Asp Phe Ile Glu Glu Ala Lys Val Met Met Lys Leu Thr His Pro Lys
305                 310                 315                 320
Leu Val Gln Leu Tyr Gly Val Cys Thr Gln Gln Lys Pro Ile Tyr Ile
                325                 330                 335
Val Thr Glu Phe Met Glu Arg Gly Cys Leu Leu Asn Phe Leu Arg Gln
                340                 345                 350
Arg Gln Gly His Phe Ser Arg Asp Met Leu Leu Ser Met Cys Gln Asp
            355                 360                 365
Val Cys Glu Gly Met Glu Tyr Leu Glu Arg Asn Ser Phe Ile His Arg
        370                 375                 380
Asp Leu Ala Ala Arg Asn Cys Leu Val Asn Glu Ala Gly Val Val Lys
385                 390                 395                 400
Val Ser Asp Phe Gly Met Ala Arg Tyr Val Leu Asp Asp Gln Tyr Thr
                405                 410                 415
Ser Ser Ser Gly Ala Lys Phe Pro Val Lys Trp Cys Pro Pro Glu Val
                420                 425                 430
Phe Asn Tyr Ser Arg Phe Ser Ser Lys Ser Asp Val Trp Ser Phe Gly
            435                 440                 445
Val Leu Met Trp Glu Ile Phe Thr Glu Gly Arg Met Pro Phe Glu Lys
        450                 455                 460
Asn Thr Asn Tyr Glu Val Val Thr Met Val Thr Arg Gly His Arg Leu
465                 470                 475                 480
His Arg Pro Lys Leu Ala Thr Lys Tyr Leu Tyr Glu Val Met Leu Arg
                485                 490                 495
Cys Trp Gln Glu Arg Pro Glu Gly Arg Pro Ser Phe Glu Asp Leu Leu
                500                 505                 510
```

-continued

```
Arg Thr Ile Asp Glu Leu Val Glu Cys Glu Glu Thr Phe Gly Arg
        515                 520                 525
```

(2) INFORMATION FOR SEQ ID NO:11:

(i) SEQUENCE CHARACTERISTICS:
       (A) LENGTH: 537 amino acids
       (B) TYPE: amino acid
       (C) STRANDEDNESS: unknown
       (D) TOPOLOGY: unknown (ii) MOLECULE TYPE: None (xi) SEQUENCE DESCRIPTION: SEQ ID NO:11:

```
Met Gly Cys Val Gln Cys Lys Asp Lys Glu Ala Thr Lys Leu Thr Glu
1               5                   10                  15

Glu Arg Asp Gly Ser Leu Asn Gln Ser Ser Gly Tyr Arg Tyr Gly Thr
                20                  25                  30

Asp Pro Thr Pro Gln His Tyr Pro Ser Phe Gly Val Thr Ser Ile Pro
            35                  40                  45

Asn Tyr Asn Asn Phe His Ala Ala Gly Gly Gln Gly Leu Thr Val Phe
        50                  55                  60

Gly Gly Val Asn Ser Ser Ser His Thr Gly Thr Leu Arg Thr Arg Gly
65                  70                  75                  80

Gly Thr Gly Val Thr Leu Phe Val Ala Leu Tyr Asp Tyr Glu Ala Arg
                85                  90                  95

Thr Glu Asp Asp Leu Ser Phe His Lys Gly Glu Lys Phe Gln Ile Leu
            100                 105                 110

Asn Ser Ser Glu Gly Asp Trp Trp Glu Ala Arg Ser Leu Thr Thr Gly
        115                 120                 125

Glu Thr Gly Tyr Ile Pro Ser Asn Tyr Val Ala Pro Val Asp Ser Ile
130                 135                 140

Gln Ala Glu Glu Trp Tyr Phe Gly Lys Leu Gly Arg Lys Asp Ala Glu
145                 150                 155                 160

Arg Gln Leu Leu Ser Phe Gly Asn Pro Arg Gly Thr Phe Leu Ile Arg
                165                 170                 175

Glu Ser Glu Thr Thr Lys Gly Ala Tyr Ser Leu Ser Ile Arg Asp Trp
            180                 185                 190

Asp Asp Met Lys Gly Asp His Val Lys His Tyr Lys Ile Arg Lys Leu
        195                 200                 205

Asp Asn Gly Gly Tyr Tyr Ile Thr Thr Arg Ala Gln Phe Glu Thr Leu
    210                 215                 220

Gln Gln Leu Val Gln His Tyr Ser Glu Arg Ala Ala Gly Leu Cys Cys
225                 230                 235                 240

Arg Leu Val Val Pro Cys His Lys Gly Met Pro Arg Leu Thr Asp Leu
                245                 250                 255

Ser Val Lys Thr Lys Asp Val Trp Glu Ile Pro Arg Glu Ser Leu Gln
            260                 265                 270

Leu Ile Lys Arg Leu Gly Asn Gly Gln Phe Gly Glu Val Trp Met Gly
        275                 280                 285

Thr Trp Asn Gly Asn Thr Lys Val Ala Ile Lys Thr Leu Lys Pro Gly
    290                 295                 300

Thr Met Ser Pro Glu Ser Phe Leu Glu Glu Ala Gln Ile Met Lys Lys
305                 310                 315                 320

Leu Lys His Asp Lys Leu Val Gln Leu Tyr Ala Val Val Ser Glu Glu
                325                 330                 335
```

```
Pro Ile Tyr Ile Val Thr Glu Tyr Met Asn Lys Gly Ser Leu Leu Asp
            340                 345                 350

Phe Leu Lys Asp Gly Glu Gly Arg Ala Leu Lys Leu Pro Asn Leu Val
            355                 360                 365

Asp Met Ala Ala Gln Val Ala Ala Gly Met Ala Tyr Ile Glu Arg Met
            370                 375                 380

Asn Tyr Ile His Arg Asp Leu Arg Ser Ala Asn Ile Leu Val Gly Asn
385                 390                 395                 400

Gly Leu Ile Cys Lys Ile Ala Asp Phe Gly Leu Ala Arg Leu Ile Glu
                405                 410                 415

Asp Asn Glu Tyr Thr Ala Arg Gln Gly Ala Lys Phe Pro Ile Lys Trp
            420                 425                 430

Thr Ala Pro Glu Ala Ala Leu Tyr Gly Arg Phe Thr Ile Lys Ser Asp
            435                 440                 445

Val Trp Ser Phe Gly Ile Leu Leu Thr Glu Leu Val Thr Lys Gly Arg
            450                 455                 460

Val Pro Tyr Pro Gly Met Asn Asn Arg Glu Val Leu Glu Gln Val Glu
465                 470                 475                 480

Arg Gly Tyr Arg Met Pro Cys Pro Gln Asp Cys Pro Ile Ser Leu His
                485                 490                 495

Glu Leu Met Ile His Cys Trp Lys Lys Asp Pro Glu Glu Arg Pro Thr
            500                 505                 510

Phe Glu Tyr Leu Gln Ser Phe Leu Glu Asp Tyr Phe Thr Ala Thr Glu
            515                 520                 525

Pro Gln Tyr Gln Pro Gly Glu Asn Leu
            530                 535

(2) INFORMATION FOR SEQ ID NO:12:

(i) SEQUENCE CHARACTERISTICS:
        (A) LENGTH: 536 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:12:

Met Gly Cys Val His Cys Lys Glu Lys Ile Ser Gly Lys Gly Gln Gly
1               5                   10                  15

Gly Ser Gly Thr Gly Thr Pro Ala His Pro Ser Gln Tyr Asp Pro
            20                  25                  30

Asp Pro Thr Gln Leu Ser Gly Ala Phe Thr His Ile Pro Asp Phe Asn
            35                  40                  45

Asn Phe His Ala Ala Ala Val Ser Pro Pro Val Pro Phe Ser Gly Pro
50                  55                  60

Gly Phe Tyr Pro Cys Asn Thr Leu Gln Ala His Ser Ser Ile Thr Gly
65                  70                  75                  80

Gly Gly Val Thr Leu Phe Ile Ala Leu Tyr Asp Tyr Glu Ala Arg Thr
                85                  90                  95

Glu Asp Asp Leu Ser Phe Gln Lys Gly Glu Lys Phe His Ile Ile Asn
            100                 105                 110

Asn Thr Glu Gly Asp Trp Trp Glu Ala Arg Ser Leu Ser Ser Gly Ala
            115                 120                 125

Thr Gly Tyr Ile Pro Ser Asn Tyr Val Ala Pro Val Asp Ser Ile Gln
            130                 135                 140
```

```
Ala Glu Glu Trp Tyr Phe Gly Lys Ile Gly Arg Lys Asp Ala Glu Arg
145                 150                 155                 160

Gln Leu Leu Cys His Gly Asn Cys Arg Gly Thr Phe Leu Ile Arg Glu
                165                 170                 175

Ser Glu Thr Thr Lys Gly Ala Tyr Ser Leu Ser Ile Arg Asp Trp Asp
            180                 185                 190

Glu Ala Lys Gly Asp His Val Lys His Tyr Lys Ile Arg Lys Leu Asp
        195                 200                 205

Ser Gly Gly Tyr Tyr Ile Thr Thr Arg Ala Gln Phe Asp Thr Ile Gln
    210                 215                 220

Gln Leu Val Gln His Tyr Ile Glu Arg Ala Ala Gly Leu Cys Cys Arg
225                 230                 235                 240

Leu Ala Val Pro Cys Pro Lys Gly Thr Pro Lys Leu Ala Asp Leu Ser
                245                 250                 255

Val Lys Thr Lys Asp Val Trp Glu Ile Pro Arg Glu Ser Leu Gln Leu
                260                 265                 270

Leu Gln Lys Leu Gly Asn Gly Gln Phe Gly Glu Val Trp Met Gly Thr
                275                 280                 285

Trp Asn Gly Thr Thr Lys Val Ala Val Lys Thr Leu Lys Pro Gly Thr
                290                 295                 300

Met Ser Pro Glu Ala Phe Leu Glu Glu Ala Gln Ile Met Lys Arg Leu
305                 310                 315                 320

Arg His Asp Lys Leu Val Gln Leu Tyr Ala Val Val Ser Glu Glu Pro
                325                 330                 335

Ile Tyr Ile Val Thr Glu Phe Met Ser Gln Gly Ser Leu Leu Asp Phe
                340                 345                 350

Leu Lys Asp Gly Asp Gly Arg Tyr Leu Lys Leu Pro Gln Leu Val Asp
                355                 360                 365

Met Ala Ala Gln Ile Ala Ala Gly Met Ala Tyr Ile Glu Arg Met Asn
                370                 375                 380

Tyr Ile His Arg Asp Leu Arg Ala Ala Asn Ile Leu Val Gly Asp Asn
385                 390                 395                 400

Leu Val Cys Lys Ile Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
                420                 425                 430

Ala Pro Glu Ala Ala Leu Phe Gly Lys Phe Thr Ile Lys Ser Asp Val
                435                 440                 445

Trp Ser Phe Gly Ile Leu Leu Thr Glu Leu Val Thr Lys Gly Arg Val
450                 455                 460

Pro Tyr Pro Gly Met Asn Asn Arg Glu Val Leu Glu Gln Val Glu Arg
465                 470                 475                 480

Gly Tyr Arg Met Gln Cys Pro Gly Gly Cys Pro Pro Ser Leu His Asp
                485                 490                 495

Val Met Val Gln Cys Trp Lys Arg Glu Pro Glu Glu Arg Pro Thr Phe
                500                 505                 510

Glu Tyr Leu Gln Ser Phe Leu Glu Asp Tyr Phe Thr Ala Thr Glu Pro
            515                 520                 525

Gln Tyr Gln Pro Gly Asp Asn Gln
    530                 535
```

(2) INFORMATION FOR SEQ ID NO:13:

(i) SEQUENCE CHARACTERISTICS:

(A) LENGTH: 536 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:13:

Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Ala Phe
            20                  25                  30

Pro Ala Ser Gln Thr Pro Ser Lys Pro Ala Ser Ala Asp Gly His Arg
            35                  40                  45

Gly Pro Ser Ala Ala Phe Ala Pro Ala Ala Glu Pro Lys Leu Phe
50                      55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
                100                 105                 110

Ile Val Asn Asn Thr Glu Gly Asp Trp Trp Leu Ala His Ser Leu Ser
            115                 120                 125

Thr Gly Gln Thr Gly Tyr Ile Pro Ser Asn Tyr Val Ala Pro Ser Asp
        130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
        275                 280                 285

Trp Asn Gly Thr Thr Arg Val Ala Ile Lys Thr Leu Lys Pro Gly Thr
290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
        355                 360                 365

Met Ala Ala Gln Ile Ala Ser Gly Met Ala Tyr Val Glu Arg Met Asn

-continued

```
                370             375             380
    Tyr Val His Arg Asp Leu Arg Ala Ala Asn Ile Leu Val Gly Glu Asn
    385                 390                 395                 400

Leu Val Cys Lys Val Ala Asp Phe Gly Leu Ala Arg Leu Ile Glu Asp
                    405                 410                 415

Asn Glu Tyr Thr Ala Arg Gln Gly Ala Lys Phe Pro Ile Lys Trp Thr
                420                 425                 430

Ala Pro Glu Ala Ala Leu Tyr Gly Arg Phe Thr Ile Lys Ser Asp Val
                435                 440                 445

Trp Ser Phe Gly Ile Leu Leu Thr Glu Leu Thr Thr Lys Gly Arg Val
                450                 455                 460

Pro Tyr Pro Gly Met Val Asn Arg Glu Val Leu Asp Gln Val Glu Arg
    465                 470                 475                 480

Gly Tyr Arg Met Pro Cys Pro Pro Glu Cys Pro Glu Ser Leu His Asp
                    485                 490                 495

Leu Met Cys Gln Cys Trp Arg Lys Glu Pro Glu Glu Arg Pro Thr Phe
                    500                 505                 510

Glu Tyr Leu Gln Ala Phe Leu Glu Asp Tyr Phe Thr Ser Thr Glu Pro
                    515                 520                 525

Gln Tyr Gln Pro Gly Glu Asn Leu
                    530             535
```

(2) INFORMATION FOR SEQ ID NO:14:

(i) SEQUENCE CHARACTERISTICS:
        (A) LENGTH: 543 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:14:

```
    Met Gly Cys Ile Lys Ser Lys Glu Asn Lys Ser Pro Ala Ile Lys Tyr
    1               5                   10                  15

Arg Pro Glu Asn Thr Pro Glu Pro Val Ser Thr Ser Val Ser His Tyr
                    20                  25                  30

Gly Ala Glu Pro Thr Thr Val Ser Pro Cys Pro Ser Ser Ser Ala Lys
                35                  40                  45

Gly Thr Ala Val Asn Phe Ser Ser Leu Ser Met Thr Pro Phe Gly Gly
            50                  55                  60

Ser Ser Gly Val Thr Pro Phe Gly Gly Ala Ser Ser Ser Phe Ser Val
    65                  70                  75                  80

Val Pro Ser Ser Tyr Pro Ala Gly Leu Thr Gly Gly Val Thr Ile Phe
                    85                  90                  95

Val Ala Leu Tyr Asp Tyr Glu Ala Arg Thr Thr Glu Asp Leu Ser Phe
                    100                 105                 110

Lys Lys Gly Glu Arg Phe Gln Ile Ile Asn Asn Thr Glu Gly Asp Trp
                115                 120                 125

Trp Glu Ala Arg Ser Ile Ala Thr Gly Lys Asn Gly Tyr Ile Pro Ser
            130                 135                 140

Asn Tyr Val Ala Pro Ala Asp Ser Ile Gln Ala Glu Glu Trp Tyr Phe
    145                 150                 155                 160

Gly Lys Met Gly Arg Lys Asp Ala Glu Arg Leu Leu Leu Asn Pro Gly
                    165                 170                 175

Asn Gln Arg Gly Ile Phe Leu Val Arg Glu Ser Glu Thr Thr Lys Gly
```

-continued

```
                180                 185                 190
Ala Tyr Ser Leu Ser Ile Arg Asp Trp Asp Glu Ile Arg Gly Asp Asn
            195                 200                 205

Val Lys His Tyr Lys Ile Arg Lys Leu Asp Asn Gly Gly Tyr Tyr Ile
210                 215                 220

Thr Thr Arg Ala Gln Phe Asp Thr Leu Gln Lys Leu Val Lys His Tyr
225                 230                 235                 240

Thr Glu His Ala Asp Gly Leu Cys His Lys Leu Thr Thr Val Cys Pro
            245                 250                 255

Thr Val Lys Pro Gln Thr Gln Gly Leu Ala Lys Asp Ala Trp Glu Ile
            260                 265                 270

Pro Arg Glu Ser Leu Arg Leu Glu Val Lys Leu Gly Gln Gly Cys Phe
            275                 280                 285

Gly Glu Val Trp Met Gly Thr Trp Asn Gly Thr Thr Lys Val Ala Ile
            290                 295                 300

Lys Thr Leu Lys Pro Gly Thr Met Met Pro Glu Ala Phe Leu Gln Glu
305                 310                 315                 320

Ala Gln Ile Met Lys Lys Leu Arg His Asp Lys Leu Val Pro Leu Tyr
            325                 330                 335

Ala Val Val Ser Glu Glu Pro Ile Tyr Ile Val Thr Glu Phe Met Ser
            340                 345                 350

Lys Gly Ser Leu Leu Asp Phe Leu Lys Glu Gly Asp Gly Lys Tyr Leu
            355                 360                 365

Lys Leu Pro Gln Leu Val Asp Met Ala Ala Gln Ile Ala Asp Gly Met
            370                 375                 380

Ala Tyr Ile Glu Arg Met Asn Tyr Ile His Arg Asp Leu Arg Ala Ala
385                 390                 395                 400

Asn Ile Leu Val Gly Glu Asn Leu Val Cys Lys Ile Ala Asp Phe Gly
            405                 410                 415

Leu Ala Arg Leu Ile Glu Asp Asn Glu Tyr Thr Ala Arg Gln Gly Ala
            420                 425                 430

Lys Phe Pro Ile Lys Trp Thr Ala Pro Glu Ala Ala Leu Tyr Gly Arg
            435                 440                 445

Phe Thr Ile Lys Ser Asp Val Trp Ser Phe Gly Ile Leu Gln Thr Glu
            450                 455                 460

Leu Val Thr Lys Gly Arg Val Pro Tyr Pro Gly Met Val Asn Arg Glu
465                 470                 475                 480

Val Leu Glu Gln Val Glu Arg Gly Tyr Arg Met Pro Cys Pro Gln Gly
                    485                 490                 495

Cys Pro Glu Ser Leu His Glu Leu Met Asn Leu Cys Trp Lys Lys Asp
            500                 505                 510

Pro Asp Glu Arg Pro Thr Phe Glu Tyr Ile Gln Ser Phe Leu Glu Asp
            515                 520                 525

Tyr Phe Thr Ala Thr Glu Pro Gln Tyr Gln Pro Gly Glu Asn Leu
            530                 535                 540
```

(2) INFORMATION FOR SEQ ID NO:15:

(i) SEQUENCE CHARACTERISTICS:
        (A) LENGTH: 529 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:15:

```
Met Gly Cys Val Phe Cys Lys Lys Leu Glu Pro Val Ala Thr Ala Lys
 1               5                  10                  15

Glu Asp Ala Gly Leu Glu Gly Asp Phe Arg Ser Tyr Gly Ala Ala Asp
             20                  25                  30

His Tyr Gly Pro Asp Pro Thr Lys Ala Arg Pro Ala Ser Ser Phe Ala
             35                  40                  45

His Ile Pro Asn Tyr Ser Asn Phe Ser Ser Gln Ala Ile Asn Pro Gly
 50                  55                  60

Phe Leu Asp Ser Gly Thr Ile Arg Gly Val Ser Gly Ile Gly Val Thr
 65                  70                  75                  80

Leu Phe Ile Ala Leu Tyr Asp Tyr Glu Ala Arg Thr Glu Asp Asp Leu
             85                  90                  95

Thr Phe Thr Lys Gly Glu Lys Phe His Ile Leu Asn Asn Thr Glu Gly
             100                 105                 110

Asp Trp Trp Glu Ala Arg Ser Leu Ser Ser Gly Lys Thr Gly Cys Ile
             115                 120                 125

Pro Ser Asn Tyr Val Ala Pro Val Asp Ser Ile Gln Ala Glu Glu Trp
 130                 135                 140

Tyr Phe Gly Lys Ile Gly Arg Lys Asp Ala Glu Arg Gln Leu Leu Ser
145                 150                 155                 160

Pro Gly Asn Pro Gln Gly Ala Phe Leu Ile Arg Glu Ser Glu Thr Thr
             165                 170                 175

Lys Gly Ala Tyr Ser Leu Ser Ile Arg Asp Trp Asp Gln Thr Arg Gly
             180                 185                 190

Asp His Val Lys His Tyr Lys Ile Arg Lys Leu Asp Met Gly Gly Tyr
             195                 200                 205

Tyr Ile Thr Thr Arg Val Gln Phe Asn Ser Val Gln Glu Leu Val Gln
 210                 215                 220

His Tyr Met Glu Val Asn Asp Gly Leu Cys Asn Leu Leu Ile Ala Pro
225                 230                 235                 240

Cys Thr Ile Met Lys Pro Gln Thr Leu Gly Leu Ala Lys Asp Ala Trp
             245                 250                 255

Glu Ile Ser Arg Ser Ser Ile Thr Leu Glu Arg Arg Leu Gly Thr Gly
             260                 265                 270

Cys Phe Gly Asp Val Trp Leu Gly Thr Trp Asn Gly Ser Thr Lys Val
             275                 280                 285

Ala Val Lys Thr Leu Lys Pro Gly Thr Met Ser Pro Lys Ala Phe Leu
 290                 295                 300

Glu Glu Ala Gln Val Met Lys Leu Leu Arg His Asp Lys Leu Val Gln
305                 310                 315                 320

Leu Tyr Ala Val Val Ser Glu Glu Pro Ile Tyr Ile Val Thr Glu Phe
             325                 330                 335

Met Cys His Gly Ser Leu Leu Asp Phe Leu Lys Asn Pro Glu Gly Gln
             340                 345                 350

Asp Leu Arg Leu Pro Gln Leu Val Asp Met Ala Ala Gln Val Ala Glu
             355                 360                 365

Gly Met Ala Tyr Met Glu Arg Met Asn Tyr Ile His Arg Asp Leu Arg
 370                 375                 380

Ala Ala Asn Ile Leu Val Gly Glu Arg Leu Ala Cys Lys Ile Ala Asp
385                 390                 395                 400

Phe Gly Leu Ala Arg Leu Ile Lys Asp Asp Glu Tyr Asn Pro Cys Gln
             405                 410                 415
```

```
Gly Ser Lys Phe Pro Ile Lys Trp Thr Ala Pro Glu Ala Ala Leu Phe
            420                 425                 430

Gly Arg Phe Thr Ile Lys Ser Asp Val Trp Ser Phe Gly Ile Leu Leu
        435                 440                 445

Thr Glu Leu Ile Thr Lys Gly Arg Ile Pro Tyr Pro Gly Met Asn Lys
        450                 455                 460

Arg Glu Val Leu Glu Gln Val Glu Gln Gly Tyr His Met Pro Cys Pro
465                 470                 475                 480

Pro Gly Cys Pro Ala Ser Leu Tyr Glu Ala Met Glu Gln Thr Trp Arg
                485                 490                 495

Leu Asp Pro Glu Glu Arg Pro Thr Phe Glu Tyr Leu Gln Ser Phe Leu
            500                 505                 510

Glu Asp Tyr Phe Thr Ser Ala Glu Pro Gln Tyr Gln Pro Gly Asp Gln
            515                 520                 525

Thr
```

(2) INFORMATION FOR SEQ ID NO:16:

(i) SEQUENCE CHARACTERISTICS:
        (A) LENGTH: 512 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:16:

```
Met Gly Cys Ile Lys Ser Lys Gly Lys Asp Ser Leu Ser Asp Asp Gly
1               5                   10                  15

Val Asp Leu Lys Thr Gln Pro Val Arg Asn Thr Glu Arg Thr Ile Tyr
            20                  25                  30

Val Arg Asp Pro Thr Ser Asn Lys Gln Gln Arg Pro Val Pro Glu Ser
        35                  40                  45

Gln Leu Leu Pro Gly Gln Arg Phe Gln Thr Lys Asp Pro Glu Glu Gln
50                  55                  60

Gly Asp Ile Val Val Ala Leu Tyr Pro Tyr Asp Gly Ile His Pro Asp
65                  70                  75                  80

Asp Leu Ser Phe Lys Lys Gly Glu Lys Met Lys Val Leu Glu Glu His
                85                  90                  95

Gly Glu Trp Trp Lys Ala Lys Ser Leu Leu Thr Lys Lys Glu Gly Phe
            100                 105                 110

Ile Pro Ser Asn Tyr Val Ala Lys Leu Asn Thr Leu Glu Thr Glu Glu
        115                 120                 125

Trp Phe Phe Lys Asp Ile Thr Arg Lys Asp Ala Glu Arg Gln Leu Leu
130                 135                 140

Ala Pro Gly Asn Ser Ala Gly Ala Phe Leu Ile Arg Glu Ser Glu Thr
145                 150                 155                 160

Leu Lys Gly Ser Phe Ser Leu Ser Val Arg Asp Phe Asp Pro Val His
            165                 170                 175

Gly Asp Val Ile Lys His Tyr Lys Ile Arg Ser Leu Asp Asn Gly Gly
        180                 185                 190

Tyr Tyr Ile Ser Pro Arg Ile Thr Phe Pro Cys Ile Ser Asp Met Ile
        195                 200                 205

Lys His Tyr Gln Lys Gln Ala Asp Gly Leu Cys Arg Arg Leu Glu Lys
210                 215                 220
```

```
Ala Cys Ile Ser Pro Lys Pro Gln Lys Pro Trp Asp Lys Asp Ala Trp
225                 230                 235                 240

Glu Ile Pro Arg Glu Ser Ile Lys Leu Val Lys Arg Leu Gly Ala Gly
                245                 250                 255

Gln Phe Gly Glu Val Trp Met Gly Tyr Tyr Asn Asn Ser Thr Lys Val
                260                 265                 270

Ala Val Lys Thr Leu Lys Pro Gly Thr Met Ser Val Gln Ala Phe Leu
            275                 280                 285

Glu Glu Ala Asn Leu Met Lys Thr Leu Gln His Asp Lys Leu Val Arg
        290                 295                 300

Leu Tyr Ala Val Val Thr Arg Glu Glu Pro Ile Tyr Ile Ile Thr Glu
305                 310                 315                 320

Tyr Met Ala Lys Gly Ser Leu Leu Asp Phe Leu Lys Ser Asp Glu Gly
                325                 330                 335

Gly Lys Val Leu Leu Pro Lys Leu Ile Asp Phe Ser Ala Gln Ile Ala
                340                 345                 350

Glu Gly Met Ala Tyr Ile Glu Arg Lys Asn Tyr Ile His Arg Asp Leu
            355                 360                 365

Arg Ala Ala Asn Val Leu Val Ser Glu Ser Leu Met Cys Lys Ile Ala
370                 375                 380

Asp Phe Gly Leu Ala Arg Val Ile Glu Asp Asn Glu Tyr Thr Ala Arg
385                 390                 395                 400

Glu Gly Ala Lys Phe Pro Ile Lys Trp Thr Ala Pro Glu Ala Ile Asn
                405                 410                 415

Phe Gly Cys Phe Thr Ile Lys Ser Asp Val Trp Ser Phe Gly Ile Leu
                420                 425                 430

Leu Tyr Glu Ile Val Thr Tyr Gly Lys Ile Pro Tyr Pro Gly Arg Thr
            435                 440                 445

Asn Ala Asp Val Met Thr Ala Leu Ser Gln Gly Tyr Arg Met Pro Arg
                450                 455                 460

Val Glu Asn Cys Pro Asp Glu Leu Tyr Asp Ile Met Lys Met Cys Trp
465                 470                 475                 480

Lys Glu Lys Ala Glu Glu Arg Pro Thr Phe Asp Tyr Leu Gln Ser Val
                485                 490                 495

Leu Asp Asp Phe Tyr Thr Ala Thr Glu Gly Gln Tyr Gln Gln Gln Pro
                500                 505                 510

(2) INFORMATION FOR SEQ ID NO:17:

(i) SEQUENCE CHARACTERISTICS:
        (A) LENGTH: 505 amino acids
        (B) TYPE: amino acid
        (C) STRANDEDNESS: unknown
        (D) TOPOLOGY: unknown (xi) SEQUENCE DESCRIPTION: SEQ ID NO:17:

Met Gly Ser Met Lys Ser Lys Phe Leu Gln Val Gly Gly Asn Thr Phe
1               5                   10                  15

Ser Lys Thr Glu Thr Ser Ala Ser Pro His Cys Pro Val Tyr Val Pro
            20                  25                  30

Asp Pro Thr Ser Thr Ile Lys Pro Gly Pro Asn Ser His Asn Ser Asn
        35                  40                  45

Thr Pro Gly Ile Arg Glu Ala Gly Ser Glu Asp Ile Ile Val Val Ala
    50                  55                  60

Leu Tyr Asp Tyr Glu Ala Ile His His Glu Asp Leu Ser Phe Gln Lys
65                  70                  75                  80
```

-continued

```
Gly Asp Gln Met Val Val Leu Glu Glu Ser Gly Glu Trp Trp Lys Ala
                85                  90                  95
Arg Ser Leu Ala Thr Arg Lys Glu Gly Tyr Ile Pro Ser Asn Tyr Val
            100                 105                 110
Ala Arg Val Asp Ser Leu Glu Thr Glu Glu Trp Phe Phe Lys Gly Ile
        115                 120                 125
Ser Arg Lys Asp Ala Glu Arg Gln Leu Leu Ala Pro Gly Asn Met Leu
    130                 135                 140
Gly Ser Phe Met Ile Arg Asp Ser Glu Thr Thr Lys Gly Ser Tyr Ser
145                 150                 155                 160
Leu Ser Val Arg Asp Tyr Asp Pro Arg Gln Gly Asp Thr Val Lys His
                165                 170                 175
Tyr Lys Ile Arg Thr Leu Asp Asn Gly Gly Phe Tyr Ile Ser Pro Arg
            180                 185                 190
Ser Thr Phe Ser Thr Leu Gln Glu Leu Val Asp His Tyr Lys Lys Gly
        195                 200                 205
Asn Asp Gly Leu Cys Gln Lys Leu Ser Val Pro Cys Met Ser Ser Lys
    210                 215                 220
Pro Gln Lys Pro Trp Glu Lys Asp Ala Trp Glu Ile Pro Arg Glu Ser
225                 230                 235                 240
Leu Lys Leu Glu Lys Lys Leu Gly Ala Gly Gln Phe Gly Glu Val Trp
                245                 250                 255
Met Ala Thr Tyr Asn Lys His Thr Lys Val Ala Val Lys Thr Met Lys
            260                 265                 270
Pro Gly Ser Met Ser Val Glu Ala Phe Leu Ala Glu Ala Asn Val Met
        275                 280                 285
Lys Thr Leu Gln His Asp Lys Leu Val Lys Leu His Ala Val Val Thr
    290                 295                 300
Lys Glu Pro Ile Tyr Ile Ile Thr Glu Phe Met Ala Lys Gly Ser Leu
305                 310                 315                 320
Leu Asp Phe Leu Lys Ser Asp Glu Gly Ser Lys Gln Pro Leu Pro Lys
                325                 330                 335
Leu Ile Asp Phe Ser Ala Gln Ile Ala Glu Gly Met Ala Phe Ile Glu
            340                 345                 350
Gln Arg Asn Tyr Ile His Arg Asp Leu Arg Ala Ala Asn Ile Leu Val
        355                 360                 365
Ser Ala Ser Leu Val Cys Lys Ile Ala Asp Phe Gly Leu Ala Arg Val
    370                 375                 380
Ile Glu Asp Asn Glu Tyr Thr Ala Arg Glu Gly Ala Lys Phe Pro Ile
385                 390                 395                 400
Lys Trp Thr Ala Pro Glu Ala Ile Asn Phe Gly Ser Phe Thr Ile Lys
                405                 410                 415
Ser Asp Val Trp Ser Phe Gly Ile Leu Leu Met Glu Ile Val Thr Tyr
            420                 425                 430
Gly Arg Ile Pro Tyr Pro Gly Met Ser Asn Pro Glu Val Ile Arg Ala
        435                 440                 445
Leu Glu Arg Gly Tyr Arg Met Pro Arg Pro Glu Asn Cys Pro Glu Glu
    450                 455                 460
Leu Tyr Asn Ile Met Met Arg Cys Trp Lys Asn Arg Pro Glu Glu Arg
465                 470                 475                 480
Pro Thr Phe Glu Tyr Ile Gln Ser Val Leu Asp Asp Phe Tyr Thr Ala
                485                 490                 495
```

```
Thr Glu Ser Gln Tyr Gln Gln Gln Pro
            500             505
```

(2) INFORMATION FOR SEQ ID NO:18:

(i) SEQUENCE CHARACTERISTICS:
        (A) LENGTH: 509 amino acids
        (B) TYPE: amino acid
        (C) STRANDEDNESS: unknown
        (D) TOPOLOGY: unknown (xi) SEQUENCE DESCRIPTION: SEQ ID NO:18:

```
Met Gly Cys Gly Cys Ser Ser His Pro Glu Asp Trp Met Glu Asn
 1               5                  10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
                35                  40                  45

Val Thr Tyr Glu Gly Ser Asn Pro Pro Ala Ser Pro Leu Gln Asp Asn
         50                  55                  60

Leu Val Ile Ala Leu His Ser Tyr Glu Pro Ser His Asp Gly Asp Leu
 65                  70                  75                  80

Gly Phe Glu Lys Gly Glu Gln Leu Arg Ile Leu Glu Gln Ser Gly Glu
                    85                  90                  95

Trp Trp Lys Ala Gln Ser Leu Thr Thr Gly Gln Glu Gly Phe Ile Pro
                100                 105                 110

Phe Asn Phe Val Ala Lys Ala Asn Ser Leu Glu Pro Glu Pro Trp Phe
                115                 120                 125

Phe Lys Asn Leu Ser Arg Lys Asp Ala Glu Arg Gln Leu Leu Ala Pro
                130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
                180                 185                 190

Ile Ser Pro Arg Ile Thr Phe Pro Gly Leu His Glu Leu Val Arg His
                195                 200                 205

Tyr Thr Asn Ala Ser Asp Gly Leu Cys Thr Arg Leu Ser Arg Pro Cys
    210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
                260                 265                 270

Lys Ser Leu Lys Gln Gly Ser Met Ser Pro Asp Ala Phe Leu Ala Glu
            275                 280                 285

Ala Asn Leu Met Lys Gln Leu Gln His Gln Arg Leu Val Arg Leu Tyr
290                 295                 300

Ala Val Val Thr Gln Glu Pro Ile Tyr Ile Ile Thr Glu Tyr Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
                340                 345                 350
```

```
Ala Phe Ile Glu Glu Arg Asn Tyr Ile His Arg Asp Leu Arg Ala Ala
        355                 360                 365

Asn Ile Leu Val Ser Asp Thr Leu Ser Cys Lys Ile Ala Asp Phe Gly
        370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415

Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
            435                 440                 445

Val Ile Gln Asn Leu Glu Arg Gly Tyr Arg Met Val Arg Pro Asp Asn
450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
            500                 505

(2) INFORMATION FOR SEQ ID NO:19:

(i) SEQUENCE CHARACTERISTICS:
        (A) LENGTH: 499 amino acids
        (B) TYPE: amino acid
        (C) STRANDEDNESS: unknown
        (D) TOPOLOGY: unknown (ii) MOLECULE TYPE: None (xi) SEQUENCE DESCRIPTION: SEQ ID NO:19:

Met Gly Leu Leu Ser Ser Lys Arg Gln Val Ser Glu Lys Gly Lys Gly
1               5                   10                  15

Trp Ser Pro Val Lys Ile Arg Thr Gln Asp Lys Ala Pro Pro Pro Leu
            20                  25                  30

Pro Pro Leu Val Val Phe Asn His Leu Ala Pro Pro Ser Pro Asn Gln
            35                  40                  45

Asp Pro Asp Glu Glu Glu Arg Phe Val Val Ala Leu Phe Asp Tyr Ala
50                  55                  60

Ala Val Asn Asp Arg Asp Leu Gln Val Leu Lys Gly Glu Lys Leu Gln
65                  70                  75                  80

Val Leu Arg Ser Thr Gly Asp Trp Trp Leu Ala Arg Ser Leu Val Thr
                85                  90                  95

Gly Arg Glu Gly Tyr Val Pro Ser Asn Phe Val Ala Pro Val Glu Thr
            100                 105                 110

Leu Glu Val Glu Lys Trp Phe Phe Arg Thr Ile Ser Arg Lys Asp Ala
            115                 120                 125

Glu Arg Gln Leu Leu Ala Pro Met Asn Lys Ala Gly Ser Phe Leu Ile
        130                 135                 140

Arg Glu Ser Glu Ser Asn Lys Gly Ala Phe Ser Leu Ser Val Lys Asp
145                 150                 155                 160

Ile Thr Thr Gln Gly Glu Val Val Lys His Tyr Lys Ile Arg Ser Leu
                165                 170                 175

Asp Asn Gly Gly Tyr Tyr Ile Ser Pro Arg Ile Thr Phe Pro Thr Leu
            180                 185                 190
```

```
Gln Ala Leu Val Gln His Tyr Ser Lys Lys Gly Asp Gly Leu Cys Gln
            195                 200                 205
Lys Leu Thr Leu Pro Cys Val Asn Leu Ala Pro Lys Asn Leu Trp Ala
    210                 215                 220
Gln Asp Glu Trp Glu Ile Pro Arg Gln Ser Leu Lys Leu Val Arg Lys
225                 230                 235                 240
Leu Gly Ser Gly Gln Phe Gly Glu Val Trp Met Gly Tyr Tyr Lys Asn
                245                 250                 255
Asn Met Lys Val Ala Ile Lys Thr Leu Lys Glu Gly Thr Met Ser Pro
            260                 265                 270
Glu Ala Phe Leu Gly Glu Ala Asn Val Met Lys Thr Leu Gln His Glu
        275                 280                 285
Arg Leu Val Arg Leu Tyr Ala Val Val Thr Arg Glu Pro Ile Tyr Ile
    290                 295                 300
Val Thr Glu Tyr Met Ala Arg Gly Cys Leu Leu Asp Phe Leu Lys Thr
305                 310                 315                 320
Asp Glu Gly Ser Arg Leu Ser Leu Pro Arg Leu Ile Asp Met Ser Ala
                325                 330                 335
Gln Val Ala Glu Gly Met Ala Tyr Ile Glu Arg Met Asn Ser Ile His
            340                 345                 350
Arg Asp Leu Arg Ala Ala Asn Ile Leu Val Ser Glu Thr Leu Cys Cys
        355                 360                 365
Lys Ile Ala Asp Phe Gly Leu Ala Arg Ile Ile Asp Ser Glu Tyr Thr
    370                 375                 380
Ala Gln Glu Gly Ala Lys Phe Pro Ile Lys Trp Thr Ala Pro Glu Ala
385                 390                 395                 400
Ile His Phe Gly Val Phe Thr Ile Lys Ala Asp Val Trp Ser Phe Gly
                405                 410                 415
Val Leu Leu Met Val Ile Val Thr Tyr Gly Arg Val Pro Tyr Pro Gly
            420                 425                 430
Met Ser Asn Pro Glu Val Ile Arg Ser Leu Glu His Gly Tyr Arg Met
        435                 440                 445
Pro Cys Pro Glu Thr Cys Pro Pro Glu Leu Tyr Asn Asp Ile Ile Thr
    450                 455                 460
Glu Cys Trp Arg Gly Arg Pro Glu Glu Arg Pro Thr Phe Glu Phe Leu
465                 470                 475                 480
Gln Ser Val Leu Glu Asp Phe Tyr Thr Ala Thr Glu Gly Gln Tyr Glu
                485                 490                 495
Leu Gln Pro (2) INFORMATION FOR SEQ ID NO:20:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (xi) SEQUENCE DESCRIPTION: SEQ ID NO:20:

GGAATTCCCA CAGNGACTTN GCNGCNAG                                            28

(2) INFORMATION FOR SEQ ID NO:21:

(i) SEQUENCE CHARACTERISTICS:
        (A) LENGTH: 26 base pairs
        (B) TYPE: nucleic acid
```

```
            (C) STRANDEDNESS: unknown
            (D) TOPOLOGY: unknown (ii) MOLECULE TYPE: cDNA (xi) SEQUENCE DESCRIPTION: SEQ ID NO:21:

GGAATTCCGA ANGTCCANAC GTCNGA                                              26
```

MEGAKARYOCYTIC PROTEIN TYROSINE KINASES

This application is a continuation-in-part application of U.S. application Ser. No. 08/232,545, filed Apr. 22, 1994, which is incorporated herein by reference.

TABLE OF CONTENTS

1. Introduction
2. Background
3. Summary of the Invention
4. Brief Description of the Figures
5. Detailed Description
    5.1. The MKK Coding Sequences
    5.2. Expression of MKK
    5.3. Expression Systems
    5.4. Identification of Transfectants or Transformants that Express the MKK
    5.5. Uses of MKK and Engineered Cell Lines
        5.5.1. Antibody Production and Screening
        5.5.2. Screening of Peptide Library with MKK or MKK Engineered Cell Lines
        5.5.3. Screening of Organic Compounds with MKK Protein or Engineered Cell Lines
    5.6. Uses of MKK Polynucleotide
        5.6.1. Diagnostic Uses of an MKK Polynucleotide
        5.6.2. Therapeutic Uses of an MKK Polynucleotide
6. Examples: Cloning and Characterization of MKK1
    6.1. cDNA Cloning, MKK Expression and MKK Characterization
        6.1.1. Full-length cDNA Cloning
        6.1.2. MKK Expression
        6.1.3. RNA Blot Analysis of MKKs
7. Example: Autophosphorylation of MKK2 and MKK3
8. Example: Production of Anti-MKK Antibodies and Immunoprecipitation of MKK
9. Example: Expression of MKK1 Anti-sense Sequences
10. Example: MKKR Protein Tyrosine Kinase Activity
    10.1. Materials and Methods.
    10.2. Results
11. Example: Biological Activity of MKK1
    11.1. Materials and Methods
        11.1.1. Retroviral Infection of L-8057 cells
        11.1.2. Cell Growth Measurement of MKK1 Expressing L-8057 Cells
        11.1.3. Growth Factor Response of MKK1 Expressing L-8057 Cells
    11.2. Results
        11.2.1. Cell Growth
        11.2.2. Cytokine Stimulation
        11.2.3. Cell Differentiation
WHAT IS CLAIMED
ABSTRACT

1. Introduction

The present invention relates to novel cytoplasmic tyrosine kinases isolated from megakaryocytes (megakaryocyte kinases or MKKs) which are involved in cellular signal transduction pathways and to the use of these novel proteins in the diagnosis and treatment of disease.

The present invention further relates to specific megakaryocyte kinases, designated MKK1, MKK2 and MKK3, and their use as diagnostic and therapeutic agents.

2. Background

Cellular signal transduction is a fundamental mechanism whereby external stimuli that regulate diverse cellular processes are relayed to the interior of cells. These processes include, but are not limited to, cell proliferation, differentiation and survival. Many tyrosine kinases are expressed in postmitotic, fully differentiated cells, particularly in the case of hematopoietic cells, and it seems likely that these proteins are involved in specialized cellular functions that are specific for the cell types in which they are expressed. (Eiseman, E. and J. B. Bolen, *Cancer Cells* 2(10):303–310, 1990). A central feature of signal transduction is the reversible phosphorylation of certain proteins. (for reviews, see Posada, J. and Cooper, J. A., 1992, *Mol. Biol. Cell* 3:583–392; Hardie, D. G., 1990, *Symp. Soc. Exp. Biol.* 44:241–255). The phosphorylation state of a protein is modified through the reciprocal actions of tyrosine kinases (TKs), which function to phosphorylate proteins, and tyrosine phosphatases (TPs), which function to dephosphorylate proteins. Normal cellular function requires a delicate balance between the activities of these two types of enzyme.

Phosphorylation of cell surface tyrosine kinases, stimulates a physical association of the activated receptor with intracellular target molecules. Some of the target molecules are in turn phosphorylated. Other target molecules are not phosphorylated, but assist in signal transmission by acting as adapter molecules for secondary signal transducer proteins. The secondary signal transducer molecules generated by activated receptors result in a signal cascade that regulates cell functions such as cell division or differentiation. Reviews describing intracellular signal transduction include Aaronson, S. A., *Science* 254:1146–1153, 1991; Schlessinger, J. *Trends Biochem. Sci.* 13:443–447, 1988; and Ullrich, A., and Schlessinger, *J. Cell* 61:203–212, 1990.

Receptor tyrosine kinases are composed of at least three domains: an extracellular ligand binding domain, a transmembrane domain and a cytoplasmic catalytic domain that can phosphorylate tyrosine residues. The intracellular, cytoplasmic, nonreceptor protein tyrosine kinases may be broadly defined as those protein tyrosine kinases which do not contain a hydrophobic, transmembrane domain. Bolen (*Oncogene*, vol. 8, pgs. 2025–2031 (1993)) reports that 24 individual protein tyrosine kinases comprising eight different families of non-receptor protein tyrosine kinases have been identified: Abl/Arg; Jak1/Jak2/Tyk2; Fak; Fes/Fps; Syk/Zap; Tsk/Tec/Atk; Csk; and the Src group, which includes the family members Src, Yes, Fyn, Lyn, Lck, Blk, Hck, Fgr and Yrk. All of the non-receptor protein tyrosine kinases are thought to be involved in signaling pathways that modulate growth and differentiation. Bolen, supra, suggests that half of the nonreceptor protein tyrosine kinases have demonstrated oncogenic potential and half appear to be primarily related to suppressing the activity of Src-related protein kinases and could be classified as anti-oncogenes.

While distinct in their overall molecular structure, each member of a given morphotypic family of cytoplasmic protein tyrosine kinases shares sequence homology in certain non-catalytic domains in addition to sharing sequence homology in the catalytic kinase domain. Examples of defined non-catalytic domains include the SH2 (SRC homology domain 2; Sadowski, I et al., *Mol. Cell. Biol.* 6:4396–4408; Kock, C. A. et al., 1991, *Science* 252:668–674) domains, SH3 domains (Mayer, B. J. et al., 1988, *Nature* 332:269–272) and PH domains (Musacchio et al., *TIBS* 18:343–348 (1993). These non-catalytic domains are thought to be important in the regulation of protein-protein interactions during signal transduction (Pawson, T. and Gish, G., 1992, *Cell* 71:359–362).

While the metabolic roles of cytoplasmic protein tyrosine kinases are less well understood than that of the receptor-type protein tyrosine kinases, significant progress has been made in elucidating some of the processes in which this class of molecules is involved. For example, members of the src family, lck and fyn, have been shown to interact with CD4/CD8 and the T cell receptor complex, and are thus implicated in T cell activation, (Veillette, A. Davidson, D., 1992, *TIG* 8:61–66). Some cytoplasmic protein tyrosine kinases have been linked to certain phases of the cell cycle (Morgan, D. O. et al., 1989, *Cell* 57:775–786; Kipreos, E. T. et al., 1990, *Science* 248:217–220; Weaver et al., 1991, *Mol. Cell. Biol.* 11:4415–4422), and cytoplasmic protein tyrosine kinases have been implicated in neuronal and hematopoietic development (Maness, P., 1992, *Dev. Neurosci* 14:257–270 and Rawlings et al., *Science* 261:358–361 (1993)). Deregulation of kinase activity through mutation or overexpression is a well-established mechanism underlying cell transformation (Hunter et al., 1985, supra; Ullrich et al., supra).

A variety of cytoplasmic tyrosine kinases are expressed in, and may have important functions in, hematopoietic cells including src, lyn, fyn, blk, lck, csk and hck. (Eisenian, E. and J. B. Bolen, *Cancer Cells* 2(10):303–310, 1990). T-cell activation, for example, is associated with activation of lck. The signaling activity of lyn may be stimulated by binding of allergens to IgE on the surface of basophils. (Eisenian, supra).

Abnormalities in tyrosine kinase regulated signal transduction pathways can result in a number of disease states. For example, mutations in the cytoplasmic tyrosine kinase atk (also called btk) are responsible for the x-linked agammaglobulinemia, (Ventrie, D., et al., *Nature* 361:226–23, 1993). This defect appears to prevent the normal differentiation of pre-B cells to mature circulating B cells and results in a complete lack of serum immunoglobulins of all isotypes. The cytoplasmic tyrosine kinase Zap-70 has been suggested as indispensable for the development of CD8 single-positive T cells as well as for signal transduction and function of single-positive CD4 T cells, and lack of this protein leads to an immunodeficiency disease in humans, (Arpala, E., et al., *Cell* 76:1–20, 1994). Gene knockout experiments in mice suggest a role for src in the regulation of osteoclast function and bone remodeling as these mice develop osteopetrosis. (Soriano et al., *Cell* 64:693–702, 1991 and Lowe et al., PNAS (in press)).

Megakaryocytes are large cells normally present in bone marrow and spleen and are the progenitor cell for blood platelets. Megakaryocytes are associated with such disease states as acute megakaryocytic leukemia (Lu et al., *Cancer Genet Cytogenet*, 67(2):81–89 (1993) and Moody et al., *Pediatr Radiol.* 19(6–7):486–488 (1989)), a disease that is difficult to diagnose early and which is characterized by aberrant proliferation of immature cells or "blasts"; myelofibrosis (Smith et al., *Crit Rev Oncol Hematol.* 10(4):305–314 (1990) and Marino, *J. Am. Osteopath Assoc.* 10:1323–1326 (1989)), an often fatal disease where the malignant cell may be of megakaryocytic lineage and may be mediated by platelet or megakaryocyte growth factors; acute megakaryocytic myelosis (Fohlmeister et al., *Haematologia* 19(2): 151–160 (1986)) a rapidly fatal disease characterized by megakaryocytic proliferation and the appearance of immature megakaryocytes in the circulation; and acute myelosclerosis (Butler et al., *Cancer* 49(12):2497–2499 (1982) and Bearman et al., *Cancer* 43(1):279–93 (1979)) a myeloproliferative syndrome where the marrow is characterized by atypical megakaryocytes.

Platelets play a key role in the regulation of blood clotting and wound healing, as well as being associated with such disease conditions as thrombocytopenia, atherosclerosis, restenosis and leukemia. Several receptor tyrosine kinases have been identified in human megakaryocytes including c-kit, blg and blk. (Hoffman, H., *Blood* 74:1196–1212, 1989; Long, M. W., *Stem Cells* 11:33–40, 1993; Zaebo, K. M., et al., *Cell* 63:213–224,1990). Cytoplasmic tyrosine kinases of human megakaryocytic origin have also been reported. (Bennett et al., *Journal of Biological Chemistry* 289(2) :1068–1074, 1994; Lee et al., *Gene* 1–5, 1993; and Sakano et al., *Oncogene* 9:1155–1161 (1994)).

3. SUMMARY OF THE INVENTION

The present invention relates to novel, cytoplasmic tyrosine kinases isolated from megakaryocytes (megakaryocyte kinases or MKKs) which are involved in cellular signal transduction pathways. Particular MKKs described herein are referred to as MKK1, MKK2, and MKK3. The complete nucleotide sequences encoding MKK1, MKK2, and MKK3 are disclosed herein, and provide the basis for several aspects of the invention hereinafter described.

The present invention is based, in part, upon the discovery that MKK1, MKK2, and MKK3 have amino acid and structural homology, respectively, to the PTKs csk (Brauninger et al. *Gene*, 110:205–211 (1992) and Brauninger et al., *Oncogene*, 8:1365–1369 (1993)), atk/btk, tec and tsk (Vetrie et al., *Nature* 361:226–233 (1993); Mano et al., *Oncogene* 8:417–424 (1993) and Heyeck et al., *PNAS USA* 90:669–673,1993, respectively) and fyn (Kawakami et al. *Mol. Cell. Bio.* 6:4195–4201, 1986)).

The present invention also relates, in part, to nucleotide sequences and expression vectors encoding MKKs. Also described herein are methods of treatment and diagnosis of diseases resulting from abnormalities in signal transduction pathways in which MRKs are involved.

The MKK sequences disclosed herein may be used to detect and quantify levels of MKK mRNA in cells and furthermore for diagnostic purposes for detection of expression of MKKs in cells. For example, an MKK sequence may be used in hybridization assays of biopsied tissue to diagnose abnormalities in gene expression associated with a transformed phenotype.

Also disclosed herein are methods of treatment of diseases or conditions associated with abnormalities in signal transduction pathways in megakaryocytes. Such abnormalities can result in, for example, under production of mature, differentiated cells, inappropriate proliferation of immature cells or modulation of activity of other important cellular functions.

Anti-MKK antibodies may be used for diagnostic purposes for the detection of MKKs in tissues and cells. Anti-MKK antibodies may also be used for therapeutic purposes, for example, in neutralizing the activity of an MKK associated with a signal transduction pathway.

Oligonucleotide sequences, including anti-sense RNA and DNA molecules and ribozymes, designed to inhibit the translation of MKK mRNA, may be used therapeutically in the treatment of disease states associated with aberrant expression of MKKs. In a particular embodiment of the invention described by way of Example 9 herein, an anti-MKK1 antisense molecule is used to inhibit MKK-1 protein synthesis resulting in reduced megakaryocyte growth and differentiation.

Proteins, peptides and organic molecules capable of modulating activity of MKKs may be used therapeutically in the treatment of disease states associated with aberrant expression of MKKs. Alternatively, proteins, peptides and organic molecules capable of modulating activity of MKKs may be used therapeutically to enhance normal activity levels of MKKs. For example, small molecules found to stimulate MKK1 activity in megakaryocytes may be used for ex vivo culturing of megakaryocytes intended for autologous treatment of patients receiving chemotherapy or other therapies which deplete megakaryoctyes or platelets, or in the treatment of thrombocytopenia.

4. BRIEF DESCRIPTION OF THE FIGURES

FIGS. 1A and 1B. Human MKK1 nucleotide sequence (SEQ ID NO:1) and deduced amino acid sequence (SEQ ID NO:2). Marked regions show the SH2 and SH3 domains, and the catalytic domain.

FIGS. 2A and 2B. Human MKK2 nucleotide sequence (SEQ ID NO:3) and deduced amino acid sequence (SEQ ID NO:4). Marked regions show the pleckstrin homology domain (PH), the proline rich sequences following the PH domain, the SH2 and SH3 domains, and the catalytic domain.

FIGS. 3A and 3B. Human MKK3 nucleotide sequence (SEQ ID NO:5) and deduced amino acid sequence (SEQ ID NO:6). Marked regions show the SH2 and SH3 domains, and the catalytic domain.

FIG. 4. Expression of MKK1 and MKK2 in human and rodent cell lines.

FIG. 5. Immunoprecipitation (i.p.) of in vitro transcribed and translated MKK1 and MKK2 proteins. Samples in lanes designated 1 through 9 are as follows: 1. MKK1 i.p. with anti-carboxy terminus MKK1 Ab, 2. and 3. MKK1 i.p. with anti-amino terminus MKK1 Ab, 4. MKK1 i.p. with rabbit pre immune sera, 5. MKK2 i.p. with rabbit pre immune sera, 6. and 7. MKK2 i.p. with anti-carboxy terminus MKK2 Ab, 8. MKK1 in vitro transcribed/translated protein without i.p., 9. MKK2 in vitro transcribed/translated protein without i.p.

Figure 6A:
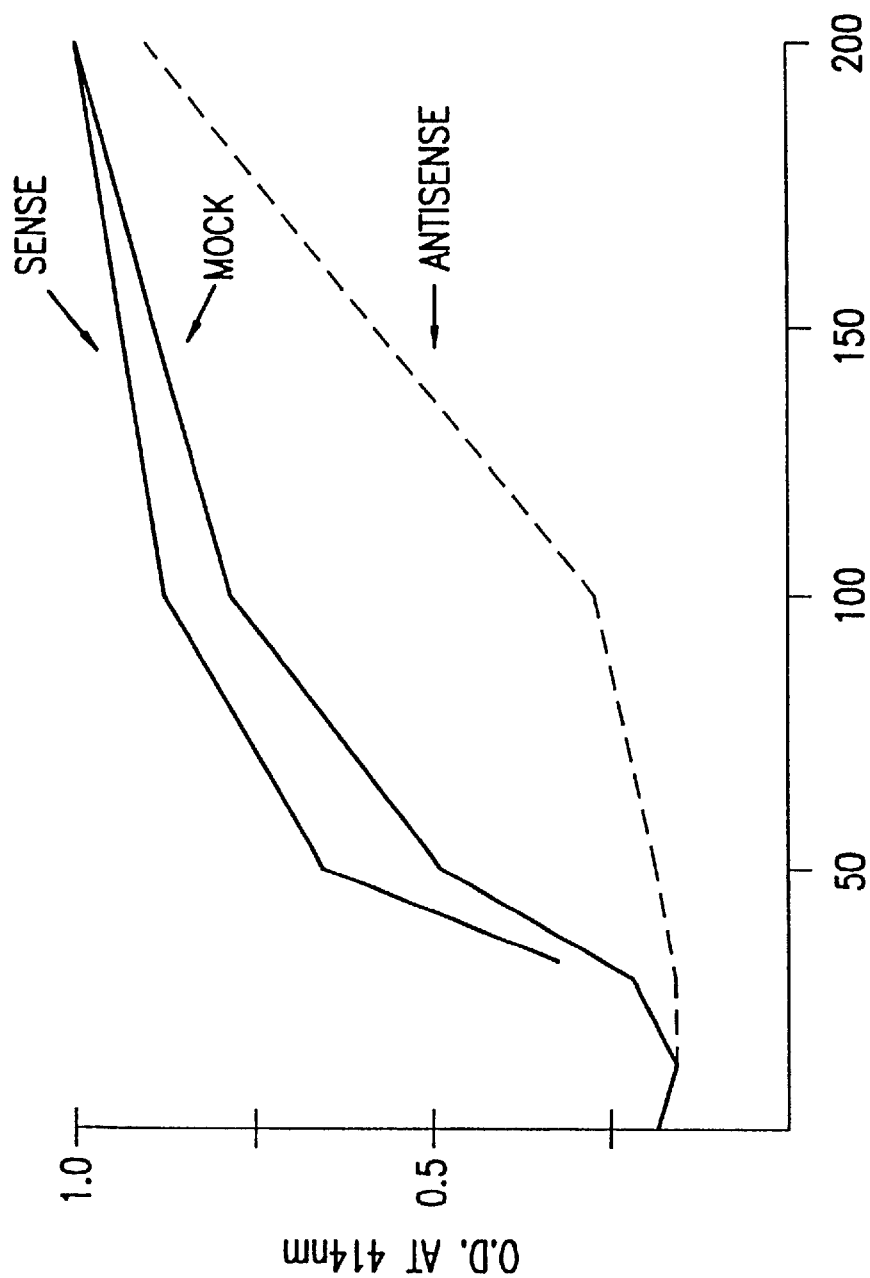
Figure 6B:
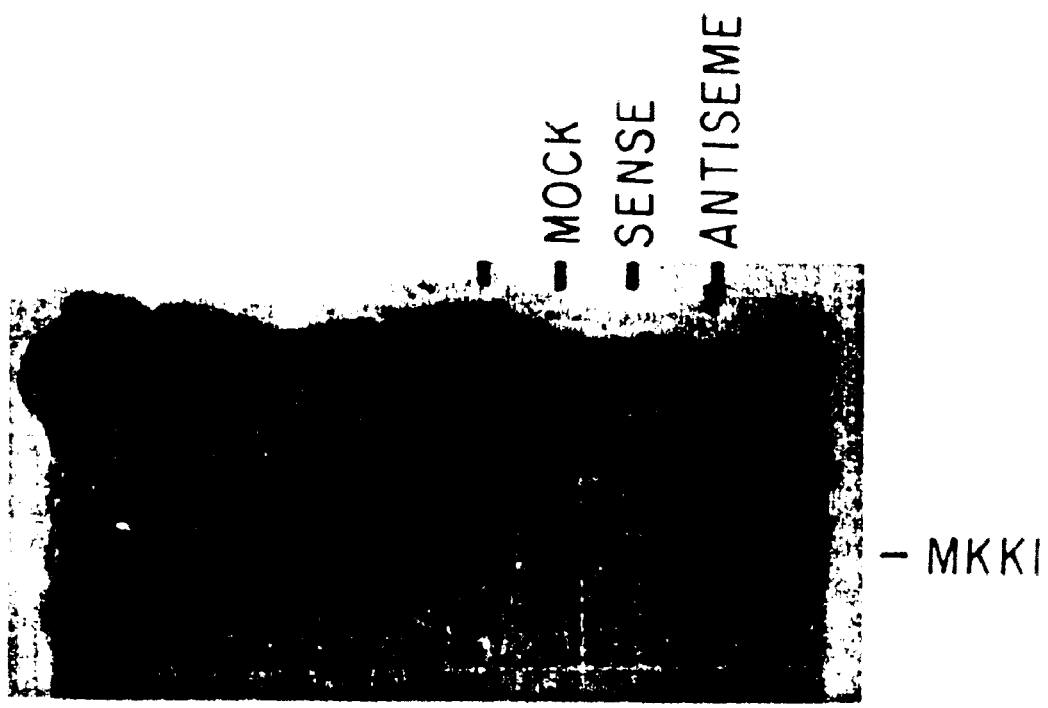

FIGS. 6A and 6B. FIGS. 6A–6B illustrate anti-sense MKK1 expression suppresses AChE Production in primary murine bone marrow cultures. FIG. 6A illustrates AChE production. FIG. 6B illustrates MKK1 protein expression.

Figure 7:

FIG. 7. MKK2 and MKK3 autophosphorylate and transphosphorylate proteins when expressed in bacteria. Lanes 2, 4, and 6 represent non-induced bacteria expressing MKK1, MKK2, MKK3, respectively. Lanes 1, 3, and 5 represent induced bacteria expressing MKK1, MKK2, MKK3, respectively.

Figure 8:
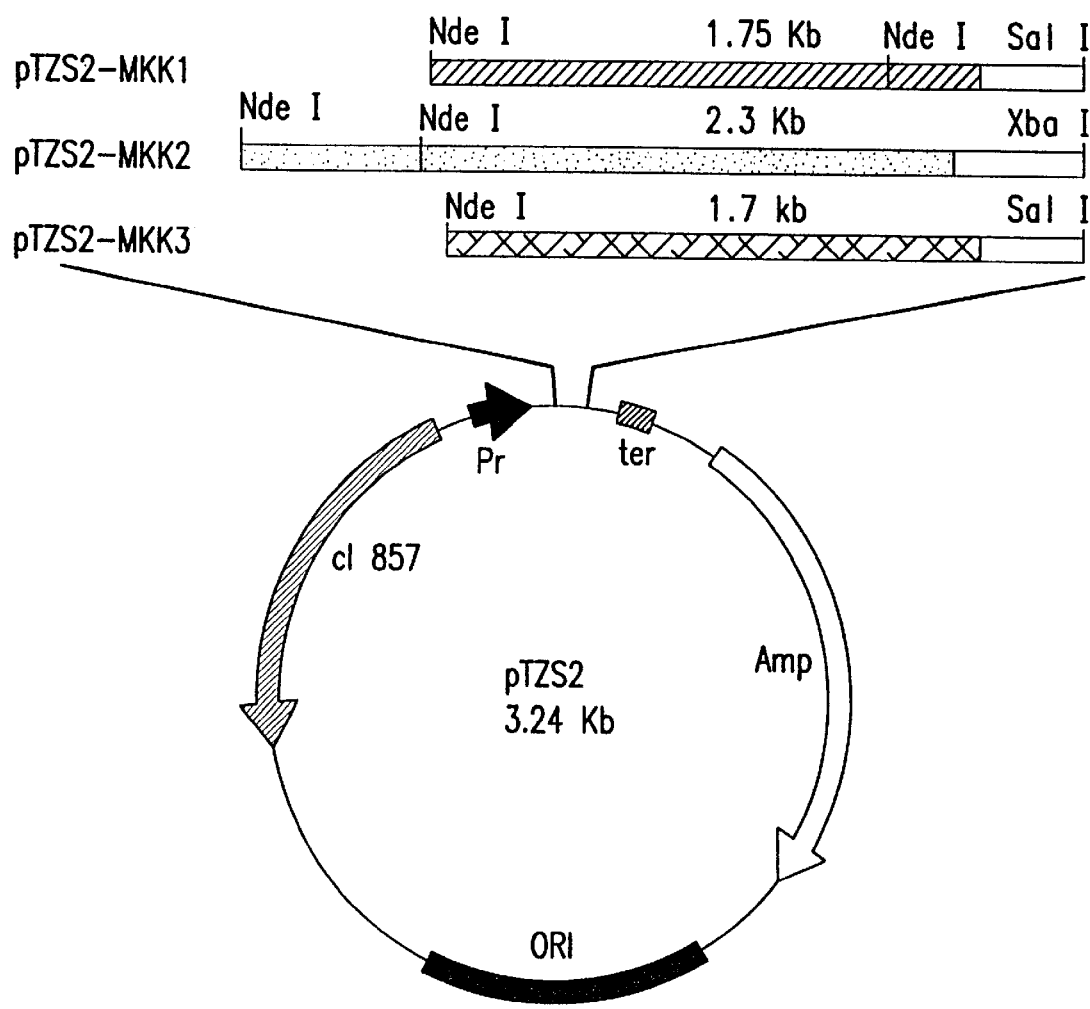

FIG. 8. MKK expression constructs.

FIG. 9. Shared amino acid sequence homology of MKK1 (SEQ ID NO:2) and csk (SEQ ID NO:7).

FIGS. 10A and 10B. Shared amino acid sequence homology of MKK2 (SEQ ID NO:4) and atk/btk (hAtk is SEQ ID NO:8; hTKT is SEQ ID NO:9; and mTec is SEQ ID NO:10).

FIGS. 11A, 11B, 11C and 11D. Shared amino acid sequence homology of MKK3 (SEQ ID NO:6) and src tyrosine kinase family members (hAtk is SEQ ID NO:11; cYrk is SEQ ID NO:12; hSrc is SEQ ID NO:13; hYes is SEQ ID NO:14; hFgr is SEQ ID NO:15, hLyn is SEQ ID NO:16; hHck is SEQ ID NO:17; hLck is SEQ ID NO:18; and mBlk is SEQ ID NO:19).

Figure 12:
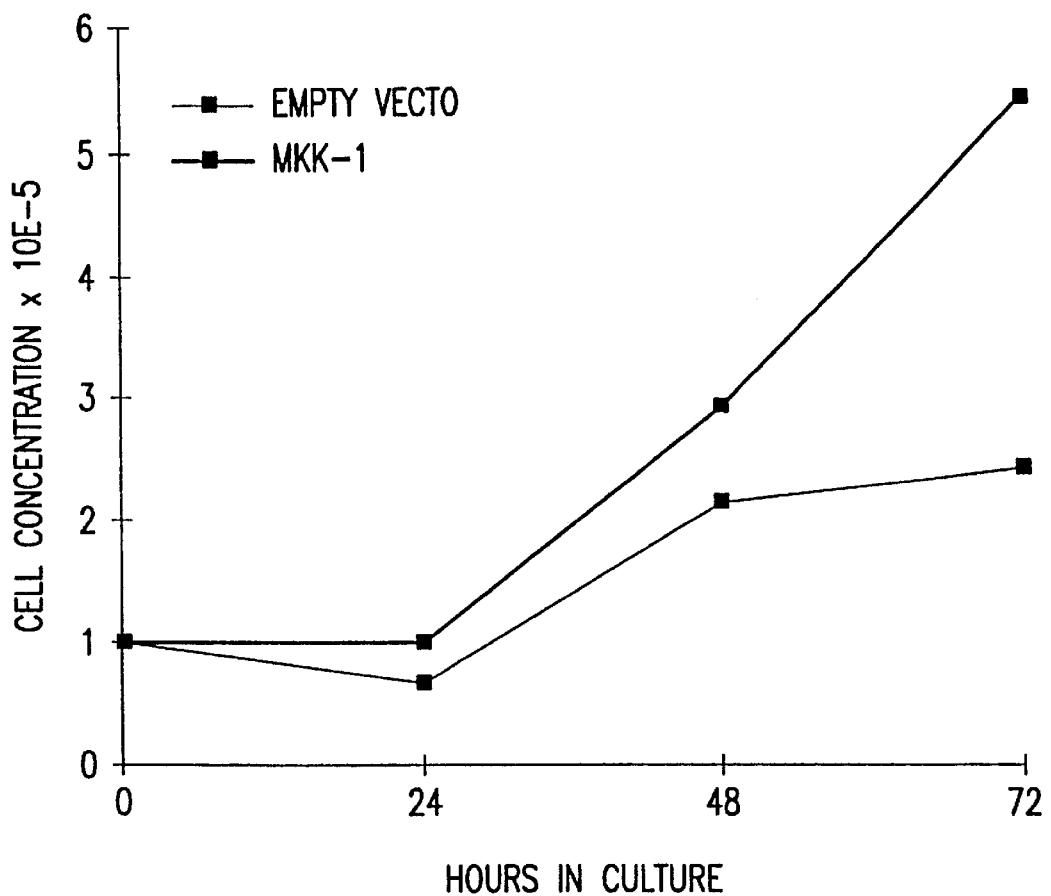

FIG. 12. FIG. 12 illustrates that the hyperexpression of MKK-1 in L-8057 cells grown in serum-free media inhibits cell growth of those cells as compared to control L-8057 cells.

Figure 13:
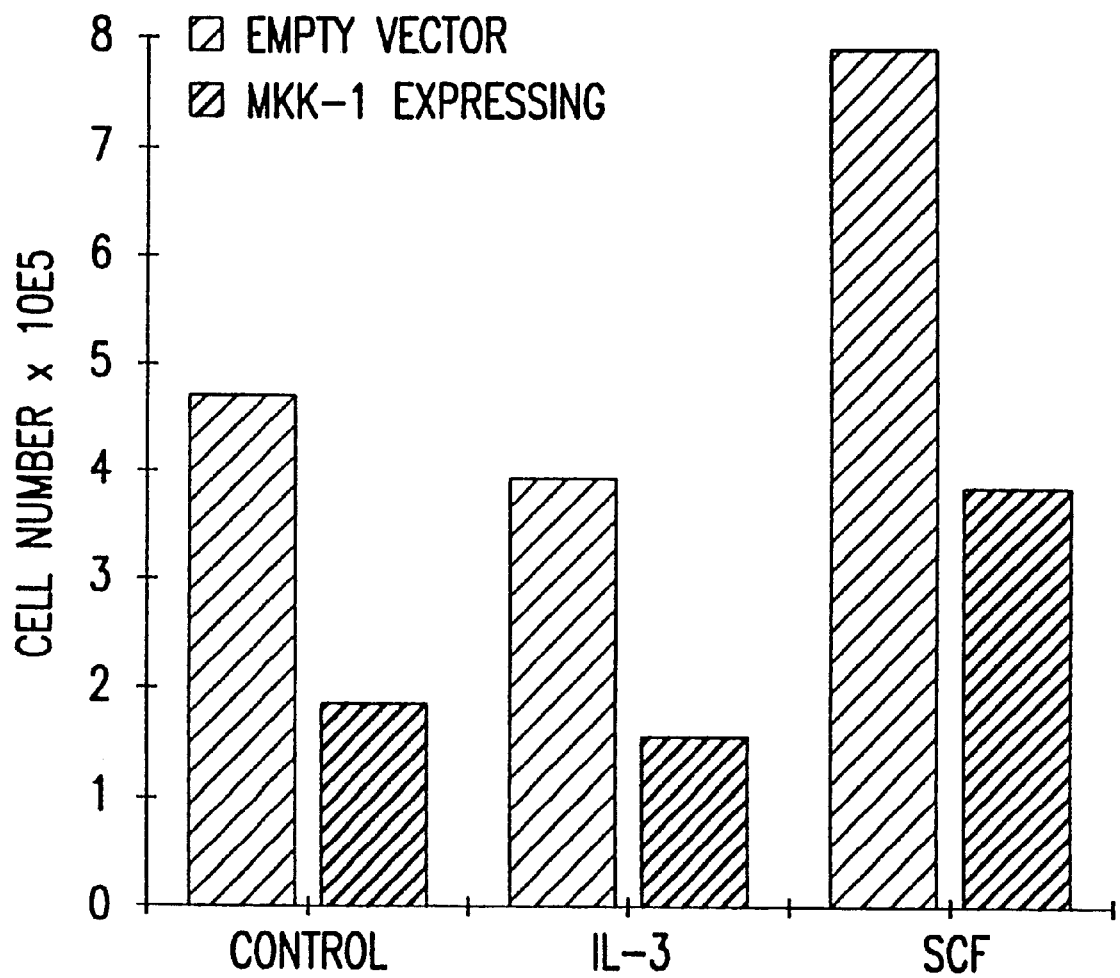

FIG. 13. FIG. 13 illustrates the stimulation of MKK-1 infected L-8057 cells and control L-8057 cells with rat stem cell factor and IL-3.

Figures 14A, 14B:
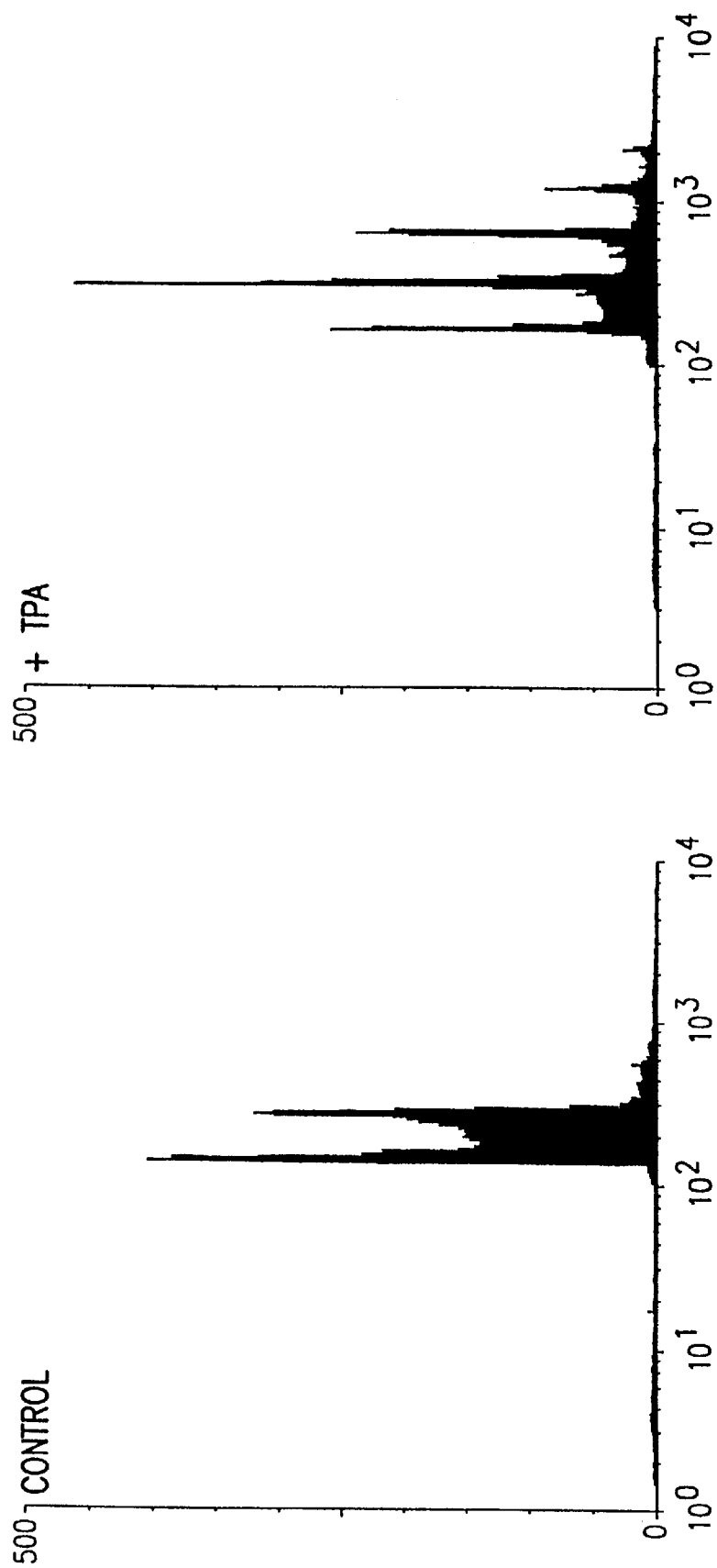
Figures 14C, 14D:
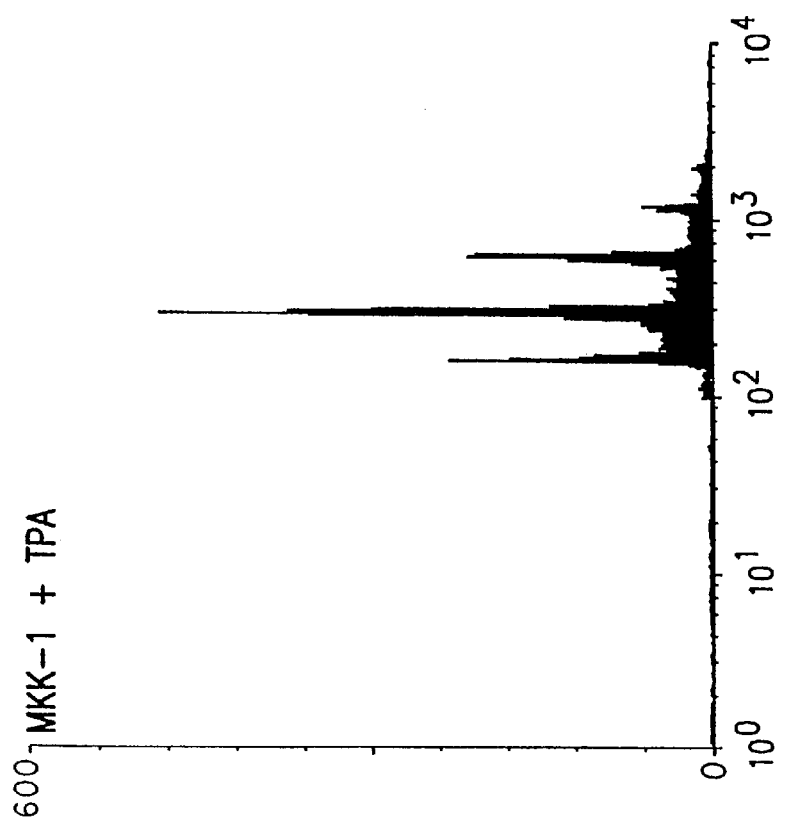

FIG. 14. FIG. 14 illustrates the effect of tetradecanoyl phorbol acetate ("TPA") on either control cells or cells that express MKK-1.

5. DETAILED DESCRIPTION

The present invention relates to novel, cytosolic megakaryocytic kinases referred to herein as "MKKs", and in particular to megakaryocyte kinase 1 (MKK1), megakaryocyte kinase 2 (MKK2), which are expressed in human megakaryocytic cell lines, and megakaryocyte kinase 3 (MKK3).

As used herein, MKK is a term which refers to MKK1, MKK2 and MKK3 from any species, including, bovine, ovine, porcine, equine, murine and preferably human, in naturally occurring-sequence or in variant form, or from any source, whether natural, synthetic, or recombinant. A preferred MKK variant is one having at least 80% amino acid homology, a particularly preferred MKK variant is one having at least 90% sequence homology and another particularly preferred MKK variant is one having at least 95% amino acid homology to the naturally occurring MKK.

MKK1 is a cytosolic tyrosine kinase of molecular weight 58 kD, as determined by SDS gel electrophoresis, having homology to the TK csk (Partanen, et al., *Oncogene* 6:2013–2018 (1991) and Nada et al., *Nature* 351:69–72 (1991)) in the intervening sequences of its catalytic domain, the SH2 and SH3 domains, and other non-catalytic regions and like csk, lacks regulatory phosphorylation sites corresponding to c-src tyrosines 416 and 527. MKK1 also lacks an amino-terminal myristylation site.

Csk is a recently described novel cytoplasmic TK that seems to play a key role in regulation of signal transduction in hematopoietic and neural development. For example csk has been shown to negatively regulate members of the src family of TKs, including c-src, lck, and fyn, through its ability to phosphorylate regulatory tyrosines. (Bergman et al., *The EMBO Journal* 11(8)8:2919–2924 (1992) and Sabe et al., *Molecular and Cellular Biology* 12(10):4706–4713 (1992)). Autero et al., (*Molecular and Cellular Biology* 14(2):1308–1321 (1994)) have reported that csk positively regulates a phosphatase, CD45, that is key to T-cell activity. Csk mediated phosphorylation of CD45 phosphotyrosine phosphatase (PTPase) caused a several fold increase in its PTPase activity. Csk appears to play a role as a regulator of the sequence of both phosphorylation and dephosphorylation events culminating in cell activation and proliferation.

Defective expression of csk in mouse embryos results in defects in the neural tube with subsequent death between day 9 and day 10 of gestation, with cells derived from these embryos exhibiting an order of magnitude increase in activity of src kinase (Nada et al., *Cell* 73:1125–1135 (1993)). Overexpression of csk in transformed rat 3Y1 fibroblasts was shown to cause reversion to normal phenotypes (Sabe et al., *Molecular and Cellular Biology* 12:4706–4713 (1992)).

MKK1 has 54% homology with csk at the amino acid level and structural similarity to csk, i.e., the lack of regulatory phosphorylation sites and the lack of an amino-terminal myristylation site. Experimental data, see Section 9, show that expression of human anti-sense MKK1 sequences inhibits synthesis of murine MKK1, which inhibition is associated with a reduction of proliferation of megakaryocytes in vitro. Based upon the experimental data in Section 9 and amino acid and structural homology with csk, MKK1 appears to play a regulatory role in the growth and differentiation of megakaryocytes and perhaps neural tissues based on its expression in those tissues.

MKK2 is a novel cytosolic tyrosine kinase of molecular weight 78 kD, as determined by SDS gel electrophoresis, having homology to the tec subfamily of TKs which also includes tsk and atk/btk. Like the tec subfamily, MKK2 lacks an amino-terminal site for myristylation and has a putative pleckstrin homology binding domain located 5' to the SH3 domain (Musacchio et al., TIBS 18:343–348 (1993)). The pleckstrin homology (PH) domain has been found in a number of proteins with diverse cellular functions and is abundant in proteins involved in signal transduction pathways. Musacchio et al., supra suggest that the PH domain may be involved in molecular recognition similarly to SH2 and SH3 domains.

The tec family of tyrosine kinases appear to play roles in cellular differentiation and include family members tec, a kinase which may be specifically involved in the cell growth of hepatocytes or hepatocarcinogenesis (Mano et al., supra); tsk, which may play a role in early T-lymphocyte differentiation (Heyek et al., PNAS USA 90:669–673 (1993)) and atk/btk. Aberrant expression of atk/btk has been shown to be responsible for X-linked agammaglobulinemia (XLA), a human disease resulting from a developmental block in the transition from pre-B cells to mature B cells (Ventrie, D. et al., supra).

MKK2 has 50% homology to atk/btk at the amino acid level and structural similarity to tec family members, i.e., the presence of the SH2, SH3 and PH domains and the lack of an amino-terminal site for myristylation and the carboxyl site of tyrosine phosphorylation found in family members. Based upon the amino acid homology and structural similarity to tec family members which play roles in cellular differentiation, MKK2 may play a role in the differentiation of megakaryoctyes.

NKK3 is a novel cytosolic tyrosine kinase of molecular weight 58 kD, as determined by SDS gel electrophoresis, having homology to the TK fyn. MKK3 does not have a myristylation sites. MKK3 does have a putative regulatory cite at tyr 387 but the surrounding 12 amino acids are not identical with other members of the src subfamily that share highly conserved sequences in this region. MKK3 has 47% homology with fyn at the amino acid level.

The fyn gene was originally characterized in normal human fibroblast and endothelial cells, but it is also expressed in a variety of other cell types. Alternative splicing of fyn has been shown to yield two distinct transcripts, both coding for enzymatically active forms of the kinases.

MKK sequences could be used diagnostically to measure expression of MKKs in disease states, such as for example leukemia, where abnormal proliferation of immature myeloid cells occurs, or where abnormal differentiation of megakaryocytes occurs. MKKs could also be used therapeutically in the treatment of disease states involving abnormal proliferation or differentiation through interruption of signal transduction by modulation of protein tyrosine kinases.

The nucleotide and deduced amino acid sequence of human MKK1, MKK2, and MKK3 are shown in FIGS. 1A–1B, 2A–2B and 3A–3B, respectively. FIGS. 9, 10A–10B and 11A–11D show the shared sequence homology between MKKs and related tyrosine kinases.

5.1. The MKK Coding Sequences

The nucleotide coding sequence and deduced amino acid sequence of the human MKK1, MKK2, and MKK3 genes are depicted in FIGS. 1A–1B, 2A–2B and 3A–3B, respectively. In accordance with the invention, any nucleotide sequence which encodes the amino acid sequence of an MKK gene product can be used to generate recombinant molecules which direct the expression of an MKK.

In a specific embodiment described herein, the human MKK1, MKK2, and MKK3 genes were isolated by performing polymerase chain reactions (PCR) in combination with two degenerate oligonucleotide primer pools that were designed on the basis of highly conserved sequences within the kinase domain of receptor tyrosine kinases corresponding to the amino acid sequence HRDLAA (sense primer) and SDVWS/FY (antisense primer) (Hanks et al., 1988). The MKK cDNAs were synthesized by reverse transcription of poly-A RNA from the human K-562 cell line, ATCC accession number CCL 243, or from the Meg 01 cell line, (Ogura et al., Blood 66:1384 (1985)).

The PCR fragments were used to screen a lambda gt11 library of human fetal brain. For each individual MKK, several overlapping clones were identified. The composite of the cDNA clones for MKK1, MKK2, and MKK3 are depicted in FIGS. 1A–1B, 2A–2B, and 3A–3B, respectively.

Further characterization of the individual MKKs is found infra.

5.2. Expression of MKK

In accordance with the invention, MKK polynucleotide sequences which encode MKKs, peptide fragments of MKKs, MKK fusion proteins or functional equivalents thereof, may be used to generate recombinant DNA molecules that direct the expression of MKK protein, MKK peptide fragment, fusion proteins or a functional equivalent thereof, in appropriate host cells. Such MKK polynucleotide sequences, as well as other polynucleotides which selectively hybridize to at least a part of such MKK polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the MKK protein. Such DNA sequences include those which are capable of hybridizing to the human MKK sequence under stringent conditions. The phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium citrate at 42° C; or (3) employ 50% formamide, 5×SSC (0.75 M NaCl, 0.075 M Sodium citrate), 5×Denhardt's solution, sonicated salmon sperm DNA 150 g/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within an MKK sequence, which result in a silent change thus producing a functionally equivalent NKK. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The DNA sequences of the invention may be engineered in order to alter an MKK coding sequence for a variety of ends including but not limited to alterations which modify processing and expression of the gene product. For example, mutations may be introduced using techniques which are well known in the art, e.g., site-directed mutagenesis, to insert new restriction sites, to alter glycosylation patterns, phosphorylation, etc.

In another embodiment of the invention, an MKK or a modified MKK sequence may be ligated to a heterologous sequence to encode a fusion protein. For example, for screening of peptide libraries for inhibitors of MKK activity, it may be useful to encode a chimeric MKK protein expressing a heterologous epitope that is recognized by a commercially available antibody. A fusion protein may also be engineered to contain a cleavage site located between an MKK sequence and the heterologous protein sequence, so that the MKK may be cleaved away from the heterologous moiety.

In an alternate embodiment of the invention, the coding sequence of an MKK could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10): 2331; Matteucci and Caruthers, 1980, *Tetrahedron Letters* 21:719; and Chow and Kempe, 1981, *Nuc. Acids Res.* 9(12):2807–2817. Alternatively, the protein itself could be produced using chemical methods to synthesize an MKK amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles*, W.H. Freeman and Co., N.Y. pp. 50–60). The composition of the synthetic peptides may be confirmed by amino acid analysis or sequencing (e.g., the Edman degradation procedure; see Creighton, 1983, *Proteins. Structures and Molecular Principles*, W.H. Freeman and Co., N.Y., pp. 34–49.

In order to express a biologically active MKK, the nucleotide sequence coding for MKK, or a functional equivalent, is inserted into an appropriate expression vector, i.e., a vector which contains the necessary elements for the transcription and translation of the inserted coding sequence. The MKK gene products as well as host cells or cell lines transfected or transformed with recombinant MKK expression vectors can be used for a variety of purposes. These include but are not limited to generating antibodies (i.e., monoclonal or polyclonal) that competitively inhibit activity of an MKK and neutralize its activity. Anti-MKK antibodies may be used in detecting and quantifying expression of an MKK in cells and tissues.

5.3. Expression Systems

Methods which are well known to those skilled in the art can be used to construct expression vectors containing an MKK coding sequence and appropriate transcriptional/ translational control signals. These methods include in vitro recombinant DNA techniques, synthetic techniques and in vivo recombination/genetic recombination. see, for example, the techniques described in Maniatis et al., 1989, *Molecular Cloning A Laboratory Manual*, Cold Spring Harbor Laboratory, N.Y. and Ausubel et al., 1989, *Current Protocols in Molecular Biology*, Greene Publishing Associates and Wiley Interscience, N.Y.

A variety of host-expression vector systems may be utilized to express an MKK coding sequence. These include but are not limited to microorganisms such as bacteria transformed with recombinant bacteriophage DNA, plasmid DNA or cosmid DNA expression vectors containing an MKK coding sequence; yeast transformed with recombinant yeast expression vectors containing an MKK coding sequence; insect cell systems infected with recombinant virus expression vectors (e.g., baculovirus) containing an MKK coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing an MKK coding sequence; or animal cell systems. The expression elements of these systems vary in their strength and specificities. Depending on the host/ vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of an MKK DNA, SV40-, BPV- and EBV-based vectors may be used with an appropriate selectable marker.

In bacterial systems a number of expression vectors may be advantageously selected depending upon the use intended for the MKK expressed. For example, when large quantities of MKK1 are to be produced for the generation of antibodies, vectors which direct the expression of high levels of fusion protein products that are readily purified may be desirable. Such vectors include but are not limited to the *E. coli* expression vector pUR278 (Ruther et al., 1983, *EMBO J.* 2:1791), in which the MKK1 coding sequence may be ligated into the vector in frame with the lac Z coding region so that a hybrid AS-lac Z protein is produced; pIN vectors (Inouye & Inouye, 1985, *Nucleic acids Res.* 13:3101–3109; Van Heeke & Schuster, 1989, *J. Biol. Chem.* 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, *Current Protocols in Molecular Biology*, Vol. 2, 1988, Ed. Ausubel et al., Greene Publish. Assoc. & Wiley Interscience, Ch. 13; Grant et al., 1987, *Expression and Secretion Vectors for Yeast*, in Methods in Enzymology, Ed. Wu & Grossman, 1987, Acad. Press, N.Y. 153:516–544; Glover, 1986, *DNA Cloning, Vol. II*, IRL Press, Wash., D.C., Ch. 3; and Bitter, 1987, Heterologous Gene Expression in Yeast, *Methods in Enzymology*, Eds. Berger & Kimmel, Acad. Press, N.Y. 152:673–684; and *The Molecular Biology of the Yeast Saccharomyces*, 1982, Eds. Strathern et al., Cold Spring Harbor Press, Vols. I and II.

In cases where plant expression vectors are used, the expression of an MKK coding sequence may be driven by any of a number of promoters. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J.* 6:307–311) may be used; alternatively, plant promoters such as the small subunit of RUBISCO (Coruzzi et al., 1984, *EMBO J.* 3:1671–1680; Broglie et al., 1984, *Science* 224:838–843); or heat shock promoters, e.g., soybean hsp17.5-E or hsp17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, *Methods for Plant Molecular Biology*, Academic Press, NY, Section VIII, pp. 421–463; and Grierson & Corey, 1988, *Plant Molecular Biology*, 2d Ed., Blackie, London, Ch. 7–9.

An alternative expression system which could be used to express an MKK is an insect system. In one such system, *Autographa californica* nuclear polyhidrosis virus (AcNPV) is used as a vector to express foreign genes. The virus grows in *Spodoptera frugiperda* cells. An MKK coding sequence may be cloned into non-essential regions (for example the polyhedrin gene) of the virus and placed under control of an AcNPV promoter (for example, the polyhedrin promoter). Successful insertion of an MKK coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, *J. Viol.* 46:584; Smith, U.S. Pat. No. 4,215,051).

In mammalian host cells, a number of viral based expression systems may be utilized. In cases where an adenovirus is used as an expression vector, an MKK coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing an MKK in infected hosts. (e.g., See Logan & Shenk, 1984, *Proc. Natl. Acad. Sci.* (*USA*) 81:3655–3659). Alternatively, the vaccinia 7.5 K promoter may be used. (See, e.g., Mackett et al., 1982, *Proc. Natl. Acad. Sci.* (*USA*) 79:7415–7419; Mackett et al., 1984, *J. Virol.* 49:857–864; Panicali et al., 1982, *Proc. Natl. Acad. Sci.* 79:4927–4931).

Specific initiation signals may also be required for efficient translation of an inserted MKK coding sequences. These signals include the ATG initiation codon and adjacent sequences. In cases where an entire MKK gene, including its own initiation codon and adjacent sequences, is inserted into the appropriate expression vector, no additional translational control signals may be needed. However, in cases where only a portion of an MKK coding sequence is inserted, exogenous translational control signals, including the ATG initiation codon, must be provided. Furthermore, the initiation codon must be in phase with the reading frame of an MKK coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express an MKK may be engineered. Rather than using expression vectors which contain viral origins of replication, host cells can be transformed with MKK DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express an MKK.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowy et al., 1980, *Cell* 22:817) genes can be employed in tk$^-$, hgprt$^-$ or aprt$^-$ cells, respectively. Also, antimetabolite resistance can be used as the basis of selection for dhfr, which confers resistance to methotrexate (Wigler et al., 1980, *Natl. Acad. Sci. USA* 77:3567; O'Hare et al., 1981, *Proc. Natl. Acad. Sci. USA* 78:1527); gpt, which confers resistance to mycophenolic acid (Mulligan & Berg, 1981), *Proc. Natl. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147). Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA* 85:8047); and ODC (ornithine decarboxylase) which confers resistance to the ornithine decarboxylase inhibitor, 2-(difluoromethyl)-DL-ornithine, DFMO (McConlogue L., 1987, *In: Current Communications in Molecular Biology*, Cold Spring Harbor Laboratory, Ed.).

5.4. Identification of Transfectants or Transformants that Express the MKK

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of MKK mRNA transcripts in the host cell; and (d) detection of the gene product as measured by immunoassay or by its biological activity.

In the first approach, the presence of the MKK coding sequence inserted in the expression vector can be detected by DNA-DNA or DNA-RNA hybridization using probes comprising nucleotide sequences that are homologous to the MKK coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the MKK1 coding sequence is inserted within a marker gene sequence of the vector, recombinant cells containing the MKK1 coding sequence can be identified by the absence of the marker gene function. Alternatively, a marker gene can be placed in tandem with an MKK sequence under the control of the same or different promoter used to control the expression of the MKK coding sequence. Expression of the marker in response to induction or selection indicates expression of the MKK coding sequence.

In the third approach, transcriptional activity for an MKK coding region can be assessed by hybridization assays. For example, RNA can be isolated and analyzed by Northern blot using a probe homologous to an MKK coding sequence or particular portions thereof. Alternatively, total nucleic acids of the host cell may be extracted and assayed for hybridization to such probes.

In the fourth approach, the expression of an MKK protein product can be assessed immunologically, for example by Western blots, immunoassays such as radioimmunoprecipitation, enzyme-linked immunoassays and the like.

5.5. Uses of MKK and Engineered Cell Lines

Megakaryocytes, the progenitor cell for blood platelets, and platelets are associated with disease states involving aberrant proliferation or differentiation of such cells, such as acute megakaryocytic leukemia, acute megakaryocytic myelosis and thrombocytopenia. MKKs appear to play a role in the growth and differentiation of megkaryocytes, therefore inhibitors of MKKs may be used therapeutically for the treatment of disease states resulting from aberrant growth of megakaryocytes or platelets. Alternatively, enhancers of MKKs may be used therapeutically to stimulate the proliferation of megakaryocytes in such applications as, for example, ex vivo culturing of megakaryocytes intended for autologous cell therapy in individuals receiving chemotherapy or other therapies which deplete megakaryocytes or platelets or in treating thrombocytopenia caused by other conditions.

In an embodiment of the invention, an MKK and/or cell line that expresses an MKK may be used to screen for antibodies, peptides, or other molecules that act as agonists or antagonists of MKK through modulation of signal transduction pathways. For example, anti-MKK antibodies capable of neutralizing the activity of MKK may be used to inhibit an MKK associated signal transduction pathway. Such antibodies can act intracellularly utilizing the techniques described in Marasco et al.(*PNAS* 90:7889–7893 (1993)) for example or through delivery by liposomes. Alternatively, screening of organic or peptide libraries with recombinantly expressed MKK protein or cell lines expressing MKK protein may be useful for identification of therapeutic molecules that function by modulating the kinase activity of MKK or its associated signal transduction pathway. A therapeutic molecule may find application in a disease state associated with megakaryocytes, such as acute megakaryocytic leukemia, or alternatively, in non-disease applications, for example in ex vivo culturing of megakaryocytes intended for autologous treatment of individuals undergoing chemotherapy. Synthetic compounds, natural products, and other sources of potentially biologically active materials can be screened in a number of ways deemed to be routine to those of skill in the art.

The ability of antibodies, peptides, or other molecules to prevent or mimic, the effect of MKK on signal transduction responses on MKK expressing cells may be measured. For example, responses such as activation or inhibition of MKK kinase activity or modulation of second messenger production may be monitored. The term "second messenger" as used herein refers to any component or product found in the cascade of signal transduction events. These assays may be performed using conventional techniques developed for these purposes.

5.5.1. Antibody Production and screening

Various procedures known in the art may be used for the production of antibodies to epitopes of the recombinantly produced MKK. Such antibodies include but are not limited to polyclonal, monoclonal, chimeric, single chain, Fab fragments and fragments produced by a Fab expression library. Neutralizing antibodies, i.e., those which inhibit the biological activity, i.e., the kinase activity, of an MKK are especially preferred for diagnostics and therapeutics.

For the production of antibodies, various host animals may be immunized by injection with an MKK protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum.*

Monoclonal antibodies to an MKK may be prepared by using any technique which provides for the production of antibody molecules by continuous cell lines in culture. These include but are not limited to the hybridoma technique originally described by Koehler and Milstein, (*Nature*, 1975, 256:495–497), the human B-cell hybridoma technique (Kosbor et al., 1983, *Immunology Today*, 4:72; Cote et al., 1983, *Proc. Natl. Acad. Sci.*, 80:2026–2030) and the EBV-hybridoma technique (Cole et al., 1985, *Monoclonal Antibodies and Cancer Therapy*, Alan R. Liss, Inc., pp. 77–96). In addition, techniques developed for the production of "chimeric antibodies" (Morrison et al., 1984, *Proc. Natl. Acad. Sci.* 81:6851–6855; Neuberger et al., 1984, *Nature*, 312:604–608; Takeda et al., 1985, *Nature* 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce an MKK-specific single chain antibodies.

Antibody fragments which contain specific binding sites of an MKK may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science* 246:1275–1281) to allow rapid and easy identification of monoclonal Fab fragments with the desired specificity for the MKK of interest.

5.5.2. Screening of Peptide Library with MKK or HKK Engineered Cell Lines

Random peptide libraries consisting of all possible combinations of amino acids attached to a solid phase support may be used to identify peptides that are able to bind to MKK binding sites, e.g., SH2, SH3 or PH binding sites, or other functional domains of an MKK, such as kinase domains. The screening of peptide libraries may have therapeutic value in the discovery of pharmaceutical agents that act to stimulate or inhibit the biological activity of an MKK.

Identification of molecules that are able to bind to an MKK may be accomplished by screening a peptide library with recombinant MKK protein. Methods for expression of an MKK are described in Section 5.2, 5.3 and 5.4 and may be used to express a recombinant full length MKK or fragments of an MKK depending on the functional domains of interest. For example, the kinase and SH2, SH3 or PH binding domains of an MKK may be separately expressed and used to screen peptide libraries.

To identify and isolate the peptide/solid phase support that interacts and forms a complex with an MKK, it is necessary to label or "tag" the MKK molecule. The MKK protein may be conjugated to enzymes such as alkaline phosphatase or horseradish peroxidase or to other reagents such as fluorescent labels which may include fluorescein isothyiocynate (FITC), phycoerythrin (PE) or rhodamine. conjugation of any given label to MKK may be performed using techniques that are routine in the art. Alternatively, MKK expression vectors may be engineered to express a chimeric MKK protein containing an epitope for which a commercially available antibody exists. The epitope specific antibody may be tagged using methods well known in the art including labeling with enzymes, fluorescent dyes or colored or magnetic beads.

The "tagged" MKK conjugate is incubated with the random peptide library for 30 minutes to one hour at 22° C. to allow complex formation between an MKK and peptide species within the library. The library is then washed to remove any unbound MKK protein. If MKK has been conjugated to alkaline phosphatase or horseradish peroxidase the whole library is poured into a petri dish containing a substrate for either alkaline phosphatase or peroxidase, for example, 5-bromo-4-chloro-3-indoyl phosphate (BCIP) or 3,3',4,4"-diamnobenzidine (DAB), respectively. After incubating for several minutes, the peptide/solid phase-MKK complex changes color, and can be easily identified and isolated physically under a dissecting microscope with a micromanipulator. If a fluorescent tagged MKK molecule has been used, complexes may be isolated by fluorescent activated sorting. If a chimeric MKK protein expressing a heterologous epitope has been used, detection of the peptide/MKK complex may be accomplished by using a labeled epitope specific antibody. Once isolated, the identity of the peptide attached to the solid phase support may be determined by peptide sequencing.

5.5.3. Screening of Organic Compounds with XKK Protein or Engineered Cell Lines

Cell lines that express an MKK may be used to screen for molecules that modulate MKK activity or signal transduction. Such molecules may include small organic or inorganic compounds or extracts of biological materials such as plants, fungi, etc., or other molecules that modulate MKK activity or that promote or prevent MKK mediated signal transduction. Synthetic compounds, natural products, and other sources of potentially biologically active materials can be screened in a number of ways.

The ability of a test molecule to interfere with MKK signal transduction may be measured using standard biochemical techniques. Other responses such as activation or suppression of catalytic activity, phosphorylation or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening. (See, for example, Peralidi, et al., J. Biochem. 285:71–78 (1992) or Campbell et al., JBC 268:7427–7434 (1993)).

Cellular processes under the control of an MKK signalling pathway may include, but are not limited to, normal cellular functions such as proliferation or differentiation of megakaryocytes or platelets, in addition to abnormal or potentially deleterious processes such as unregulated or inappropriate cell proliferation, blocking of differentiation of megakaryocytes or platelets, or ultimately cell death. The qualitative or quantitative observation and measurement of any of the described cellular processes by techniques known in the art may be advantageously used as a means of scoring for signal transduction in the course of screening.

MKK, or functional derivatives thereof, useful in identifying compounds capable of modulating signal transduction may have, for example, amino acid deletions and/or insertions and/or substitutions as long as they retain significant ability to interact with some or all relevant components of a MKK signal transduction pathway. A functional derivative of MKK may be prepared from a naturally occurring or recombinantly expressed MKK by proteolytic cleavage followed by conventional purification procedures known to those skilled in the art. Alternatively, the functional derivative may be produced by recombinant DNA technology by expressing parts of MKK which include the functional domain in suitable cells. Functional derivatives may also be chemically synthesized. Cells expressing MKK may be used as a source of MKK, crude or purified for testing in these assays.

MKK signal transduction activity may be measured by standard biochemical techniques or by monitoring the cellular processes controlled by the signal. To assess modulation of kinase activity, the test molecule is added to a reaction mixture containing MKK and a substrate. The kinase reaction is then initiated with the addition of ATP. An immunoassay using an antiphosphotyrosine antibody is performed on the kinase reaction to detect the presence or absence of the phosphorylated tyrosine residues on the substrate or to detect phosphorylated tyrosine residues on autophosphorylated MKK, and results are compared to those obtained for controls i.e., reaction mixtures not exposed to the test molecule.

5.6. Uses of MKK Polynucleotide

An MKK polynucleotide may be used for diagnostic and/or therapeutic purposes. For diagnostic purposes, an MKK polynucleotide may be used to detect MKK gene expression or aberrant MKK gene expression in disease states, e.g., acute megakaryocytic leukemia or acute megakaryocytic myelosis. Included in the scope of the invention are oligonucleotide sequences, that include antisense RNA and DNA molecules and ribozymes, that function to inhibit translation of an MKK. In a specific embodiment of this aspect of the invention, an anti-MKK1 antisense molecule is shown to inhibit MKK-1 protein synthesis resulting in reduced megakaryocyte growth and differentiation.

5.6.1. Diagnostic Uses of an MKK Polynucleotide

An MKK polynucleotide may have a number of uses for the diagnosis of diseases resulting from aberrant expression of MKK. For example, the MKK1 DNA sequence may be used in hybridization assays of biopsies or autopsies to diagnose abnormalities of MKK1 expression; e.g., Southern or Northern analysis, including in situ hybridization assays. Such techniques are well known in the art, and are in fact the basis of many commercially available diagnostic kits.

5.6.2. Therapeutic Uses of an MKK Polynucleotide

An MKK polynucleotide may be useful in the treatment of various abnormal conditions. By introducing gene sequences into cells, gene therapy can be used to treat conditions in which the cells do not proliferate or differentiate normally due to underexpression of normal MKK or expression of abnormal/inactive MKK. In some instances, the polynucleotide encoding an MKK is intended to replace or act in the place of a functionally deficient endogenous gene. Alternatively, abnormal conditions characterized by overproliferation can be treated using the gene therapy techniques described below.

Abnormal proliferation of megakaryocytes is an important component of a variety of disease states such as acute megakaryocytic leukemia, myelofibrosis, or acute megakaryocytic myelosis. Recombinant gene therapy vectors, such as viral vectors, may be engineered to express variant, signalling incompetent forms of MKK which may be used to inhibit the activity of the naturally occurring endogenous MKK. A signalling incompetent form may be, for example, a truncated form of the protein that is lacking all or part of its catalytic domain. Such a truncated form may participate in normal binding to a substrate but lack enzymatic activity. Thus recombinant gene therapy vectors may be used therapeutically for treatment of diseases resulting from aberrant expression or activity of an MKK. Accordingly, the invention provides a method of inhibiting the effects of signal transduction by an endogenous MKK protein in a cell comprising delivering a DNA molecule encoding a signalling incompetent form of the MKK protein to the cell so that the signalling incompetent MKK protein is produced in the cell and competes with the endogenous MKK protein for access to molecules in the MKK protein signalling pathway which activate or are activated by the endogenous MKK protein.

Expression vectors derived from viruses such as retroviruses, vaccinia virus, adeno-associated virus, herpes viruses, or bovine papilloma virus, may be used for delivery of recombinant MKK into the targeted cell population. Methods which are well known to those skilled in the art can be used to construct recombinant viral vectors containing an MKK polynucleotide sequence. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant MKK molecules can be reconstituted into liposomes for delivery to target cells.

Oligonucleotide sequences, that include anti-sense RNA and DNA molecules and ribozymes that function to inhibit the translation of an MKK mRNA are within the scope of the invention. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of an MKK nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of MKK1 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

Methods for introducing polynucleotides into such cells or tissue include methods for in vitro introduction of polynucleotides such as the insertion of naked polynucleotide, i.e., by injection into tissue, the introduction of an MKK polynucleotide in a cell ex vivo, i.e., for use in autologous cell therapy, the use of a vector such as a virus, retrovirus,

6. EXAMPLES
Cloning and Characterization of MKK1

For clarity of discussion, the subsection below describes the isolation and characterization of a cDNA clone encoding the novel tyrosine kinase designated MKK1. The MKK2 and MKK3 genes were cloned and characterized using the same methods.

6.1. cDNA Cloning, MKK Expression and MKK Characterization

Confluent plates of K-562 cells (ATCC accession number CCL 243) were lysed by treatment with guanidinium-thiocyanate according to Chirgwin et al. (1979, *Biochemistry* 18:5294–5299). Total RNA was isolated by CsCl-gradient centrifugation. First-strand cDNA was synthesized from 20 μg total RNA with avian myeloblastosis virus (AMV) reverse transcriptase (Boehringer Mannheim).

cDNA was used in a polymerase chain reaction under standard conditions (PCR Technology-Principles and Applications for DNA Amplifications, H. E. Erlich, Ed., Stockton Press, New York 1989). Degenerate pools of primers corresponding to the amino acid sequence HRDLAA and SDVWSF/Y were prepared and used for the amplification:

5' oligo pool (SEQ ID NO:20)

```
         H   R   D   L   A   A
5' GGAATTCC CAC AGN GAC TTN GCN GCN AG 3'
            T C     ATC     A   A   C
```

3' oligo pool (SEQ ID NO:21)

```
         F/Y S   W   V   D   S
5' GGAATTCC GAA NGT CCA NAC GTC NGA 3'
            ATG CA          C   C
```

Thirty-five PCR cycles were carried out using 8 μg (0.8 μg) of the pooled primers. (Annealing 55° C., 1 min; Extension 72° C., 2 min; Denaturation 94° C., 1 min). The reaction product was subjected to polyacrylamide gel electrophoresis. Fragments of the expected size (~210 bp) were isolated, digested with the restriction enzyme EcoRI, and subcloned into the pBluskript vector (Stratagene) using standard techniques (Current Protocols in Molecular Biology, eds. F. M. Ausubel et al., John Wiley & Sons, New York, 1988).

The recombinant plasmids were transformed into the competent *E. coli* strain designated 298.

The subcloned PCR products were sequenced by the method of Sanger et al. (*Proc. Natl. Acad. Sci. USA* 74, 5463–5467) using Sequenase (United States Biochemical, Cleveland, Ohio 44111 USA). Clones designated MKK1, MKK2, and MKK3 were identified as novel TKs.

6.1.1. Full-length cDNA Cloning

The partial cDNA sequence of the new MKK1 TK, which was identified by PCR, was used to screen a λgt11 library from human fetal brain cDNA (Clontech) (complexity of 1×10$^{10}$ recombinant phages). One million independent phage clones were plated and transferred to nitrocellulose filters following standard procedures (Sambrook, H. J., *Molecular Cloning*, Cold Spring Harbor Laboratory Press, USA, 1989). The filters were hybridized to the EcoRI/EcoRI fragment of clone MKK1, which had been radioactively labeled using 50 μCi [α$^{32}$P]ATP and the random-primed DNA labeling kit (Boehringer Mannheim). The longest cDNA insert of ~3500 bp was digested with the restriction enzymes EcoRI/SacI to obtain a 5' end probe of 250 bp. This probe was used to rescreen the human fetal brain library and several overlapping clones were isolated. The composite of the cDNA clones of MKK1, MKK2 and MKK3 is shown in FIGS. 1A–1B, 2A–2B and 3A–3B, respectively. The 1.75 million independent phage clones of a human placenta library, λZAP, were plated and screened with the 5' end probe (EcoRI/SacI) of the clone used above. Subcloning of positive bacteriophages clones into pBluskript vector was done by the in vivo excision protocol (Stratagene).

The composite cDNA sequence and the predicted amino acid sequence of MKK1, MKK2 and MKK3 are shown in FIGS. 1A–1B, 2A–2B and 3A–3B, respectively.

6.1.2. MKK Expression

*E. coli* expression constructs for MKK1, MKK2 and MKK3 were produced by cloning of the corresponding cDNA fragments into a plasmid expression vector pTZS2 (Ray et al., *PNAS USA* 89:(13):5705–5709 (1992)) by substitution of recoverin coding sequence with synthetic polylinker fragment. To provide in-frame connection of the coding sequences to prokaryotic translation initiation site coded by the vector, an NdeI restriction site overlapping start codon (CATATG) was introduced in all three MKK cDNAs by site directed mutagenesis. The resulting constructs are designed to drive expression of unfused proteins with authentic amino acid sequences. FIG. 8 shows MRK expression constructs.

6.1.3. RNA Blot Analysis of MKXs

Total RNA was isolated from human megakaryocytes, myeloid cells, B-cells, T-cells, and epithelial cells.

PolyA$^+$ RNA was isolated on an oligo (dT) column (Aviv and Leder, 1972, *Proc. Natl. Acad. Sci. USA* 69, 1408–1412). The poly A+ RNA was isolated using RNAstat −60 method (Tel-Test B Inc.) and blotted on a nitrocellulose filter using a slot blot apparatus (Schleicher and Schuell). 2 μg of poly A$^+$ RNA was loaded per lane. The filter was hybridized with a $^{32}$P-labeled EcoRI/EcoRI DNA fragment obtained by PCR. Subsequently, the filter was exposed to x-ray film at −70° C. with an intensifying screen. The results, as shown in FIG. 4, suggest that MKK1 and MKK2 are preferentially expressed in megakaryocytes. MKK3 expression could not be detected using this technique. FIG. 8 shows MKK expression constructs.

7. EXAMPLE
Autophosphorylation of MKK2 and KKK3

FIG. 7 represents Western blot analysis of protein from bacteria expressing MKK1, MKK2, or MKK3 using an anti-phosphotyrosine antibody (Hansen et al., *Electrophoresis* 14:112–126 (1993)). All MKK constructs were cloned into the inducible vector pTZS2, and transformed bacteria were grown under induced and uninduced conditions as described by Ray, et al.,(*PNAS USA* 89:5705–5709 (1992)). Bacterial pellets from these cultures were resuspended in sample buffer, containing 2-mercaptoethanol and SDS, and boiled. Proteins were separated by SDS-polyacrylamide gel electrophoresis. The results of this example indicate that MKK2 and MKK3 have kinase activity.

8. EXAMPLE
Production of Anti-MKK Antibodies and Immunoprecipitation of MKK

Antibodies recognizing MKK1 and MKK2 protein were made in rabbits using standard procedures. The anti-carboxy terminus MKK1 antibody was generated using the synthetic peptide GQDADGSTSPRSQEP which corresponds to residues 493–507 of amino acid sequence SEQ ID NO:2. The amino-terminus MKK1 Ab was generated using a GST-fusion proteins containing 78 amino acids coded by the SmaI to BG12 fragment of the MKK1 gene. The anti-carboxy terminus MKK2 Ab was made using a synthetic peptide corresponding to the sequence QQLLSSIIEPL-REKDKH which is residues 660–675 of amino acid sequence SEQ ID NO:4.

MKK1 and MKK2, cloned into the pBluskript plasmid, were transcribed and translated in the presence of $^{35}$S-methione using standards methods. Following protein synthesis MKK1 and MKK2 were immunoprecipitated (i.p.) with the appropriate rabbit antibodies (Ab) in the presence of SDS. FIG. 5 shows immunoprecipitation of in vitro transcribed and translated MKK1 and MKK2 proteins.

9. EXAMPLE

Expression of MKK1 Anti-sense sequences

Bone Marrow elements isolated from mice treated with 5-flurourocil 6 days prior to harvest were infected with retroviruses containing constructs expressing MKK1, anti-sense MKK1 (a truncated 5' EcoR1-PvuII fragment cloned in the reverse orientation) or the empty retroviral vector (mock). Following infection, cells were cultured and analyzed for the level of acetylcholinesterase (AChE) as previously described, measured as optical density at 414 nm (Hill, *Exp. Hematology* 20:354–360 (1992). A higher optical density reading indicates a greater AChE level and correlates with increased megakaryocyte growth and differentiation. Levels of the murine MKK1 protein were determined by metabolically labeling cells with $^{35}$S-methionine for 12 hours at the end of the experimental period. Following labeling, cells were lysed and MKK1 protein was isolated by two cycles of immunoprecipitation using anti-amino terminus MKK1 antibody. The proteins were resolved by polyacrylamide gel electrophoresis and visualized by autoradiography.

The retroviral construct used (pSR/MSV-Tkneo) was previously described (*Mol. Cell. Biol.* 11:1785–1792 (1991)). The MKK1 sense construct represents the full length gene lacking the poly-adenylation sequences. The MKK1 anti-sense construct represents the 5' fragment EcoRI-PvuII cloned in the reverse orientation. Both the sense and anti-sense constructs are driven by the retroviral long terminal repeat (LTR).

The results of the experiment, as shown in FIGS. 6A–6B, indicate that expression of the MKK1 anti-sense sequences in the cultured bone marrow elements is associated with decreased expression of MKK1 and decreased levels of AChE, an indicator of megakaryocyte growth and differentiation.

10. EXAMPLE

MXX1 Protein Tyrosine Kinase Activity

The protein tyrosine kinase activity of MKK1 was demonstrated through the incorporation of $^{32}$P in poly (Glu-Tyr) substrate by MKK1. The MKK1 used to demonstrate protein tyrosine kinase activity was obtained from 293 cells transiently overexpressing MKK1.

10.1. Materials and Methods 293 cells were transiently transfected with pCMP1-MKK1 (White, et al. *J. Biol. Chem.* (1987) 263:2969–2980), an expression vector containing nucleic acid encoding MKK1 operably linked to the CMV promoter. The 293 cells were harvested 48 hours after transfection and lysed in 1 ml of lysis buffer (20 mM tris-HCl [pH 7.4], 150 mM NaCl, 1% Triton X-100, 1 mM EDTA, 0.1 mM sodium orthovanadate, 0.1 mM PMSF) per one 10 cm culture dish. The lysates were collected by centrifugation at 20,000 g for 30 minutes. Control lysates were prepared in the same way as non-transfected 293 cells.

One ml aliquotes of the MKK1 transfected cell lysates and the control lysates, respectively, were incubated under constant agitation for 2 hours at 4° C. with 5 µl of polyclonal antiserum raised against a GST fusion protein containing amino acid residues 25–223 of the N-terminus of MKK1 and 15 µl of Protein A-Sepharose. The resultant MKK1 immunoprecipitates were spun down and washed with the lysis buffer twice; 50 mM tris-HCl [pH 7.4], twice; and either $Mg^{2+}$- or $Mn^{2+}$-containing kinase buffers (50 mM tris-HCl [pH 7.4], 5 mM of $MgCl_2$ or 5 mM $MnCl_2$, respectively), once. After the washes, the MKK1 immunoprecipitates were resuspended in 40 µl of either the $Mg^{2+}$- or $Mn^{2+}$-containing kinase buffers containing 1 mg/ml of poly (Glu-Tyr) 4:1 (Sigma, P-0275) and 10 µCi of gamma-32P-ATP (Amersham) and incubated for 20 minutes at 37° C. 10 µl aliquotes of the kinase reactions were spotted on glass paper filter (1205 Betaplate cassete filtermat, Beckman), and the filters were washed for 1.5 hours in three, sequential 100 ml volumes of (10% trichloroacetic acid, 10 mM sodium pyrophosphate). The washed filters were dried and analyzed by scintillation counting using BS Betaplate liquid scintillation counter (Beckman).

10.2. Results

Immunoprecipitates from MKK1 transiently transfected cells exhibited a 20–50-fold increase in counts over control cells, while no significant increase in counts was detected for immunoprecipitates from non-transfected cells or for MKK1 kinase assays carried out in the absence of poly (Glu-Tyr). Higher tyrosine kinase activity of MKK1 was observed in the presence of manganese than in the presence of magnesium.

11. EXAMPLE

Biological Activity of MKK1

In order to assess the biological activity of MKK1, a murine megakaryocytic cell line (L-8057) was infected with a retrovirus containing nucleic acid encoding MKK1 and the selectable drug-resistance marker, neomycin. Cell growth of the MKK1 expressing L-8057 cell lines and the ability of MKK1 expressing L-8057 cell lines to induce differentiation in the presence of tetradecanoyl phorbol acetate (TPA) was determined. The MKK1 expressing L-8057 cell lines were incubated with various cytokines to determine if any cytokine had the ability to block growth inhibition by MKK1.

11.1. Materials and Methods 11.1.1. Retroviral Infection of L-8057 cells

Aliquotes of about 2×10⁶ L-8057 cells (L-8057 cells were obtained from Dr. Yoji Ishida at the Iwate Medical University, Morioka, Japan) (about 1.5 ml of 8×10⁵ cells per ml in 15 ml conical tube) were prepared and collected by centrifugation. The collected cells were resuspended in 1.5 ml of viral stock of either ψ⁻ Eco msvTKneo MKK1 full length, designated V25, or ψ⁻ Eco msvTKneo, designated V6, (pPSR-a described in Muller et al.(1992) *Mol. Cell. Bio.* 11:1785–1792) containing 1.5 µl per ml of 6 mg/ml polybrene (Sigma, H 9268) and incubated at 37° C./5% $CO_2$ for 3 hours, with swirling every 30 minutes. The cells were then collected by centrifugation. An additional 1.5 ml of viral stock containing polybrene was added and the cells were incubated for an additional 3 hours as described above. The cells were collected by centrifugation, resuspended in 2 ml of standard L-8057 medium (20% fetal bovine serum (FBS), 40% RPMI, 40% IMDM (Gibco)), placed in 6 well plates and incubated at 37° C. for 2 days.

The cells were collected by centrifugation, resuspended in 1 ml of medium containing 1 mg/ml G-418 and placed in 6 cm dishes with 5 ml of medium containing G-418.

Non-infected L-8057 cells grown in media containing G-418 ($1 \times 10^5$ cells per ml in 10 cm dish) were used as a control.

Following drug-selection in G-418 and cell expansion, cells counts were made on days 5 and 6. Expression of MKK1 was verified by Western Blot.

11.1.2. Cell Growth Measurement of MKK1 Expressing L-8057 Cells

Cell growth of the MKK1 expressing L-8057 cell lines, designated V25A and V25B, along with mock-infected L-8057 cells and control cells was measured. Duplicate 6 well dishes plated at a cell density of $1 \times 10^5$/ml or $3.3 \times 10^4$/ml cells were prepared in 1% Nutridoma (Boehringer Mannheim). Cell counts were taken at days 5 and 6.

|      | Day 5 cell counts:      | Day 6 cell counts:      | vol. $2 \times 10^5$ cells |
|------|-------------------------|-------------------------|----------------------------|
| CNTL | $1.9 \times 10^6$/mL    | $1.6 \times 10^6$/mL    | 0.125 ml                   |
| V6   | $5.2 \times 10^5$/mL    | $4.0 \times 10^5$/mL    | 0.5 ml                     |
| V25A | $0.8 \times 10^5$/mL    | $0.8 \times 10^5$/mL    | 2.5 ml                     |
| V25B | $1.6 \times 10^5$/mL    | $1.0 \times 10^5$/mL    | 2.0 ml                     |

11.1.3. Growth Factor Response of MKK1 Expressing L-8057 Cells

The cells from one dish each of L-8057 cells infected with a retrovirus containing full length MKK1, designated V25A, and empty vector, designated $V_{6-1}$ were collected through centrifugation, washed with 10 ml of (IMDM, 1% Nutridoma, glutamine (Gibco), penicillin-streptomycin (Gibco) recentrifuged and resuspended in 2 ml of same medium. The cells were diluted to $2 \times 10^5$ cells/ml and 50 $\mu$l (or $10^4$ cells) were added per well of a 96 well plate and incubated for 24 hours under conditions of serum starvation. After serum starvation, rat stem cell factor, cKit ligand, IL-3, IL-6, IL-11, IL-1β, EPO, human MPL ligand, Spleen Cell Conditioned Medium (IL-3, IL-6) to a volume of 10%, WEHI 38 Conditioned Medium (IL-3, GM-CSF) to a volume of 10%, and fetal bovine serum to a volume of 10% (as a positive control) were added to the cells. The cells were allowed to grow for three days and cell growth was measured in a standard MTT (tetrazolium) assay (Mosmann, *J. Imm. Meth.* (1983) 65:55–63)

11.2. Results 11.2.1. Cell Growth

The highest MKK1 expression was observed in cells designated L-8057 V25A. No expression was observed in cells infected with the empty vector control, designated L-8057 V6. The growth rate was then examined under growth limiting conditions, i.e., in serum-free media. Compared with the empty vector control, cells infected with MKK1 grew at a much slower rate, see FIG. 12.

11.2.2. Cytokine Stimulation

Stimulation of the MKK1 infected L-8057 cells with a panel of cytokines, including rat stem cell factor (SCF), IL-3, IL-6, IL-11, IL-1β and EPO, revealed that only rat stem cell factor (SCF) was capable of overcoming the inhibition of proliferation produced by the hyperexpression of MKK1, see FIG. 13. The control cells also responded to SCF. The percent increase in the growth of the control cells treated with rat SCF and the MKK1 infected cells treated with rat SCF was similar. The data suggest that rat stem cell factor does not have the same signalling transduction pathway as MKK1.

11.2.3. Cell Differentiation

In order to test the effect of MKK1 on megakaryocyte differentiation, a murine megakaryocytic cell line (L-8057) was engineered to express MKK1, as described in Section 11.1.1. Induction of polyploidy (cells with DNA content greater than 4N) is a hallmark of megakaryocytic differentiation. L-8057 can be induced to differentiate (measured by induction of polyploidy and expression of the enzyme acetylcholinasterase in murine systems) by treatment with tetradecanoyl phorbol acetate (TPA) (Ishida et al., *Exp. Hematol.* 21:289–298, 1993). FIG. 14 demonstrates the effect of TPA on either control cells or cells that express MKK1. Both control cells and MKK1 expressing cells became polyploid to the same extent in response to treatment with TPA for 3 days. This data suggest that induction of differentiation is not affected by the presence of MKK1.

Various modifications of the invention, in addition to those shown and described herein, will become apparent to those skilled in the art from the foregoing description. Such modifications are intended to fall within the scope of the appended claims. It is also to be understood that all base pair sizes given for nucleotides are approximate and are used for purposes of description.

All references cited herein are hereby incorporated by reference in their entirety.

What is claimed is:

1. An isolated protein comprising the amino acid sequence shown in SEQ ID NO:4.

2. An isolated protein comprising at least one of the following peptide domains contained within the amino acid sequence depicted in SEQ ID NO:4: a Pleckstrin homology peptide domain; an SH2 domain; an SH3 domain; and a catalytic domain.

3. An isolated protein comprising at least one of the following amino acid sequences depicted in SEQ ID NO:4: amino acid residues 25 to 169; amino acid residues 296 to 375; amino acid residues 192–234; and amino acid residues 424 to 659.

4. A fusion protein comprising the isolated protein of claim 1 or 2 fused to a heterologous amino acid sequence.

5. An isolated protein comprising amino acid residues 660–675 of amino acid sequence SEQ ID NO:4.

6. An isolated protein which is encoded by a naturally occurring nucleic acid molecule which hybridizes under highly stringent conditions to the nucleic acid sequence which encodes the polypeptide of SEQ ID NO:4, wherein said stringent conditions are selected from the group consisting of:

(a) 0.15 M NaCl/0.0015 M sodiumcitrate/0.1% SDS at 50° C. for washing;

(b) 50% (vol/vol) formamide with 0.1% bovine serum albumin/0.1% Ficoll/0.1% polyvinylpyrrolidone/50 mM sodium phosphate buffer at pH 6.5 with 750 mM NaCl and 75 mM sodium citrate at 42° C. during hybridization; or (c) hybridzation in 50% formamide, 5×SSC, 5×Denhardt's solution, 50 g/ml sonicated salmon sperm DNA, 0.1% SDS, and 10% dextran sulfate at 42°, with washes at 42° in 0.2×SSC and 0.1% SDS.

7. An isolated protein comprising the amino acid sequence shown in SEQ ID NO:6.

8. An isolated protein comprising at least one of the following peptide domains contained within the amino acid sequence depicted in SEQ ID NO:6: an SH2 domain; an SH3 domain; and a catalytic domain.

9. An isolated protein comprising at least one of the following amino acid sequences depicted in SEQ ID NO:6: amino acid residues 122 to 201; amino acid residues 54 to 112; and amino acid residues 247 to 486.

10. A fusion protein comprising the isolated protein of claim 7 or 8 fused to a heterologous amino acid sequence.

11. An isolated protein which is encoded by a naturally occurring nucleic acid molecule which hybridizes under highly stringent conditions to the nucleic acid sequence which encodes the polypeptide of SEQ ID NO:6, wherein said stringent conditions are selected from the group consisting of:

(a) 0.15 M NaCl/0.0015 M sodiumcitrate/0.1% SDS at 50° C. for washing;

(b) 50% (vol/vol) formamide with 0.1% bovine serum albumin/0.1% Ficoll/0.1% polyvinylpyrrolidone/ 50mM sodium phosphate buffer at pH 6.5 with 750 mM NaCl and 75 mM sodium citrate at 42° C. during hybridization; or (c) hybridzation in 50% formamide, 5×SSC, 5×Denhardt's solution, 50 g/ml sonicated salmon sperm DNA, 0.1% SDS, and 10% dextran sulfate at 42°, with washes at 42° in 0.2×SSC and 0.1% SDS.

\* \* \* \* \*